(12) United States Patent
Maynard et al.

(10) Patent No.: US 8,653,243 B2
(45) Date of Patent: Feb. 18, 2014

(54) PERTUSSIS ANTIBODIES AND USES THEREOF

(75) Inventors: Jennifer Maynard, Austin, TX (US); Jamie Sutherland, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/236,530

(22) Filed: Sep. 19, 2011

(65) Prior Publication Data

US 2012/0244144 A1  Sep. 27, 2012

Related U.S. Application Data

(60) Provisional application No. 61/384,104, filed on Sep. 17, 2010.

(51) Int. Cl.
C07K 16/12 (2006.01)
A61K 39/40 (2006.01)

(52) U.S. Cl.
USPC .................. 530/387.3; 530/388.4; 424/133.1; 424/135.1; 424/150.1

(58) Field of Classification Search
None
See application file for complete search history.

(56) References Cited

U.S. PATENT DOCUMENTS 6,884,879 B1 * 4/2005 Baca et al. .................. 536/23.53
2007/0237779 A1 * 10/2007 Ledbetter et al. .......... 424/155.1

OTHER PUBLICATIONS

Pai et al., Recent Pat Antiinfect Drug Disc., Jan. 2009; 4(1):1-17.*
Pootong et al., Asian Pac J Allergy Immunol 2007; 25:37-45.*
Antoine, R. et al., "Roles of the disulfide bond and the carboxy-terminal region of the S1 subunit in the assembly and biosynthesis of *pertussis* toxin", Infection and Immunity 58(6):1518-1526, Jun. 1990.
Bartoloni, A. et al., "Mapping of a protective epitope of *pertussis* toxin by in vitro refolding of recombinant fragments", Nature Biotechnology 6:709-712, Jun. 1988.
Bruss, J.B. et al., "Protective effects of *pertussis* immunoglobulin (P-IGIV) in the aerosol challenge model", Clinical and Diagnostic Laboratory Immunology 6(4):464-470, Jul. 1999.
Bruss, J.B. et al., "Quantitative priming with inactivated *pertussis* toxoid vaccine in the aerosol challenge model", Infection and Immunity 70(8):4600-4608, Aug. 2002.
Bruss, J.B. et al., "Treatment of severe *pertussis*: a study of the safety and pharmacology of intravenous *pertussis* immunoglobulin", The Pediatric Infectious Disease Journal 18(6):505-511, Jun. 1999.
Burnette, W.N. et al., "*Pertussis* toxin S1 mutant with reduced enzyme activity and a conserved protective epitope", Science 242:72-74, 1988.
Cieplak, W. et al., "Identification of a region in the S1 subunit of *pertussis* toxin that is required for enzymatic activity and that contributes to the formation of a neutralizing antigenic determinant", Proc

(56) References Cited

OTHER PUBLICATIONS

Sato, H. et al., "Comparison of *pertussis* toxin (PT)-neutralizing activities and mouse-protective activities of anti-PT mouse monoclonal antibodies", Infection and Immunity 59(10):3832-3835, Oct. 1991.

Sato, Y. et al., "Separation and purification of the hemagglutinins from *Bordetella pertussis*", Infection and Immunity 41(1):313-320, 1983.

Smith, M.J. et al., "Monoclonal antibody 11E10, which neutralizes shiga toxin type 2 (Stx2), recognizes three regions on the Stx2 A subunit, blocks the enzymatic action of the toxin in vitro, and alters the overall cellular distribution of the toxin", Infection and Immunity 77(7):2730-2740, May 2009.

Storsaeter, J. et al. "Levels of anti-*pertussis* antibodies related to protection after household exposure to *Bordetella pertussis*", Vaccine 16(20):1907-1916, 1998.

Sutherland, J.N. et al., "Characterization of a key neutralizing epitope on *pertussis* toxin recognized by monoclonal antibody 1B7", Biochemistry 48:11982-11993, 2009.

Weiss, A.A. et al., "Tn5-induced mutations affecting virulence factors of *Bordetella pertussis*", Infection and Immunity 42(1):33-41, 1983.

Witvliet, M.H. et al., "Binding of *pertussis* toxin to eucaryotic cells and glycoproteins", Infection and Immunity 57(11):3324-3330, Nov. 1989.

\* cited by examiner

PERTUSSIS ANTIBODIES AND USES THEREOF

CROSS-REFERENCES TO RELATED APPLICATIONS

This application claims the benefit of U.S. Provisional Application No. 61/384,104 filed Sep. 17, 2010, which is hereby incorporated in its entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 93331-817547_ST25.TXT, created on Mar. 14, 2013, 34,765 bytes, machine format IBM-PC, MS-Windows operating system, is hereby incorporated by reference.

STATEMENT AS TO RIGHTS TO INVENTIONS MADE UNDER FEDERALLY SPONSORED RESEARCH OR DEVELOPMENT

This invention was made with government support under AI0662339 awarded by the National Institutes of Health. The Government has certain rights in the invention.

BACKGROUND OF THE INVENTION

*Bordetella pertussis*, the etiologic agent of whooping cough, is a highly infectious human pathogen with a strong capacity to infect the human respiratory tract (Kerr and Matthews, 2000). It is presently one of the ten most common causes of death from infectious disease, reported by the World Health Organization to cause 50 million cases per year (Kerr and Matthews, 2000). Infection occurs primarily in the unvaccinated populations in developing countries. While once effectively controlled in industrialized countries through vaccination, pertussis cases have been rebounding in the last ten years, due to decreased vaccination, antigenic drift (deMelker et al., 2000; Mooi et al., 2001) and transmission from adult reservoirs (Anonymous, 1995b; Deen et al., 1995; Senzilet et al., 2001). Thus, there is a need in the art for effective treatments of diseases caused by the *Bordetella pertussis* bacterium. Provided herein are methods and compositions addressing these and other needs in the art.

BRIEF SUMMARY OF THE INVENTION

In one aspect, a humanized antibody capable of binding a pertussis toxin protein is provided. The humanized antibody includes a humanized heavy chain and a humanized light chain.

In another aspect, an isolated nucleic acid encoding a humanized antibody capable of binding a pertussis toxin protein is provided. The antibody includes a humanized heavy chain and a humanized light chain.

In one aspect, a pertussis toxin protein S1-S4 conjugate is provided.

In another aspect, a vaccine including a pertussis toxin protein S1-S4 conjugate and a pharmaceutically acceptable excipient is provided.

In another aspect, a pharmaceutical composition including a therapeutically effective amount of a humanized antibody capable of binding a pertussis toxin protein and a pharmaceutically acceptable excipient is provided.

In another aspect, a method for immunizing a host susceptible to a disease caused by *Bordetella pertussis* bacterium (e.g. whooping cough) is provided. The method includes administering a pertussis toxin protein S1-S4 conjugate to the host under conditions such that antibodies directed to the pertussis toxin protein S1-S4 conjugate or a functional fragment thereof are produced.

In one aspect, a method of treating a disease caused by *Bordetella pertussis* bacterium (e.g. whooping cough) in a subject in need thereof is provided. The method includes administering to the subject a therapeutically effective amount of a humanized antibody capable of binding a pertussis toxin protein and a pharmaceutical carrier, thereby treating whooping cough in the subject.

BRIEF DESCRIPTION OF THE DRAWINGS

FIG. 1. Model of pertussis toxin function. The 1B7 antibody neutralizes toxin catalytic function while the 11E6 antibody competes with the cellular receptor for B-oligomer binding. After the toxin binds glycoproteins or glycolipids on the host cell, it undergoes receptor-mediated endocytosis and retrograde transport through the endosome to the Golgi apparatus and finally the ER. In the ER, ATP binds to the central pore of the B-oligomer, resulting in the release of the S1 subunit which is subsequently reduced and exposed to the cytosol (it may remain associated with the membrane associated via the hydrophobic tail). In the cytosol, PTx-S1 ADP-ribosylates G proteins, disrupting normal signaling and increasing cAMP levels.

FIG. 2. Representative BIAcore 3000 (GE Healthcare, Uppsala, Sweden) SPR runs on a CM5 chip with mAb 1B7 coupled at ~1000 RU. A) PTx holotoxin at 300, 200, 150, 100, and 50 nM; B) PTx-S1 at 200, 150, 100, and 50 nM; C) PTx-S1-220 at 300, 200, 150, 100, and 50 nM; and D) B-oligomer at 2890, 2300, 2000, 1730, and 1150 nM.

FIG. 3. Immunoblot analysis of 1B7 antibody constructs. After electrophoresis of 23 pmol of the B-oligomer, PTx, and PTx-S1 and 46 pmol of PTx-S1-220 in three identical sections on a 12% SDS-PAGE gel, proteins were electrophoretically transferred to nitrocellulose paper. The antibody constructs mAb 1B7 at 2.9 mg, m1B7 at 5.9 mg, and hu1B7 and 5.9 mg were used to probe a section each with subsequent detection using equivalent amounts of anti-mouse-Fc HRP, anti-human-$C_k$ HRP, and anti-human-$C_k$ HRP, respectively.

FIG. 4. Tryptophan fluorescence spectra of hu1B7 (□), L-W91A (—), H-W33A (x), PTx-S1-220 (Δ), and the hu1B7/PTx-S1-220 complex (♦) in PBS. A) hu1B7, L-W91A, and H-W33A comparison at 4.5 μM at room temperature. Lines indicate spectral peaks at 352 nm, 352 nm, and 355 nm, respectively. B) hu1B7, PTx-S1-220, and the hu1B7/PTx-S1-220 complex at a 1:1 molar ratio comparison at 4.5 μM at room temperature. Lines indicate spectral peaks at 357 nm, 362 nm, and 353 nm, respectively.

FIG. 5. The 1B7-PTx best fit interaction model generated by RosettaDock using the crystal structure of PTx and the WAM predicted structure of hu1B7. Experimentally determined important interacting residues on both PTx-S1 and hu1B7 are shown.

FIG. 6. ELISA of PTx and B-oligomer with primary antibody of 1B7(Δ), 11E6 (x), or the negative control, c-myc, representing non-specific antibody binding (no symbol).

FIG. 7. Electron micrograph showing *B. pertussis* attached to ciliated epithelial cells (Todar 2000).

FIG. 8. Pertussis toxin, showing the active S1 subunit sitting atop the asymmetric pentamer formed by five subunits of the binding domain. (Produced with Rasmol from PDB file 1PRT (Stein et al., 1994).)

FIG. 9. Pertussis Toxin Mechanism. (1) the B subunit associates via subunits S2 and S3 with siaylated glycoproteins and glycolipids; (2) the holotoxin is presumed to be endocytosed and to undergo retrograde transport to the Golgi apparatus (3) and possibly the endoplasmic reticulum (4). In the presence of ATP and a reducing environment, the S1 subunit dissociates from the holotoxin and its single disulfide bond is reduced, exposing a hydrophobic domain that allows S1 to bind and translocate through the ER membrane into the cytoplasm. There, the active S1 subunit catalyzes the transfer of an ADP-ribose from NAD+ to cysteine 351 of the α-subunit of inhibitory G proteins (5). This modification prevents the exchange of GDP for GTP in the α-subunit thereby blocking the dissociation of the βγ subunit from the α subunit (6), inactivating the G protein and preventing its inhibition of adenylate cyclase (7).

FIG. 10. CHO cell clustering assay. A, normal CHO cell morphology in the absence of pertussis toxin; B, early transition region with the appearance of some clustering; C, late transition region with mixed clustering and normal morphology; D, clustering morphology in the presence of 10 ng/ml PT. 10× magnification is shown.

FIG. 11. Size exclusion purification of 1B7 variants, obtained from 0.75 L culture. A, 1B7 scFv and scAb in which light chain cysteine 23 has been restored. B, 1B7 variants retaining the L23Cys:Phe substitution. Note the distribution of scAb fragments into monomeric, dimeric, and aggregated species, and the differences in yield between scFv and scAb production and the presence of Cys23.

FIG. 12. Amino acid sequence alignment of: (1) parental 1B7 (top; SEQ ID NO:56); (2) humanized version of 1B7 (middle; SEQ ID NO:60); and (3) consensus germline sequence for human VκI and VHIII (SEQ ID NO:61).

FIG. 13. Representative data from competition ELISAs. Raw data is shown on the left; transformed data from which the equilibrium dissociation constant is calculated, on the right. Competition was performed with 5 nM antibody, twofold dilutions of pertussis toxin from 25 nM.

FIG. 14. Anti-pertussis toxin antibody stability to high temperature denaturation as measured by the retention of binding activity. Antibodies (16 µg/ml in PBS) were treated in triplicate for two hours at 4, 50, or 70° C., and activity was estimated by direct ELISA (shown above). A decrease in absorbance at a given concentration of antibody indicates a drop in activity, which can be quantitatively assessed by comparing the antibody concentrations resulting in 50% maximum absorbance (i.e., 4° C. 50%*100%/high temp 50%). See Table 8 for complete results.

FIG. 15. scAb stability at 37° C. as measured by anti-PT ELISA reactivity. scAbs at 100 µg/ml were incubated in PBS for times varying from 0-48 hours at 37° C. Remaining activity was measured as the concentration of antibody resulting in 50% of the maximum ELISA signal for untreated antibody. See Table 8 for a numerical comparison.

FIG. 16. 1B7 antibody does not directly mediate B. pertussis killing. Upper Panel: Binding of the 1B7 and 11E6 monoclonal antibodies and anti-pertussis or control meningococcal polyclonal antibodies to live B. pertussis, as measured by FACS. Lower Panel: Opsonophagocytic activity of neutrophils recognizing antibody-bound bacteria, measured as respiratory burst (RB %).

FIG. 17. PTx can simultaneously bind a model receptor and neutralizing antibodies. A binding assay was performed in which a model receptor, transferrin, was coated onto ELISA plates. After blocking, PTx was added, then monoclonal antibody, then anti-mouse-HRP. The 1B7 and 11E6 neutralizing antibodies but not isotype controls, bind transferrin-bound receptor. Two additional non-neutralizing antibodies, 3F9 and G9A, also recognized transferrin-bound PTx.

FIG. 18. PTx S1-220 is stabilized at lower pH characteristic of endolysosomes. Fluorescent anisotropy measurements were performed with PTx-S1-220-FITC at various buffer conditions from pH 5.5-7.2.

FIG. 19. Visualization of PTx retrograde transport in CHO cells. PTx was added to adherent Cho cells, allowed to incubate for the indicated time period before washing and fixing. Cells were permeabilized and PTx detected with 0.5 µg/ml mAb 1B7 and 1:1000 dilution anti-mouse-Cy5. Organelle location was detected simultaneously as indicated below. Data shown are representative images, experiments were repeated 3 times. A, PTx co-localization in the early/recycling endosomes as detected with 25 ng/ml transferrin-ALEXA at 20, 30 and 45 min. B, PTx co-localization in the Golgi labeled using Golgi-GFP organelle lights at 1, 2 and 3 hrs. C, PTx co-localization in the ER labeled with anti-PDI and anti-rabbit-Cy3 at 20 min, 2 and 4 hr.

FIG. 20. Initial docked model generated by Z-dock using the crystal structure of PTx and the WAM predicted structure of hu1B7. Mutated residues on both PTx-S1 and hu1B7 are shown.

DETAILED DESCRIPTION OF THE INVENTION

Figure 1:
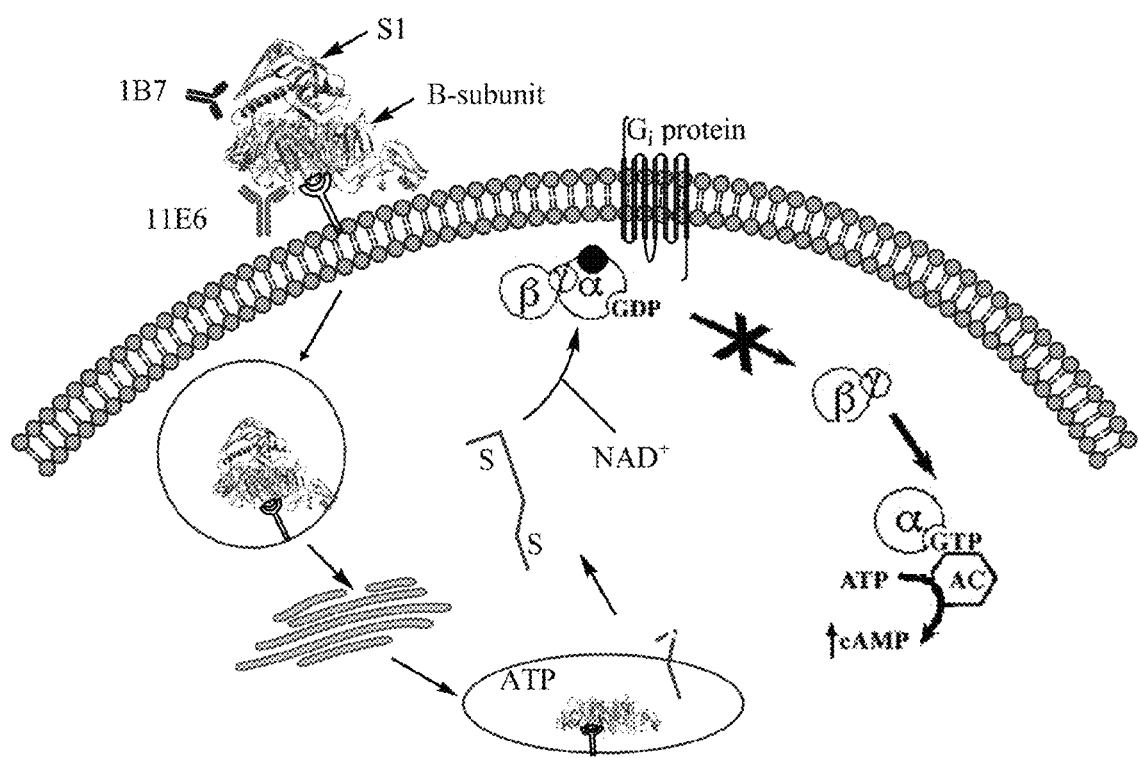
Figure 2A:
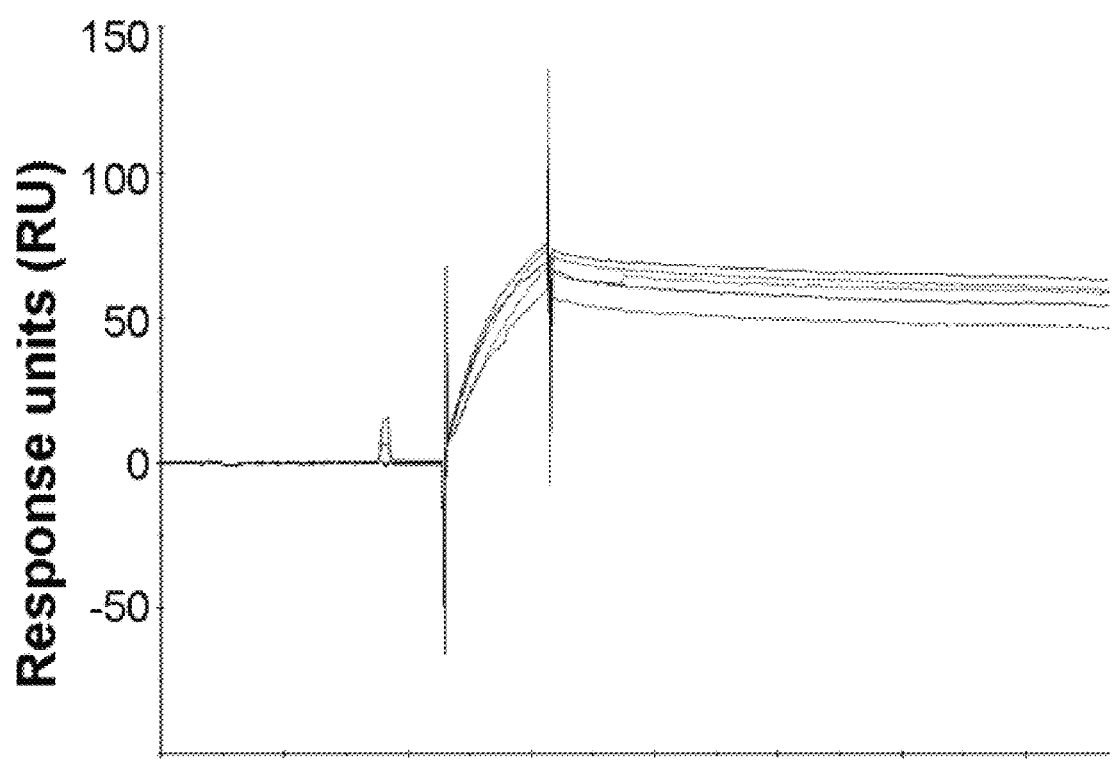
Figure 2B:
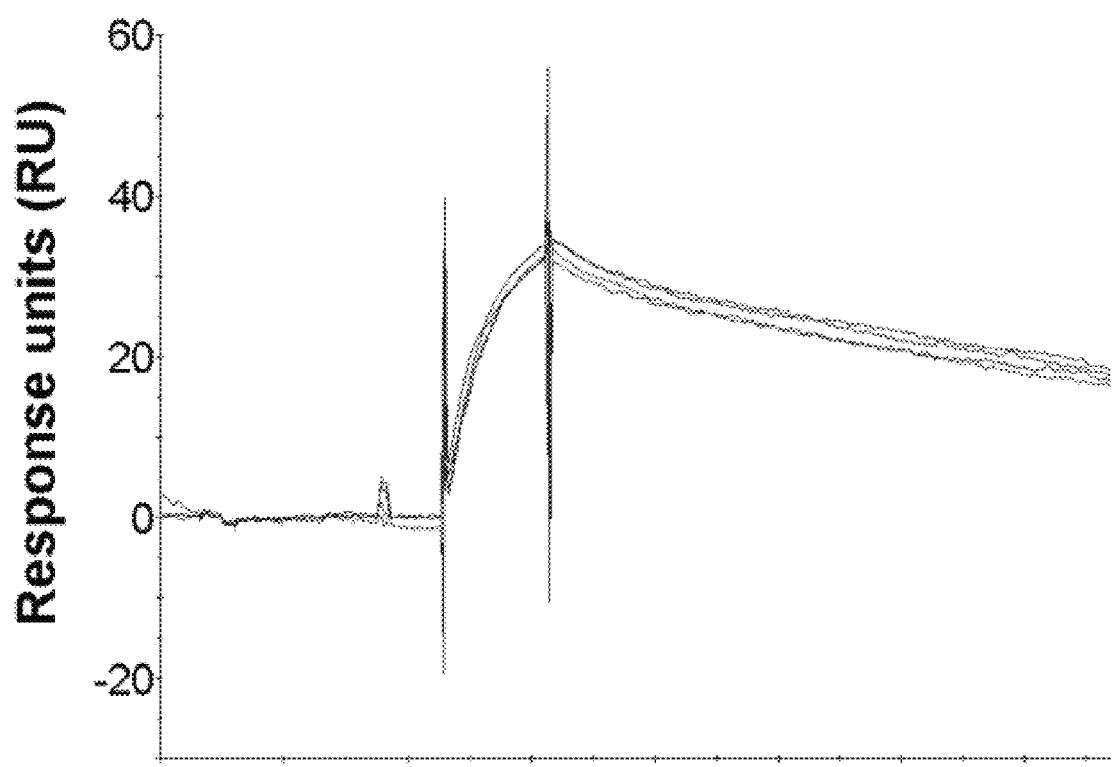
Figure 2C:
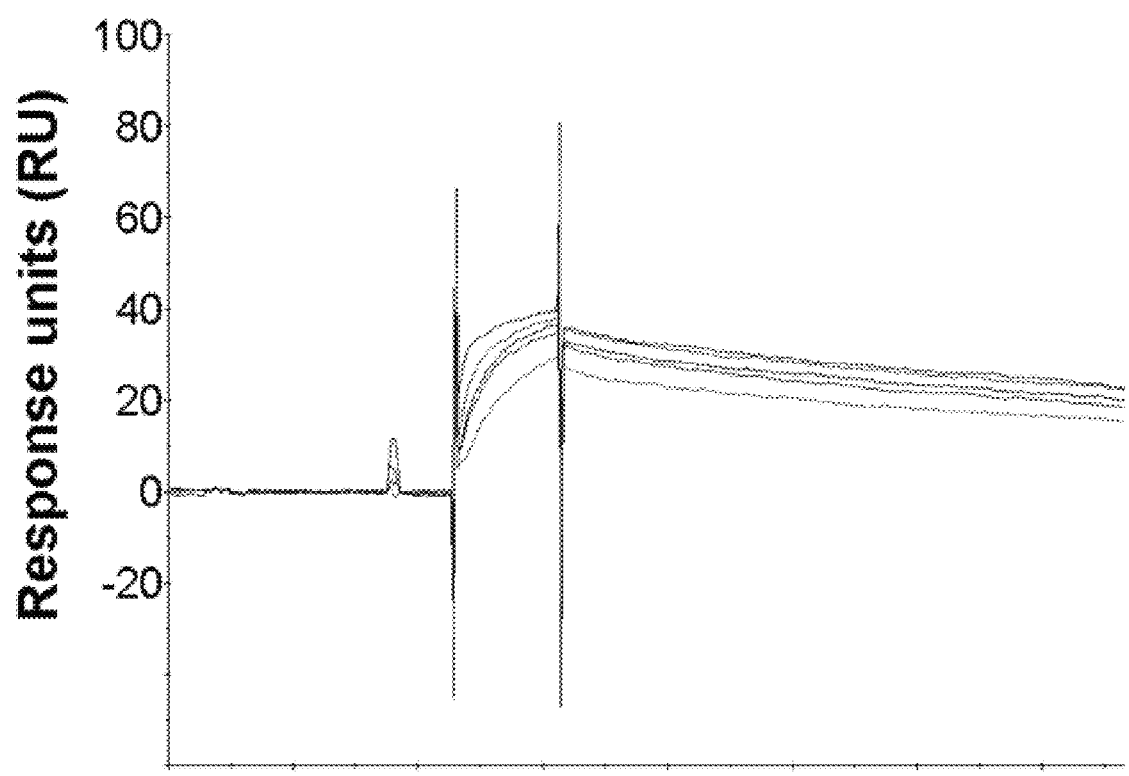
Figure 2D:
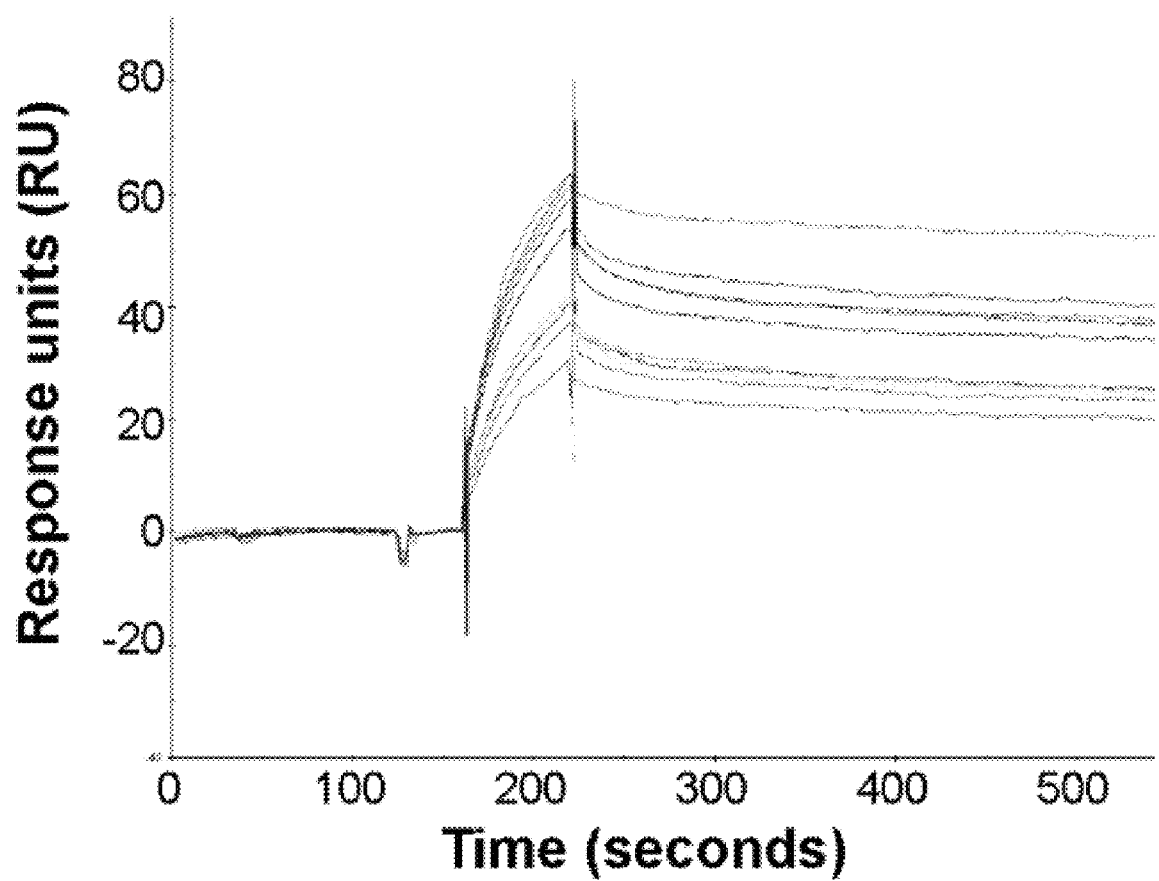

The invention provides for humanized antibodies capable of binding to pertussis toxin protein, nucleic acids encoding the provided humanized antibodies, pharmaceutical compositions including the provided humanized antibodies and methods of treating whooping caught using the provided humanized antibodies. The invention further provides for a pertussis toxin protein S1-S4 conjugate, vaccines including the provided S1-S4 conjugate and methods of immunizing using the provided S1-S4 conjugate.

I. Definitions

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to V$_H$-C$_{H1}$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., pp. 77-96 in Monoclonal Antibodies and Cancer Therapy (1985)). "Monoclonal" antibodies (mAb) refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348: 552-554 (1990); Marks et al., Biotechnology 10:779-783 (1992)).

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

A "ligand" refers to an agent, e.g., a polypeptide or other molecule, capable of binding to a receptor.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length. The present invention includes polypeptides that are substantially identical to any of SEQ ID NOs:1, 3-13, 57, 58, and 59. The present invention also includes polynucleotides that are substantially identical to any of SEQ ID NOs:2, and 14-54.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (on the World Wide Web at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLO-SUM62 scoring matrix (see Henikoff and Henikoff (1989) *Proc. Natl. Acad. Sci. USA* 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

An amino acid residue in an antibody "corresponds" to a given residue when it occupies the same essential structural position within the antibody as the given residue. For example, a selected residue in a comparison antibody corresponds to position 97 (according to the Kabat numbering system as described herein) in an antibody provided herein when the selected residue occupies the same essential spatial or structural relationship to Kabat position 97 as assessed using applicable methods in the art. For example, a comparison antibody may be aligned for maximum sequence homology with the antibody provided herein and the position in the aligned comparison antibody that aligns with Kabat position 97 may be determined to correspond to it. Alternatively, instead of (or in addition to) a primary sequence alignment as described above, a three dimensional structural alignment can also be used, e.g., where the structure of the comparison antibody is aligned for maximum correspondence with an antibody provided herein and the overall structures compared. In this case, an amino acid that occupies the same essential position as Kabat position 97 in the structural model may be said to correspond.

The term "isolated," when applied to a protein, denotes that the protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. The term "purified" denotes that a protein gives rise to essentially one band in an electrophoretic gel. Particularly, it means that the protein is at least 85% pure, more preferably at least 95% pure, and most preferably at least 99% pure.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Typically a specific or selective reaction will be at least twice background signal or noise and more typically more than 10 to 100 times background.

An "immunogenic agent" or "immunogen" is capable of inducing an immunological response against itself on administration to a mammal, optionally in conjunction with an adjuvant. Examples for an immunogen are the pertussis toxin protein S1-S4 conjugates as provided herein. Immunogenic agents can be linked to carriers by chemical crosslinking Techniques for linking an immunogen to a carrier include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. A variety of such disulfide/amide-forming agents are described by *Immun. Rev.* 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt.

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

The compositions can be administered for therapeutic or prophylactic treatments. In therapeutic applications, compositions are administered to a patient suffering from a disease (e.g., whooping cough) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

The compositions provided herein, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

The combined administrations contemplates coadministration, using separate formulations or a single pharmaceutical formulation, and consecutive administration in either order, wherein preferably there is a time period while both (or all) active agents simultaneously exert their biological activities.

Effective doses of the compositions provided herein vary depending upon many different factors, including means of administration, target site, physiological state of the patient, whether the patient is human or an animal, other medications administered, and whether treatment is prophylactic or therapeutic. However, a person of ordinary skill in the art would immediately recognize appropriate and/or equivalent doses looking at dosages of approved compositions for treating and preventing whopping cough for guidance.

II. Humanized Antibodies

A humanized antibody is a genetically engineered antibody in which at least one CDR (or functional fragment thereof) from a mouse antibody ("donor antibody", which can also be rat, hamster or other non-human species) are grafted onto a human antibody ("acceptor antibody"). In some embodiments, more than one mouse CDR is grafted (e.g. all six mouse CDRs are grafted). The sequence of the acceptor antibody can be, for example, a mature human antibody sequence (or fragment thereof), a consensus sequence of a human antibody sequence (or fragment thereof), or a germline region sequence (or fragment thereof). Thus, a humanized antibody may be an antibody having one or more CDRs from a donor antibody and variable region framework (FR). The FR may form part of a constant region within a human antibody. In addition, in order to retain high binding affinity, amino acids in the human acceptor sequence may be replaced by the corresponding amino acids from the donor sequence, for example where: (1) the amino acid is in a CDR; (2) the amino acid is in the human framework region(e.g. the amino acid is immediately adjacent to one of the CDR's). See, U.S. Pat. Nos. 5,530,101 and 5,585,089, incorporated herein by reference, which provide detailed instructions for construction of humanized antibodies. Although humanized antibodies often incorporate all six CDRs (e.g. as defined by Kabat, but often also including hypervariable loop H1 as defined by Chothia) from a mouse antibody, they can also be made with fewer mouse CDRs and/or less than the complete mouse CDR sequence (e.g. a functional fragment of a CDR) (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

Thus, in some embodiments it is necessary to incorporate only part of the donor CDRs, namely the subset of CDR residues required for binding, termed the SDRs, into the humanized antibody. Donor CDR residues not contacting antigen and not in the SDRs can be identified based on previous studies (for example residues H60-H65 (Kabat numbering system) in mouse CDR H2 are often not required), from regions of Kabat CDRs lying outside Chothia hypervariable loops (Chothia, J. Mol. Biol. 196:901, 1987), by molecular modeling and/or empirically, or as described in Gonzales et al., Mol. Immunol. 41: 863, 2004. In such humanized antibodies at positions in which one or more donor CDR residues is absent, the amino acid occupying the position can be an amino acid occupying the corresponding position (by Kabat numbering) in the acceptor antibody sequence. The number of such substitutions of acceptor amino acids for donor amino acids in a donor CDR may reflect a balance of competing considerations.

Typically a humanized antibody as provided herein may include (i) a light chain comprising at least one CDR (often three CDRs) from a mouse antibody (also referred to herein as a mouse CDR) and a human variable region framework; and (ii) a heavy chain comprising at least one CDR (often three CDRs) from the mouse antibody and a human variable region framework (FR). The light and heavy chain variable region frameworks (FRs) may each be a mature human antibody variable region framework sequence (or fragment thereof), a germline variable region framework sequence (combined with a J region sequence) (or fragment thereof), or a consensus sequence of a human antibody variable region framework sequence (or fragment thereof). In some embodiments, the humanized antibody includes a light chain as described in (i), a heavy chain as described in (ii) together with a light chain human constant region and a heavy chain constant region.

A chimeric antibody is an antibody in which the variable region of a mouse (or other rodent) antibody is combined with the constant region of a human antibody; their construction by means of genetic engineering is well-known. Such antibodies retain the binding specificity of the mouse antibody, while being about two-thirds human. The proportion of nonhuman sequence present in mouse, chimeric and humanized antibodies suggests that the immunogenicity of chimeric antibodies is intermediate between mouse and humanized antibodies. Other types of genetically engineered antibodies that may have reduced immunogenicity relative to mouse antibodies include human antibodies made using phage display methods (Dower et al., WO91/17271; McCafferty et al., WO92/001047; Winter, WO92/20791; and Winter, FEBS Lett. 23:92, 1998, each of which is incorporated herein by reference) or using transgenic animals (Lonberg et al., WO93/12227; Kucherlapati WO91/10741, each of which is incorporated herein by reference).

Other approaches to design humanized antibodies may also be used to achieve the same result as the methods in U.S. Pat. Nos. 5,530,101 and 5,585,089 described above, for example, "superhumanization" (see Tan et al. J. Immunol. 169: 1119, 2002, and U.S. Pat. No. 6,881,557) or the method of Studnicak et al., Protein Eng. 7:805, 1994. Moreover, other approaches to produce genetically engineered, reduced-immunogenicity mAbs include "reshaping", "hyperchimerization" and veneering/resurfacing, as described, e.g., in Vaswami et al., Annals of Allergy, Asthma and Immunology 81:105, 1998; Roguska et al. Protein Eng. 9:895, 1996; and U.S. Pat. Nos. 6,072,035 and 5,639,641.

In one aspect a humanized antibody capable of binding a pertussis toxin protein is provided. The humanized antibody includes a humanized heavy chain and a humanized light chain. As described above the variable regions of the heavy chain and the light chain of an antibody include complementarity determining regions (CDRs). CDRs are defined as regions within an antibody that are directly involved in antigen binding. Proceeding from the amino-terminus, these regions are designated CDR H1, CDR H2 and CDR H3 for the heavy chain, and CDR L1, CDR L2, and CDR L3 for the light chain, respectively. The CDRs are held in place by more conserved framework regions (FRs). Proceeding from the amino-terminus, these regions are designated FR H1, FR H2, FR H3, and FR H4 for the heavy chain and FR L1, FR L2, FR L3, and FR L4, for the light chain, respectively. For humanized antibodies, one or more of the CDRs are derived from a donor antibody (also referred to herein as a donor CDR, such as a mouse CDR), whereas the FRs are of human origin. The locations of CDR and FR regions and a numbering system have been defined by, e.g., Kabat et al. (Kabat et al., Sequences of Proteins of Immunological Interest, Fifth Edition, U.S. Department of Health and Human Services, U.S. Government Printing Office (1991)).

The humanized antibodies provided herein include at least one mouse CDR or a functional fragment thereof. A functional fragment of a CDR is a portion of a complete CDR amino acid sequence that is capable of binding to an antigen. Thus, a functional fragment of a CDR typically includes the amino acid residues required for CDR binding to the antigen. A "mouse CDR" is a complete CDR amino acid sequence or a functional fragment thereof derived from a mouse antibody that is capable of binding pertussis toxin protein. Thus, a functional fragment of a mouse CDR typically includes the amino acid residues required for CDR binding to pertussis toxin protein. Where a humanized antibody includes at least one mouse CDR, the at least one mouse CDR or a functional fragment thereof is derived from a donor antibody. A person of skill in the art will immediately recognize that a humanized antibody including at least one mouse CDR is a humanized antibody with at least one mouse CDR derived from a donor antibody and additional CDRs derived from the acceptor antibody (e.g. where the light chain includes a total of three CDRs and the heavy chain includes a total of three CDRs).

In some embodiments, the humanized heavy chain and the humanized light chain include combined one mouse CDR or functional fragment of a mouse CDR. Thus, in some embodiments, the humanized heavy chain and the humanized light chain include a combined 6 CDRs wherein at least one of the 6 CDRs is a mouse CDR. Where the humanized heavy chain and the humanized light chain include combined one mouse CDR, the humanized heavy chain or the humanized light chain include one mouse CDR. For example, a humanized antibody may include CDR H3 derived from the donor antibody (e.g. mouse, also referred to herein as a mouse CDR H3) and CDR H1, CDR H2, CDR L1, CDR L2, and CDR L3 derived from the acceptor antibody (i.e. human).

In other embodiments, the humanized heavy chain and the humanized light chain include combined two mouse CDRs. Where the humanized heavy chain and the humanized light chain include combined two mouse CDRs, the humanized heavy chain and the humanized light chain each include one mouse CDR (i), the humanized heavy chain includes two mouse CDRs (ii), or the humanized light chain includes two mouse CDRs (iii). For example, a humanized antibody may include CDR H3 and CDR L3 derived from the donor antibody (also referred to herein as a mouse CDR H3, mouse CDR L3, and mouse CDR H2 respectively), such as a mouse CDR and CDR H1, CDR H2, CDR L1, and CDR L2 derived from the acceptor antibody (i.e. human).

In other embodiments, the humanized heavy chain and the humanized light chain include combined three mouse CDRs. Where the humanized heavy chain and the humanized light chain include combined three mouse CDRs, the humanized heavy chain may include one mouse CDR and the humanized light chain may include two mouse CDRs (i), the humanized heavy chain includes two mouse CDRs and the humanized light chain includes one mouse CDR (ii), the humanized heavy chain includes three mouse CDRs (iii), or the humanized light chain includes three mouse CDRs (vi). For example, a humanized antibody may include CDR H3, CDR L3 and CDR H2 derived from the donor antibody (e.g. mouse, also referred to herein as a CDR H3, mouse CDR L3, and mouse CDR H2 respectively) and CDR H1, CDR L1, and CDR L2 derived from the acceptor antibody (i.e. human).

In some embodiments, the humanized heavy chain and the humanized light chain include combined four mouse CDRs. Where the humanized heavy chain and the humanized light chain include combined four mouse CDRs, the humanized heavy chain includes one mouse CDR and the humanized light chain includes three mouse CDRs (i), the humanized heavy chain includes three mouse CDRs and the humanized light chain includes one mouse CDR (ii), or the humanized heavy chain includes two mouse CDRs and the humanized light chain includes two mouse CDRs (iii). For example, a humanized antibody may include CDR H3, CDR L3, CDR H2 and CDR H1 derived from the donor antibody (e.g. mouse, also referred to herein as a mouse CDR H3, mouse CDR L3, mouse CDR H2 and mouse CDR H1 respectively) and CDR L1 and CDR L2 derived from the acceptor antibody (i.e. human).

In some embodiments, the humanized heavy chain and the humanized light chain each include at least one mouse CDR. Where the humanized heavy chain and the humanized light chain each include at least one mouse CDR, the humanized heavy chain includes at least one mouse CDR and the humanized light chain includes at least one mouse CDR. Thus, in some embodiments, the humanized heavy chain includes mouse CDR H1 and the humanized light chain includes mouse CDR L1. In some embodiments, mouse CDR H1 includes the amino acid sequence of SEQ ID NO:6 and mouse CDR L1 includes the amino acid sequence of SEQ ID NO:3. In some embodiments, mouse CDR H1 is the amino acid sequence of SEQ ID NO:6 and mouse CDR L1 is the amino acid sequence of SEQ ID NO:3. In other embodiments, the humanized heavy chain includes mouse CDR H2 and the humanized light chain includes mouse CDR L2. In some embodiments, mouse CDR H2 includes the amino acid sequence of SEQ ID NO:7 and mouse CDR L2 includes the amino acid sequence of SEQ ID NO:4. In other embodiments, mouse CDR H2 is the amino acid sequence of SEQ ID NO:7 and mouse CDR L2 is the amino acid sequence of SEQ ID NO:4. In some embodiments, the humanized heavy chain includes mouse CDR H3 and the humanized light chain includes mouse CDR L3. In some embodiments, mouse CDR H3 includes the amino acid sequence of SEQ ID NO:8 and mouse CDR L3 includes the amino acid sequence of SEQ ID NO:5. In other embodiments, CDR H3 is the amino acid sequence of SEQ ID NO:8 and mouse CDR L3 is the amino acid sequence of SEQ ID NO:5.

In some embodiments, the presence of mouse CDR H3 and mouse CDR L3 may be sufficient for binding of a humanized antibody to a pertussis toxin protein. Thus, in some embodiments, the humanized antibody does not include mouse CDR H1, mouse CDR H2, CDR L1 or mouse CDR L2. Where the humanized antibody does not include mouse CDR H1, mouse CDR H2, mouse CDR L1 or mouse CDR L2, the humanized antibody includes CDR H1, CDR H2, CDR L1 or CDR L2 derived from the acceptor antibody (i.e. human). Thus, a humanized antibody that does not include mouse CDR H1, mouse CDR H2, mouse CDR L1 or mouse CDR L2, does not include CDR H1, CDR H2, CDR L1 or CDR L2 from a donor antibody (e.g. mouse, rat, rabbit), but includes CDR H1, CDR H2, CDR L1 or CDR L2 from the acceptor antibody (i.e. human). Thus, in some embodiments the humanized heavy chain does not include mouse CDR H1 or mouse CDR H2 and the humanized light chain does not include mouse CDR L1 or mouse CDR L2. In other embodiments, the humanized heavy chain does not include mouse CDR H1 and mouse CDR H2 and the humanized light chain does not include mouse CDR L1 and mouse CDR L2.

In other embodiments, the humanized heavy chain includes mouse CDR H2 and mouse CDR H3 and the humanized light chain includes mouse CDR L2 and mouse CDR L3. In some embodiments, the humanized heavy chain includes mouse CDR H1, mouse CDR H2 and mouse CDR H3 and the humanized light chain includes mouse CDR L1, mouse CDR L2 and mouse CDR L3. In some embodiments, the humanized heavy chain includes mouse CDR H1 as set forth in SEQ ID NO:6, mouse CDR H2 as set forth in SEQ ID NO:7 and mouse CDR H3 as set forth in SEQ ID NO:8, and the humanized light chain includes mouse CDR L1 as set forth in SEQ ID NO:3, mouse CDR L2 as set forth in SEQ ID NO:4, and mouse CDR L3 as set forth in SEQ ID NO:5.

As described above, it may be necessary to incorporate only functional fragments of CDRs into the humanized antibody. A functional fragment of a CDR may be a part of a CDR or a subset of on one or more CDR residues required for binding. Thus, the humanized heavy chain and humanized light chain may include only certain residues of a donor antibody CDR (e.g. a mouse CDR). Where the humanized heavy chain and the humanized light chain include only certain residues of a donor antibody CDR, these donor antibody CDR residues are part of a corresponding acceptor antibody CDR. For example, a CDR H3 of a humanized antibody may contain one or more residues derived from a donor antibody CDR H3 (e.g. mouse) residing within the acceptor antibody CDR H3. Therefore, the CDR H3 of this humanized antibody includes one or more mouse CDR H3 residues residing within an acceptor antibody CDR H3. The one or more mouse CDR residues required for binding of a humanized antibody may be part of a single CDR within the humanized antibody (e.g. CDR H3, CDR H2, CDR H1, CDR L3, CDR L2, CDR L1). For example, the one or more mouse CDR residues required for binding of a humanized antibody may be part of CDR H3 within the humanized antibody. Alternatively, the one or more mouse CDR residues required for binding of a humanized antibody may be part of multiple CDRs within the humanized antibody. For example, the one or more mouse CDR residues may reside within CDR H3 and CDR L3 within a humanized antibody.

The position of CDRs and FRs may be defined by the Kabat numbering system (Kabat et al., Sequences of Proteins of Immunological Interest, Fifth Edition, U.S. Department of Health and Human Services, U.S. Government Printing Office (1991)). Likewise, the positions occupied by individual residues within the heavy or the light chain of an antibody may be defined by the Kabat numbering system. Therefore, the location of residues required for binding within a humanized heavy chain and a humanized light chain of a humanized antibody may be defined by the position of the residue according to the Kabat numbering system as is well known in the art. Thus, in some embodiments, the humanized heavy chain includes a serine at a position corresponding to Kabat position 97. In some embodiments, the humanized heavy chain includes a serine at position 97 of SEQ ID NO:58. In other embodiments, the humanized light chain includes a tryptophan at a position corresponding to Kabat position 91. In other embodiments, the humanized light chain includes a tryptophan at position 91 of SEQ ID NO:57. In other embodiments, the humanized light chain includes a histidine at a position corresponding to Kabat position 94. In other embodiments, the humanized light chain includes a histidine at position 94 of SEQ ID NO:57. In other embodiments, the humanized heavy chain includes an asparagine at a position corresponding to Kabat position 58. In other embodiments, the humanized heavy chain includes an asparagine at position 58 of SEQ ID NO:58. In other embodiments, the humanized heavy chain includes a tryptophan at a position corresponding to Kabat position 33. In other embodiments, the humanized heavy chain includes a tryptophan at position 33 of SEQ ID NO:58. In some embodiments, the humanized light chain includes a phenylalanine at a position corresponding to Kabat position 31. In some embodiments, the humanized light chain includes a phenylalanine at position 31 of SEQ ID NO:57.

In some embodiments, the humanized heavy chain includes a serine at a position corresponding to Kabat position 97. In a further embodiment, the humanized heavy chain includes a serine at position 97 of SEQ ID NO:58. In some further embodiments, the humanized light chain includes a tryptophan at a position corresponding to Kabat position 91. In some further embodiments, the humanized light chain includes a tryptophan at position 91 of SEQ ID NO:57. In still some further embodiments, the humanized light chain includes a histidine at a position corresponding to Kabat position 94. In some further embodiments, the humanized light chain includes a histidine at position 94 of SEQ ID NO:57. In a further embodiments, the humanized heavy chain includes an asparagine at a position corresponding to Kabat position 58. In a further embodiments, the humanized heavy chain includes an asparagine at position 58 of SEQ ID NO:58. In still a further embodiments, the humanized heavy chain includes a tryptophan at a position corresponding to Kabat position 33. In a further embodiments, the humanized heavy chain includes a tryptophan at position 33 of SEQ ID NO:58. In a further embodiments, the humanized light chain includes a phenylalanine at a position corresponding to Kabat position 31. In still a further embodiment, the humanized light chain includes a phenylalanine at position 31 of SEQ ID NO:57.

As described above, a humanized antibody may be an antibody having CDRs from a donor antibody (e.g. mouse) and variable region framework (FR) from a human antibody. The framework regions (FRs) are said to hold the CDRs in place in a humanized antibody. Proceeding from the amino-terminus, these regions are designated FR H1, FR H2, FR H3, and FR H4 for the heavy chain and FR L1, FR L2, FR L3, and FR L4, for the light chain, respectively. Surprisingly, the present invention provides for humanized antibodies that include one or more residues within the framework regions that are important for epitope binding of the humanized antibody. A framework region residue involved in (or important for) epitope binding (e.g. pertussis toxin protein binding such as S1-S4 binding) is referred to herein as a binding framework region residue. The binding framework region residues may reside in the framework region of a humanized heavy chain (i.e. FR H1, FR H2, FR H3, FR H4) or they may reside in the framework of a humanized light chain (i.e. FR L1, FR L2, FR L3, FR L4). A binding framework residue residing in the FR L3 region of a humanized light chain is referred to herein as a FR L3 binding framework region residue. Thus, a binding framework region residue residing in the FR H3 region of a humanized heavy chain is referred to herein as a FR H3 binding framework region residue.

In some embodiments, the humanized antibody includes at least one binding framework region residue. In some embodiments, the humanized heavy chain includes at least one binding framework region residue. In some embodiments, the humanized heavy chain includes one or more FR H3 binding framework region residues. In other embodiments, the humanized heavy chain includes one or more FR H2 binding framework region residues. In some embodiments, the humanized light chain includes at least one binding framework region residue. In some embodiments, the humanized light chain includes one or more FR L3 binding framework region residues. In other embodiments, the humanized light chain includes one or more FR L1 binding framework region residues.

In some embodiments, the humanized heavy chain includes at least one binding framework region residue and the humanized light chain includes at least one binding framework region residue. In some embodiments, the humanized light chain includes at least one FR H3 binding framework region residue and the humanized light chain includes at least one FR L3 binding framework region residue. In further embodiments, the humanized light chain includes at least one FR H3 binding framework region residue and at least one FR H2 binding framework region residue, and the humanized light chain includes at least one FR L3 binding framework region residue and at least one FR L1 binding framework region residue. The position of a binding framework region residue within a humanized antibody may be defined by the Kabat numbering system similar to the positions CDR residues. Thus, in some embodiments, the humanized light chain includes a cysteine at a position corresponding to Kabat position 23. In some embodiments, the humanized light chain includes a cysteine at position 23 of SEQ ID NO:57. In other embodiments, the humanized light chain includes a binding framework region residue that is a cysteine at a position corresponding to Kabat position 23. In other embodiments, the humanized light chain includes a phenylalanine at a position corresponding to Kabat position 65. In other embodiments, the humanized light chain includes a phenylalanine at position 65 of SEQ ID NO:57. In other embodiments, the humanized light chain includes a binding framework region residue that is a phenylalanine at a position corresponding to Kabat position 65. In some embodiments, the humanized light chain includes a tyrosine at a position corresponding to Kabat position 71. In some embodiments, the humanized light chain includes a tyrosine at position 71 of SEQ ID NO:57. In other embodiments, the humanized light chain includes a binding framework region residue that is a tyrosine at a position corresponding to Kabat position 71. In other embodiments, the humanized heavy chain includes a glycine at a position corresponding to Kabat position 49. In other embodiments, the humanized heavy chain includes a glycine at position 49 of SEQ ID NO:58. In other embodiments, the humanized heavy chain includes a binding framework region residue that is a glycine at a position corresponding to Kabat position 49. In some embodiments, the humanized heavy chain includes a serine at a position corresponding to Kabat position 65. In some embodiments, the humanized heavy chain includes a serine at position 65 of SEQ ID NO:58. In other embodiments, the humanized heavy chain includes a binding framework region residue that is a serine at a position corresponding to Kabat position 65. In other embodiments, the humanized heavy chain further includes a valine at a position corresponding to Kabat position 71. In other embodiments, the humanized heavy chain further includes a valine at a position corresponding to Kabat position 71 of SEQ ID NO:58. In other embodiments, the humanized heavy chain includes a binding framework region residue that is a valine at a position corresponding to Kabat position 71. In other embodiments, the humanized heavy chain includes a threonine at a position corresponding to Kabat position 73. In other embodiments, the humanized heavy chain includes a threonine at position 73 of SEQ ID NO:58. In other embodiments, the humanized heavy chain includes a binding framework region residue that is a threonine at a position corresponding to Kabat position 73. In some embodiments, the humanized heavy chain further includes a alanine at a position corresponding to Kabat position 78. In some embodiments, the humanized heavy chain further includes a alanine at position 78 of SEQ ID NO:58. In other embodiments, the humanized heavy chain includes a binding framework region residue that is a alanine at a position corresponding to Kabat position 78. In some embodiments, the humanized heavy chain includes a threonine at a position corresponding to Kabat position 93. In some embodiments, the humanized heavy chain includes a threonine at position 93 of SEQ ID NO:58. In other embodiments, the humanized heavy chain includes a binding framework region residue that is a threonine at a position corresponding to Kabat position 93.

In other embodiments, the humanized light chain includes a cysteine at a position corresponding to Kabat position 23. In a further embodiment, the humanized light chain includes a binding framework region residue that is a cysteine at a position corresponding to Kabat position 23. In a further embodiment, the humanized light chain includes a phenylalanine at a position corresponding to Kabat position 65. In a further embodiment, the humanized light chain includes a binding framework region residue that is a phenylalanine at a position corresponding to Kabat position 65. In still a further embodiment, the humanized light chain includes a tyrosine at a position corresponding to Kabat position 71. In a further embodiment, the humanized light chain includes a binding framework region residue that is a tyrosine at a position corresponding to Kabat position 71. In a further embodiment, the humanized heavy chain includes a glycine at a position corresponding to Kabat position 49. In a further embodiment, the humanized heavy chain includes a binding framework region residue that is a glycine at a position corresponding to Kabat position 49. In a further embodiment, the humanized heavy chain includes a serine at a position corresponding to Kabat position 65. in a further embodiment, the humanized heavy chain includes a binding framework region residue that is a serine at a position corresponding to Kabat position 65. In still a further embodiment, the humanized heavy chain further includes a valine at a position corresponding to Kabat position 71. In a further embodiment, the humanized heavy chain includes a binding framework region residue that is a valine at a position corresponding to Kabat position 71. In a further embodiment, the humanized heavy chain includes a threonine at a position corresponding to Kabat position 73. In a further embodiment, the humanized heavy chain includes a binding framework region residue that is a threonine at a position corresponding to Kabat position 73. In a further embodiment, the humanized heavy chain further includes a alanine at a position corresponding to Kabat position 78. In a further embodiment, the humanized heavy chain includes a binding framework region residue that is a alanine at a position corresponding to Kabat position 78. In still a further embodiment, the humanized heavy chain includes a threonine at a position corresponding to Kabat position 93. In a further embodiment, the humanized heavy chain includes a binding framework region residue that is a threonine at a position corresponding to Kabat position 93.

The humanized antibodies as provided herein may be Fab' fragments. Where the humanized antibodies are Fab' fragments, the humanized antibodies include a humanized heavy chain (e.g. including a constant and a variable region) and a humanized light chain (e.g. including a constant and a variable region). In some embodiments, the humanized antibody is a Fab' fragment. In other embodiments, the humanized antibody includes a human constant region. In other embodiments, the humanized antibody is an IgG. In other embodiments, the humanized antibody is an IgA. In other embodiments, the humanized antibody is an IgM. In some embodiments, the humanized antibody includes the amino acid sequence of SEQ ID NO:1.

In other embodiments, the humanized antibody is a single chain antibody. A single chain antibody includes a variable light chain and a variable heavy chain. A person of skill in the art will immediately recognize that a single chain antibody includes a single light chain and a single heavy chain, in contrast to a immunoglobulin antibody, which includes two identical pairs of polypeptide chains, each pair having one light chain and one heavy chain. Each light chain and heavy chain in turn consists of two regions: a variable ("V") region (i.e. variable light chain and variable heavy chain) involved in binding the target antigen, and a constant ("C") region that interacts with other components of the immune system. The variable light chain and the variable heavy chain in a single chain antibody may be linked through a linker peptide. Examples for linker peptides of single chain antibodies are described in Bird, R. E., Hardman, K. D., Jacobson, J. W., Johnson, S., Kaufman, B. M., Lee, S. M., Lee, T., Pope, S. H., Riordan, G. S, and Whitlow, M. (1988). An example for an amino acid sequence of a humanized single chain antibody including linker residues is set forth in SEQ ID NO:1. A person of skill in the art will immediately recognize that residue 1-113 correspond to the variable light chain of SEQ ID NO:57, followed by 13 linker residues and the variable heavy chain as set forth in SEQ ID NO:58. Single-chain antigen-binding proteins. *Science* 242, 423-6. Methods of making scFv antibodies have been described. See, Huse et al., *Science* 246:1275-1281 (1989); Ward et al., *Nature* 341:544-546 (1989); and Vaughan et al., *Nature Biotech.* 14:309-314 (1996). Briefly, mRNA from B-cells from an immunized animal is isolated and cDNA is prepared. The cDNA is amplified using primers specific for the variable regions of heavy and light chains of immunoglobulins. The PCR products are purified and the nucleic acid sequences are joined. If a linker peptide is desired, nucleic acid sequences that encode the peptide are inserted between the heavy and light chain nucleic acid sequences. The nucleic acid which encodes the scFv is inserted into a vector and expressed in the appropriate host cell.

The ability of an antibody to bind a specific epitope can be described by the equilibrium dissociation constant ($K_D$). The equilibrium dissociation constant ($K_D$) as defined herein is the ratio of the dissociation rate (K-off) and the association rate (K-on) of a humanized antibody to a pertussis toxin protein. It is described the following formula: $K_D$=K-off/K-on. In some embodiments, the humanized antibody is capable of binding a pertussis toxin protein with an equilibrium dissociation constant ($K_D$) of about 100 nM. In some embodiments, the humanized antibody is capable of binding a pertussis toxin protein with an equilibrium dissociation constant ($K_D$) of about 90 nM. In some embodiments, the humanized antibody is capable of binding a pertussis toxin protein with an equilibrium dissociation constant ($K_D$) of about 80 nM. In some embodiments, the humanized antibody is capable of binding a pertussis toxin protein with an equilibrium dissociation constant ($K_D$) of about 70 nM. In some embodiments, the humanized antibody is capable of binding a pertussis toxin protein with an equilibrium dissociation constant ($K_D$) of about 60 nM. In some embodiments, the humanized antibody is capable of binding a pertussis toxin protein with an equilibrium dissociation constant ($K_D$) of about 50 nM. In some embodiments, the humanized antibody is capable of binding a pertussis toxin protein with an equilibrium dissociation constant ($K_D$) of about 40 nM. In some embodiments, the humanized antibody is capable of binding a pertussis toxin protein with an equilibrium dissociation constant ($K_D$) of about 30 nM. In some embodiments, the humanized antibody is capable of binding a pertussis toxin protein with an equilibrium dissociation constant ($K_D$) of about 20 nM. In some embodiments, the humanized antibody is capable of binding a pertussis toxin protein with an equilibrium dissociation constant ($K_D$) of about 10 nM. In some embodiments, the humanized antibody is capable of binding a pertussis toxin protein with an equilibrium dissociation constant ($K_D$) of about 9.5 nM. In some embodiments, the humanized antibody is capable of binding a pertussis toxin protein with an equilibrium dissociation constant ($K_D$) of about 9 nM. In some embodiments, the humanized antibody is capable of binding a pertussis toxin protein with an equilibrium dissociation constant ($K_D$) of about 8.5 nM. In some embodiments, the humanized antibody is capable of binding a pertussis toxin protein with an equilibrium dissociation constant ($K_D$) of about 8 nM. In some embodiments, the humanized antibody is capable of binding a pertussis toxin protein with an equilibrium dissociation constant ($K_D$) of about 7.5 nM. In some embodiments, the humanized antibody is capable of binding a pertussis toxin protein with an equilibrium dissociation constant ($K_D$) of about 7 nM. In some embodiments, the humanized antibody is capable of binding a pertussis toxin protein with an equilibrium dissociation constant ($K_D$) of about 6.5 nM. In some embodiments, the humanized antibody is capable of binding a pertussis toxin protein with an equilibrium dissociation constant ($K_D$) of about 6 nM. In some embodiments, the humanized antibody is capable of binding a pertussis toxin protein with an equilibrium dissociation constant ($K_D$) of about 5.5 nM. In some embodiments, the humanized antibody is capable of binding a pertussis toxin protein with an equilibrium dissociation constant ($K_D$) of about 5 nM. In some embodiments, the humanized antibody is capable of binding a pertussis toxin protein with an equilibrium dissociation constant ($K_D$) of about 4.5 nM. In some embodiments, the humanized antibody is capable of binding a pertussis toxin protein with an equilibrium dissociation constant ($K_D$) of about 4 nM. In some embodiments, the humanized antibody is capable of binding a pertussis toxin protein with an equilibrium dissociation constant ($K_D$) of about 3.5 nM. In some embodiments, the humanized antibody is capable of binding a pertussis toxin protein with an equilibrium dissociation constant ($K_D$) of about 3 nM. In some embodiments, the humanized antibody is capable of binding a pertussis toxin protein with an equilibrium dissociation constant ($K_D$) of about 2.5 nM. In some embodiments, the humanized antibody is capable of binding a pertussis toxin protein with an equilibrium dissociation constant ($K_D$) of about 2 nM.

In some embodiments, the humanized antibody is capable of binding a pertussis toxin protein with an equilibrium dissociation constant ($K_D$) of less than 10 nM. In some embodiments, the equilibrium dissociation constant ($K_D$) is less than 8 nM and more than 1 nM. In other embodiments, the equilibrium dissociation constant ($K_D$) is less than 6 nM and more than 1.25 nM. In other embodiments, the equilibrium dissociation constant ($K_D$) is less than 4 nM and more than 1.5 nM.

In some embodiments, the humanized antibody provided herein binds to a functional fragment of a pertussis toxin protein (e.g. pertussis toxin protein S1-S4 conjugate). In some embodiments, the humanized antibody is capable of binding a pertussis toxin protein S1-S4 conjugate with an equilibrium dissociation constant ($K_D$) of less than 10 nM. In some embodiments, the equilibrium dissociation constant ($K_D$) is less than 8 nM and more than 1 nM. In other embodiments, the equilibrium dissociation constant ($K_D$) is less than 6 nM and more than 1.25 nM. In other embodiments, the equilibrium dissociation constant ($K_D$) is less than 4 nM and more than 1 nM. In some embodiments, the equilibrium dissociation constant ($K_D$) is about 1.5 nM.

The humanized antibodies provided herein are capable of binding a pertussis toxin protein. In some embodiments, the humanized antibody provided herein is capable of neutralizing (or inhibitory or antagonizing) a pertussis toxin protein (i.e. binding so as to partially or completely inhibit one or more biological activities of a pertussis toxin protein). Among the biological activities of a pertussis toxin protein that a neutralizing antibody may inhibit or block is the ability of a pertussis toxin protein to bind cellular receptors. The receptor binding region of a pertussis toxin protein consists of four polypeptide subunits referred to as subunit S2, subunit S3, subunit S4 and subunit S5, respectively. Examples of cellular receptors that are bound by the subunits S2, S3, S4, and S5 of a pertussis toxin protein are members of the N-linked sialoglycoprotein family such as fetuin, haptoblobin, and transferrin. Another important activity of a pertussis toxin protein that may be inhibited by a neutralizing antibody is the enzymatic activity of the pertussis toxin protein as ADP ribosylase towards G proteins. The subunit conferring to the enzymatic activity as ADP-ribosylase in a pertussis toxin protein is subunit S1. In some embodiments, the pertussis toxin protein is a pertussis holotoxin. A pertussis holotoxin as referred to herein as a pertussis toxin protein that includes all five pertussis toxin protein subunits. In some embodiments, the pertussis toxin holo-protein consists of the polypeptides set forth in SEQ ID NO:9, 10, 11, 12, and 13. In other embodiments, the pertussis toxin protein is a truncated pertussis toxin protein. A truncated pertussis protein as referred to herein includes at least one of the pertussis toxin protein subunits (i.e. S1, S2, S3, S4 and S5). In some embodiments, the truncated pertussis toxin protein includes subunit S1. In other embodiments, the truncated pertussis toxin protein includes the amino acid sequence corresponding to amino acid residues 1 to 220 of SEQ ID NO:9. In other embodiments, the truncated pertussis toxin protein includes amino acid residues 1 to 220 of SEQ ID NO:9.

The ability of a particular antibody to recognize the same epitope as another antibody can be determined by the ability of one antibody to competitively inhibit binding of the second antibody to the antigen, e.g., to pertussis toxin protein or a truncated pertussis toxin protein. Any of a number of competitive binding assays can be used to measure competition between two antibodies to the same antigen. An exemplary assay is a Biacore® assay. Briefly, in these assays, binding sites can be mapped in structural terms by testing the ability of interactants, e.g. different antibodies, to inhibit the binding of another. Injecting two consecutive antibody samples in sufficient concentration can identify pairs of competing antibodies for the same binding epitope.

Other conventional immunoassays known in the art can be used in the present invention. For example, antibodies can be differentiated by the epitope to which they bind using a sandwich ELISA assay. This is carried out by using a capture antibody (e.g. a mouse 1B7 antibody) to coat the surface of a well. A sub-saturating concentration of tagged-antigen is then added to the capture surface. This protein will be bound to the antibody through a specific antibody:epitope interaction. After washing a second antibody (e.g. a humanized antibody capable of binding a pertussis toxin protein), which has been covalently linked to a detectable moiety (e.g., HRP, with the labeled antibody being defined as the detection antibody) is added to the ELISA. If this antibody recognizes the same epitope as the capture antibody it will be unable to bind to the target protein as that particular epitope will no longer be available for binding. If however this second antibody recognizes a different epitope on the target protein it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine epitope specificity.

In some embodiments, the humanized antibodies described herein compete with an antibody that is capable of binding a pertussis toxin protein. Where the humanized antibody competes with an antibody (competitor antibody) for binding a truncated pertussis toxin protein, the humanized antibody inhibits (completely or partially) binding of the competitor antibody to a measurable extend. The inhibition of binding may be measured by any of the methods described above. In general, a humanized antibody is considered to competitively inhibit binding of a competitor antibody (e.g. mouse 1B7), if binding of the competitor antibody to the antigen is reduced by at least 30%, usually at least about 40%, 50%, 60% or 75%, and often by at least about 90%, in the presence of the humanized antibody using any of the assays described above. In some embodiments, the humanized antibody is an antibody which competes with an antibody that is capable of binding a pertussis toxin protein including the amino acid sequence corresponding to amino acid residues 1 to 220 of SEQ ID NO:9. Thus, in some embodiments, the antibody provided herein binds to a pertussis toxin protein competitively with a mouse 1B7 antibody (Sato, H. and Y. Sato. 1990. Protective activities in mice of monoclonal antibodies against pertussis toxin. *Infect Immun.* 58: 3369-3374). In other embodiments, the antibody provided herein inhibits (completely or partially) the binding of a mouse 1B7 antibody. In some further embodiments, the antibody provided herein decreases the binding of a mouse 1B7 antibody in a competition assay by about 10%, 20%, 30%, 40%, 50%, 60%, 70%, 80%, 90% or 100%. In some further embodiments, the antibody provided herein decreases the binding of a mouse 1B7 antibody in a competition assay by at least about 10%, 20%, 30%, 40%, 50%, 60%, 70%, 80%, 90% or 100%.

In some embodiments, the humanized antibody is capable of binding a 1B7 footprint region. A 1B7 footprint region as referred to herein is the region on a pertussis toxin protein that is bound by a mouse 1B7 antibody (as described in detail herein—e.g. portions of the S1 and S4 domains of a pertussis toxin protein). Therefore, the humanized antibody capable of binding a 1B7 footprint region is an antibody which competes with a mouse 1B7 antibody for binding to the 1B7 footprint region. A 1B7 footprint region includes at least one residue required for binding a humanized antibody. In some embodiments, the 1B7 footprint region includes an arginine at a position corresponding to position 79 of SEQ ID NO:9. In some embodiments, the 1B7 footprint region includes a histidine at a position corresponding to position 83 of SEQ ID NO:9. In other embodiments, the 1B7 footprint region includes an arginine at a position corresponding to position 93 of SEQ ID NO:9. In other embodiments, the 1B7 footprint region includes a tyrosine at a position corresponding to position 148 of SEQ ID NO:9. In some embodiments, the 1B7 footprint region includes an asparagine at a position corresponding to position 150 of SEQ ID NO:9. In some embodiments, the 1B7 footprint region includes a threonine at a position corresponding to position 153 of SEQ ID NO:9.

In some embodiments, the 1B7 footprint region includes an arginine at a position corresponding to position 79 of SEQ ID NO:9. In a further embodiment, the 1B7 footprint region includes a histidine at a position corresponding to position 83 of SEQ ID NO:9. In still a further embodiment, the 1B7 footprint region includes an arginine at a position corresponding to position 93 of SEQ ID NO:9. In a further embodiment, the 1B7 footprint region includes a tyrosine at a position corresponding to position 148 of SEQ ID NO:9. In still a further embodiment, the 1B7 footprint region includes an asparagine at a position corresponding to position 150 of SEQ ID NO:9. In a further embodiment, the 1B7 footprint region includes a threonine at a position corresponding to position 153 of SEQ ID NO:9. In some embodiments, the 1B7 footprint region includes the amino acid sequence in SEQ ID NO:9.

III. Nucleic Acids

In one aspect, an isolated nucleic acid encoding a humanized antibody capable of binding a pertussis toxin protein is provided. The antibody includes a humanized heavy chain and a humanized light chain. The humanized antibody enocoded by the isolatated nucleic acids are described in detail through this application (including the description above and in the examples section). Thus, the humanized antibody enocoded by the isolatated nucleic acids include all of the embodiments described herein. For example, the nucleic acid may encode at least one CDR, specific residues involved in binding the epitope, or binding framework residues. For instance, the nucleic acid may encode a humanized heavy chain including a serine at a position corresponding to Kabat position 97. Thus, in some embodiments, the humanized includes a serine at a position corresponding to Kabat position 97. In some embodiments, the humanized antibody includes the amino acid sequence of SEQ ID NO:1.

IV. Pertussis Toxin Proteins

In another aspect, a pertussis toxin protein S1-S4 conjugate is provided. A pertussis toxin protein S1-S4 conjugate is a protein conjugate including a pertussis toxin protein subunit S1, a pertussis toxin protein subunit S4 or any functional fragments thereof. A pertussis toxin protein S1-S4 conjugate provided herein is a recombinant protein comprising a pertussis toxin protein subunit S1 or functional fragment thereof and a pertussis toxin protein subunit S4 or functional fragment thereof. The subunit S1 and subunit S4 or any functional fragments thereof may be part of one recombinant protein, or they can be part of a first and a second recombinant protein that are chemically linked together. Functional fragments of a pertussis toxin protein S1-S4 conjugate are regions of the pertussis toxin protein S1 subunit and S4 subunit that are involved in antibody binding (e.g. includes a 1B7 footprint region). Thus, the pertussis toxin protein S1-S4 conjugate my include (e.g. form) a 1B7 footprint region. In some embodiments, the conjugate or functional fragment thereof includes an arginine at a position corresponding to position 79 of SEQ ID NO:9. In other embodiments, the conjugate or functional fragment thereof includes a histidine at a position corresponding to position 83 of SEQ ID NO:9. In other embodiments, the conjugate or functional fragment thereof includes an arginine at a position corresponding to position 93 of SEQ ID NO:9. In other embodiments, the conjugate or functional fragment thereof includes a tyrosine at a position corresponding to position 148 of SEQ ID NO:9. In some embodiments, the conjugate or functional fragment thereof includes an asparagine at a position corresponding to position 150 of SEQ ID NO:9. In some embodiments, the conjugate or functional fragment thereof includes a threonine at a position corresponding to position 153 of SEQ ID NO:9. In other embodiments, the conjugate or functional fragment thereof includes the amino acid sequence in SEQ ID NO:9. In other embodiments, the conjugate or functional fragment thereof has the amino acid sequence in SEQ ID NO:9. In some embodiments, the conjugate or functional fragment thereof includes an alanine at a position corresponding to position 40 of SEQ ID NO:12. In other embodiments, the conjugate or functional fragment thereof includes a serine at a position corresponding to position 42 of SEQ ID NO:12. In other embodiments, the conjugate or functional fragment thereof includes a serine at a position corresponding to position 43 of SEQ ID NO:12. In other embodiments, the conjugate or functional fragment thereof includes the amino acid sequence in SEQ ID NO:12. In other embodiments, the conjugate or functional fragment thereof has the amino acid sequence of SEQ ID NO:12. In some embodiments, the conjugate or functional fragment thereof has an amino acid sequence of SEQ ID NO: 9 and SEQ ID NO:12. Where the S1-S4 conjugate or functional fragment thereof has an amino acid sequence of SEQ ID NO: 9 (or functional fragment thereof) and SEQ ID NO:12 (or functional fragment thereof), the amino acid sequences of SEQ ID NO:9 (or functional fragment thereof) and SEQ ID NO:12 (or functional fragment thereof) may be combined such that the resulting polypeptide includes SEQ ID NO:9 (or functional fragment thereof) on the amino terminal side of (e.g amino terminal to) SEQ ID NO:12 (or functional fragment thereof). In some related embodiments, the S1-S4 conjugate or functional fragment thereof that has an amino acid sequence of SEQ ID NO: 9 (or functional fragment thereof) and SEQ ID NO:12 (or functional fragment thereof) includes the 1B7 footprint region.

In some embodiments, the conjugate or functional fragment thereof includes an arginine at a position corresponding to position 79 of SEQ ID NO:9. In further embodiments, the conjugate or functional fragment thereof includes a histidine at a position corresponding to position 83 of SEQ ID NO:9. In a further embodiment, the conjugate or functional fragment thereof includes an arginine at a position corresponding to position 93 of SEQ ID NO:9. In still further embodiments, the conjugate or functional fragment thereof includes a tyrosine at a position corresponding to position 148 of SEQ ID NO:9. In further embodiments, the conjugate or functional fragment thereof includes an asparagine at a position corresponding to position 150 of SEQ ID NO:9. In still a further embodiment, the conjugate or functional fragment thereof includes a threonine at a position corresponding to position 153 of SEQ ID NO:9. In a further embodiment, the conjugate or functional fragment thereof includes an alanine at a position corresponding to position 40 of SEQ ID NO:12. In a further embodiment, the conjugate or functional fragment thereof includes a serine at a position corresponding to position 42 of SEQ ID NO:12. In still further embodiments, the conjugate or functional fragment thereof includes a serine at a position corresponding to position 43 of SEQ ID NO:12.

In some embodiments, the conjugate or functional fragment thereof does not include a S2 pertussis toxin protein subunit. In some embodiments, the conjugate or functional fragment thereof does not include a S3 pertussis toxin protein subunit. In some embodiments, the conjugate or functional fragment thereof does not include a S4 pertussis toxin protein subunit. In some embodiments, the conjugate or functional fragment thereof does not include a S2 pertussis toxin protein subunit, a S3 pertussis toxin protein subunit, or a S5 pertussis toxin protein subunit. In other embodiments, the conjugate or functional fragment thereof does not include a S2 pertussis toxin protein subunit, a S3 pertussis toxin protein subunit, and a S5 pertussis toxin protein subunit.

V. Vaccines And Methods Of Immunizing

In another aspect, a vaccine including a pertussis toxin protein S1-S4 conjugate or functional fragment thereof and a pharmaceutically acceptable excipient is provided. In some embodiments, the pertussis toxin protein S1-S4 conjugate or functional fragment thereof includes the amino acid sequence of SEQ ID NO:9 or a functional fragment thereof. In still a further embodiment, the pertussis toxin protein S1-S4 conjugate or functional fragment thereof includes the amino acid sequence of SEQ ID NO:12. In some embodiments, the pertussis toxin protein S1-S4 conjugate of functional fragment thereof has the amino acid sequence of SEQ ID NO:9 and SEQ ID NO:12. The pertussis toxin protein S1-S4 conjugates or functional fragment thereof for use in the methods of the invention are immunogenic peptides that upon administration to a human patient or animal generate antibodies that specifically bind to the 1B7 footprint region. Immunogenic peptides are capable of inducing an immunological response against itself on administration to a mammal, optionally in conjunction with an adjuvant.

In another aspect, a method for immunizing a host susceptible to a disease caused by *Bordetella pertussis* bacterium (e.g. whooping cough) is provided. The method includes administering a pertussis toxin protein S1-S4 conjugate (as described herein including embodiments thereof such as functional fragments) to the host under conditions such that antibodies directed to the pertussis toxin protein S1-S4 conjugate or a functional fragment thereof are produced. In some embodiments, the pertussis toxin protein S1-S4 conjugate forms part of the vaccine described herein. In some embodiments, the host is a human.

The S1-S4 conjugates or functional fragments thereof as provided herein may be formulated and introduced as a vaccine through oral, intradermal, intramuscular, intraperitoneal, intravenous, subcutaneous, intranasal, and via scarification (scratching through the top layers of skin, e.g., using a bifurcated needle) or any other standard route of immunization. Vaccine formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient or any other oral composition as listed above. Alternatively, the vaccines may be administered parenterally as injections (intravenous, intramuscular or subcutaneous). Alternatively, S1-S4 conjugates the present invention may be encapsulated in liposomes and administered via injection. Commercially available liposome delivery systems are available from Novavax, Inc. of Rockville, Md., commercially available under the name Novasomes™. These liposomes are specifically formulated for immunogen or antibody delivery. The amount of S1-S4 conjugates used in a vaccine can depend upon a variety of factors including the route of administration, species, and use of booster administration. However, a person of ordinary skill in the art would immediately recognize appropriate and/or equivalent doses looking at dosages of approved whopping cough vaccines for guidance.

The term "adjuvant" refers to a compound that when administered in conjunction with an antigen (e.g. pertussis toxin protein S1-S4 conjugate) augments the immune response to the antigen, but when administered alone does not generate an immune response to the antigen. Adjuvants can augment an immune response by several mechanisms including lymphocyte recruitment, stimulation of B and/or T cells, and stimulation of macrophages. The adjuvant increases the titer of induced antibodies and/or the binding affinity of induced antibodies relative to the situation if the immunogen were used alone. A variety of adjuvants can be used in combination with an pertussis toxin protein S1-S4 conjugate as provided herein, to elicit an immune response. Preferred adjuvants augment the intrinsic response to an immunogen without causing conformational changes in the immunogen that affect the qualitative form of the response. Preferred adjuvants include aluminum hydroxide and aluminum phosphate, 3 De-O-acylated monophosphoryl lipid A (MPL™) (see GB 2220211 (RIBI ImmunoChem Research Inc., Hamilton, Mont., now part of Corixa). Stimulon™ QS-21 is a triterpene glycoside or saponin isolated from the bark of the *Quillaja Saponaria* Molina tree found in South America (see Kensil et al., in *Vaccine Design: The Subunit and Adjuvant Approach* (eds. Powell & Newman, Plenum Press, NY, 1995); U.S. Pat. No. 5,057,540), (Aquila BioPharmaceuticals, Framingham, Mass.). Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)), pluronic polymers, and killed mycobacteria. Another adjuvant is CpG (WO 98/40100). Adjuvants can be administered as a component of a therapeutic composition with an active agent or can be administered separately, before, concurrently with, or after administration of the therapeutic agent.

Other examples of adjuvants are aluminum salts (alum), such as alum hydroxide, alum phosphate, alum sulfate. Such adjuvants can be used with or without other specific immunostimulating agents such as MPL or 3-DMP, QS-21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2' dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi ImmunoChem, Hamilton, Mont.) containing 2% squalene, 0.2% Tween 80, and one or more bacterial cell wall components from the group consisting of monophosphoryllipid A (MPL), trehalose dimycolate (TDM), and cell wall skeleton (CWS), preferably MPL+CWS (Detox™).

Other adjuvants contemplated for the invention are saponin adjuvants, such as Stimulon™ (QS-21, Aquila, Framingham, Mass.) or particles generated therefrom such as ISCOMs (immunostimulating complexes) and ISCOMATRIX. Other adjuvants include RC-529, GM-CSF and Complete Freund's Adjuvant (CFA) and Incomplete Freund's Adjuvant (IFA).

Other adjuvants include cytokines, such as interleukins (e.g., IL-1α and β peptides, IL-2, IL-4, IL-6, IL-12, IL13, and IL-15), macrophage colony stimulating factor (M-CSF), granulocyte-macrophage colony stimulating factor (GM-CSF), tumor necrosis factor (TNF), chemokines, such as MIP1α and β and RANTES. Another class of adjuvants is glycolipid analogues including N-glycosylamides, N-glycosylureas and N-glycosylcarbamates, each of which is substituted in the sugar residue by an amino acid, as immunomodulators or adjuvants (see U.S. Pat. No. 4,855,283). Heat shock proteins, e.g., HSP70 and HSP90, may also be used as adjuvants.

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS-21 are preferred. Optionally, two or more different adjuvants can be used simultaneously. Preferred combinations include alum with MPL, alum with QS-21, MPL with QS-21, MPL or RC-529 with GM-CSF, and alum, QS-21 and MPL together. Also, Incomplete Freund's adjuvant can be used (Chang et al., *Advanced Drug Delivery Reviews* 32, 173-186 (1998)), optionally in combination with any of alum, QS-21, and MPL and all combinations thereof.

Agents for inducing an immune response can be administered by parenteral, topical, intravenous, oral, subcutaneous, intraarterial, intracranial, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles.

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/ml, formulated in aqueous buffer consisting of 50 mM L-histidine, 150 mM NaCl, adjusted to pH 6.0 with HCl. Composition for parenteral administration are typically substantially sterile, isotonic and manufactured under GMP conditions of the FDA or similar body.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, *Science* 249, 1527 (1990) and Hanes, *Advanced Drug Delivery Reviews* 28, 97-119 (1997). The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., *Nature* 391, 851 (1998)). Co-administration can be achieved by using the components as a mixture or as linked molecules obtained by chemical crosslinking or expression as a fusion protein.

Alternatively, transdermal delivery can be achieved using a skin path or using transferosomes (Paul et al., *Eur. J. Immunol.* 25, 3521-24 (1995); Cevc et al., *Biochem. Biophys. Acta* 1368, 201-15 (1998)).

VI. Treatment Methods

In another aspect, a pharmaceutical composition including a therapeutically effective amount of a humanized antibody capable of binding a pertussis toxin protein and a pharmaceutically acceptable excipient is provided. The humanized antibody is a humanized antibody as described herein, including embodiments thereof.

In another aspect, a method of treating a disease caused by *Bordetella pertussis* bacterium (e.g. whooping cough) in a subject in need thereof is provided. The method includes administering to the subject a therapeutically effective amount of a humanized antibody capable of binding a pertussis toxin protein and a pharmaceutical carrier, thereby treating whooping cough in the subject. The humanized antibody is a humanized antibody as described herein, including embodiments thereof. In some embodiments, the subject is human.

The term "therapeutically effective amount" means the amount of the humanized antibody that will elicit the biological or medical response of a cell, tissue, system, or animal, such as a human, that is being sought by the researcher, veterinarian, medical doctor or other treatment provider.

Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make isotonic; antioxidants, preservatives, low molecular weight polypeptides, proteins, hydrophilic polymers such as polysorbate 80, amino acids such as glycine, carbohydrates, chelating agents, sugars, and other standard ingredients known to those skilled in the art (Remington's Pharmaceutical Science 16$^{th}$ edition, Osol, A. Ed. 1980). The mAb is typically present at a concentration of 0.1-100 mg/ml, e.g., 1-10 mg/ml or 10-50 mg/ml, for example 5, 10, 20, 30, 40, 50 or 60 mg/ml.

A pharmaceutical composition including a humanized antibody as described herein can be administered by a variety of methods known in the art. The route and/or mode of administration vary depending upon the desired results. In some embodiments, administration is intravenous, intramuscular, intraperitoneal, or subcutaneous, or administered proximal to the site of the target. Pharmaceutically acceptable excipients can be suitable for intravenous, intramuscular, subcutaneous, parenteral, spinal or epidermal administration (e.g., by injection or infusion).

Pharmaceutical compositions of the humanized antibody can be prepared in accordance with methods well known and routinely practiced in the art. See, e.g., Remington: The Science and Practice of Pharmacy, Mack Publishing Co., 20$^{th}$ ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the humanized antibody is employed in the pharmaceutical compositions of the invention. The humanized antibodies can be formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It may be advantageous to formulate the humanized antibodies in combination with other therapies or agents. It can be advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of humanized antibody calculated to produce the desired therapeutic effect in association with the required pharmaceutical excipient.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, the route of administration, the time of administration, the rate of excretion of the particular antibody being employed, the duration of the treatment, other drugs, compounds and/or materials used in combination with the particular compositions employed, the age, sex, weight, condition, general health and prior medical history of the patient being treated, and like factors.

A physician or veterinarian can start doses of the humanized antibodies of the invention employed in the pharmaceutical composition at levels lower than that required to achieve the desired therapeutic effect and gradually increase the dosage until the desired effect is achieved. In general, effective doses of the compositions of the present invention vary depending upon many different factors, including the specific disease or condition to be treated, means of administration, target site, physiological state of the patient, whether the patient is human or an animal, other medications administered, and whether treatment is prophylactic or therapeutic. Treatment dosages need to be titrated to optimize safety and efficacy. For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months.

Antibody can be administered on multiple occasions. Intervals between single dosages can be weekly, monthly or yearly. Intervals can also be irregular as indicated by measuring blood levels of the humanized antibody in the patient. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

VII. EXAMPLES

The following examples are intended to illustrate certain embodiments of the methods and compositions provided herein and are not intended to limit the scope of the invention.

Applicants cloned and expressed 1B7 and 11E6 as recombinant antibodies. Applicants also evaluated parameters that determine the success of antibody neutralization of pertussis toxin, in particular, the stability of these recombinant antibodies. Further, Applicants humanized the antibody binding site prior to production as a full-length humanized IgG.

The antibody variable regions were cloned and expressed using standard methods (Krebber et al., 1997). Humanization was based upon the method of Baca 110 (1997), in which the antibody CDR loops replace the CDRs of the human germline consensus sequence, and certain framework residues are retained with the murine identity. Screening by phage display of directed randomized libraries was used to identify humanized variants which retain binding capacity.

Antibody expression problems were solved by the use of a C-terminal protein fusion (HuCκ), and co-expression of the molecular chaperone, skp. Yields of purified protein increased from ~10 μg/L to almost 7 mg/L culture for the best-expressed variant. Pertussis toxin assays are much longer than anthrax toxin assays (48 hours for in vitro assays; 18 days for in vivo) magnifying the need for stable molecules. The anti-PT molecules are rapidly deactivated at 37° C., compromising their ability to protect cells in vitro. In fact, antibodies with the same affinity but dramatically different stabilities at 37° C., such as the 1B7 and 3A scAbs, required four-fold difference in antibody concentrations to provide equal protection. Similarly, an antibody with higher stability but lower affinity than 1B7, 1B7-Cys23, also required a four times higher concentration to provide equal neutralization as 1B7. Fab fragments of 1B7 that have been shown to be very stable and to have the same affinity as the 1B7 scAb, required nine-fold lower antibody concentration to protect cells as compared to the 1B7 scAb.

Example 1

Functional Characterization of Truncated PTx-S1, the B-oligomer, and Naturally Occurring PTx-S1 Variants To facilitate mutagenesis of the toxin, PTx-S1 from strain Tohama I (variant B) was expressed recombinantly in *E. coli*. Yields of full length PTx-S1 (amino acids residues 1-235) were extremely low due to the presence of a long hydrophobic tail anchoring PTx-S1 into the B-oligomer, but a truncated version consisting of amino acid residues 1-220 was expressed and purified from the bacterial periplasm [24]. Protein purity was assessed by size exclusion chromatography and SDS-PAGE. Binding between 1B7 and the commercially available holotoxin, PTx-S1 (1-235), B-oligomer, and recombinant PTx-S1-220 were measured by ELISA and SPR using a BIAcore3000 biosensor. PTx-S1 and PTx-S1-220 bound 1B7 with similar kinetics, $k_d$ of 1.9 and $1.4 \times 10^{-3}$ seq$^{-1}$, respectively (see Table 1 and FIG. 2). These data indicate that the PTx-S1 truncation does not affect the affinity of 1B7 for PTx-S1, and therefore the truncated PTx-S1 format was used to generate and analyze all subsequent site-directed toxin variants.

A systematic loss of affinity was observed for both the truncated PTx-S1-220 and the full length PTx-S1 (off-rates of 1.9 and $1.9 \times 10^{-3}$ sec$^{-1}$, respectively), versus the holotoxin (off-rate of $0.4 \times 10^{-3}$ sec$^{-1}$). To explain this loss, first a weak binding was noticed between hu1B7 and the B-oligomer via ELISA ($EC_{50-PTx}$ of 8%). More detailed analysis with SPR detected an off-rate of $2.7 \times 10^{-3}$ sec$^{-1}$ between purified B-oligomer and immobilized monoclonal antibody 1B7 when a high concentration of B-oligomer was used (1150-2890 nM). When the ELISA was repeated using monoclonal antibody 1B7, an $EC_{50-PTx}$ of 30% for B-oligomer versus holotoxin was measured.

To address the potential for natural or vaccine-induced epitope drift to result in S1 variants no longer bound by 1B7, truncated PTx-S1 proteins (AA 1-220) corresponding to three remaining naturally occurring variants (PTx-S1A, PTx-S1D, and PTx-S1E) were cloned and expressed using site-directed mutagenesis of PTx-S1B. This was also performed for the catalytically inactive, genetically detoxified variant (PTx-S1 9K/129G) which is promoted for use in acellular vaccines to reduce side effects while retaining most adjuvant and protective qualities [38]. The *B. bronchiseptica* PTx-S1 subunit containing four mutations (D34E, 1198T, 5209P, and Y161P) was also constructed, but did not express well enough to include in the analysis [39]. Reducing and non-reducing SDS-PAGE gels confirmed the correct molecular weight and purity of the naturally occurring PTx-S1-220 variants compared with the parent PTx-S1B from the Tohama I strain. Binding analysis of these S1 variants using ELISA and SPR measured mAb 1B7 off-rates for both PTx-S1E and PTx-S1 9K/129G within error of those measured for PTx-S1-220 (1.8 and $1.6 \times 10^{-3}$ sec$^{-1}$, respectively). Slightly slower off-rates were measured for PTx-S1A and D (0.7 and $0.95 \times 10^{-3}$ sec$^{-1}$, respectively; see Table 1). Thus, the neutralizing epitope recognized by 1B7 is conserved across all known PTx-S1 variants, including laboratory-generated, catalytically inactive variants.

Functional Characterization of 1B7 Recombinant Antibodies

Figure 3:
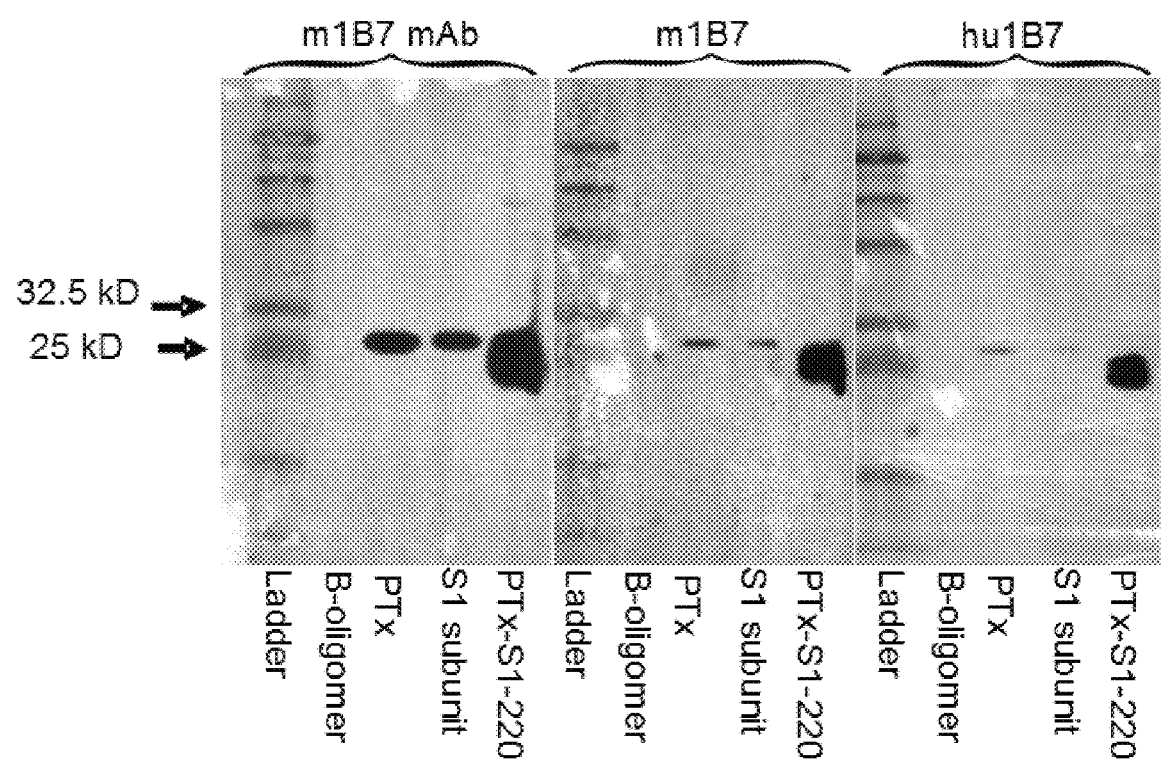

Two recombinant versions of mAb 1B7, murine (m1B7) and humanized (hu1B7) single-chain Fv antibodies (scAb, a scFv with a c-terminal human kappa constant domain), were constructed by RT-PCR, overlap PCR, and CDR grafting as previously described (data not shown) [25-27]. This single-gene, single protein format facilitated rapid site-directed mutagenesis and expression of the resulting variant proteins. To characterize m1B7 and hu1B7 binding behavior, a western blot containing the B-oligomer, PTx, PTx-S1, and PTx-S1-220 in triplicate was probed with mAb 1B7, m1B7, and hu1B7 (see FIG. 3). All three constructs bound PTx-S1 from the holotoxin, PTx-S1, and the truncated PTx-S1-220 with no detectable binding to any of the remaining four subunits. The intensity of the bands corresponds with the affinity of the antibody format for holotoxin or PTx-S1 (mAb 1B7>m1B7>hu1B7). Although hu1B7 exhibits the lowest overall binding affinity, this version expressed much better than m1B7 and was used as the parent for site-directed mutagenesis.

A CHO cell neutralization assay was conducted to evaluate the ability of the antibody constructs to effectively neutralize PTx in an in vitro assay. A prerequisite for success in this assay is thermal stability, as antibodies must retain their binding ability for at least 24 hours in serum at 37° C. To rule out the possibility that hu1B7 scAb variants may not protect in the in vitro assay due to poor thermal stability, antibody samples at 37 μg/ml were heated at 37° C. for 24 hrs and 50° C. for 2 hrs prior to binding analysis. The fraction of functional scAb remaining was quantified by ELISA with reference to mock-treated samples. All three constructs (mAb 1B7, m1B7 and hu1B7) retained at least 70% affinity at assay conditions and less than 40% affinity after exposure to the higher temperature (see Table 2). The molar ratio of antibody to toxin required to protect CHO cells in vitro corresponded to the relative antibody binding affinities, with m1B7 requiring a 10-fold and hu1B7 a 30-fold increase in the molar excess of antibody versus mAb 1B7. Despite a drop in affinity relative to the mAb 1B7, both m1B7 and hu1B7 not only retained the ability to bind purified PTx with high affinity, but also to effectively neutralize the toxin in vitro.

Computational and Experimental Selection of Residues for Interaction Analysis

To reduce the experimental workload, residues were selected for alanine point mutagenesis analysis in conjunction with two computational methods, (1) ZDock [32] coupled with Rosetta Computational Mutagenesis Alanine Scanning [33-35] and (2) Pepsurf [36] coupled with previously determined 1B7 phage peptides [37]. Due to the absence of a crystal structure of either hu1B7 or m1B7, two antibody structure prediction algorithms, Rosetta Antibody Beta [31] and Web Antibody Modeling (WAM) [30], were used to predict four possible antibody structures. All the resulting models had random mean square deviations (rmsd) of approximately 1 Å for the overall structure, the CDR loops, and a few key residues (L-W91A and H-W33A) except the Rosetta hu1B7 model. Due to the similarity of the other three models in addition to the improved expression levels of hu1B7, the hu1B7 WAM model was chosen for subsequent docking models. The crystal structure of PTx-S1 [23] and a WAM antibody predicted structure of hu1B7 were run using method 1, resulting in the prediction of an initial docked model. This was then used for in silico alanine point mutagenesis to guide experiments by predicting which residues would result in the highest loss of free energy, $\Delta\Delta G$ complex$\geq 1.0$ kcal/mol, for each partner. Twelve residues on hu1B7 (see Table 3) and fourteen residues on PTx-S1 (see Table 4) were chosen based upon their resulting $\Delta\Delta G$ complex, amino acid residues over-represented in protein-protein interactions, and spatial proximity to the binding partner.

Method 2 was performed to take advantage of previously identified peptides mimicking the PTx-S1 epitope. Pepsurf compared the peptide sequences to the holotoxin crystal structure, identifying three potential conformational epitopes on PTx. Only two of these predicted epitopes were likely candidates since the third predicted no binding of PTx-S1. The "best cluster" consisted of the following: A74, G78, R79, G80, T81, H83, and I152 on PTx-S1 and A40 on PTx-S4. Two of these predicted residues, T81 and H83, were also predicted using the first method. If the prediction of partial binding to PTx-S4 is correct, it would explain the reduction in off rates and affinity seen in PTx-S1 versus PTx binding. This weak interaction could be below the sensitivity of either western blot analysis or SPR or simply non-existent when looking at PTx-S4 alone due to its sole stabilizing role in the 1B7/PTx-S1 interaction. The "second cluster" consisted of the following: P3, P4, A5, P175, N176, and P177 on PTx-S1. This "second cluster" is highly unlikely since previous studies have determined that the first six residues of PTx-S1 are not involved in the binding of monoclonal antibody 1B7 [19]. Amino acid residue N176 was chosen in order to confirm this hypothesis. Further analysis using the peptide sequences as linear epitopes and comparison with PTx-S1 amino acid sequence resulted in identification of one addition cluster containing R39. Overall, an additional three residues were chosen based upon this second method, resulting in a total of seventeen PTx-S1 residues for experimental alanine scanning analysis.

Experimental and Computational Residue Analysis

After point mutagenesis to alanine of each chosen residue, each resulting variant was expressed in *E. coli* and purified on at least three separate occasions. These purified variants were first analyzed for a change in affinity toward PTx or WT hu1B7 via ELISA. Variants were categorized as either non-binding or reduced binding based upon average $EC_{50}$ cutoffs of less than 1% or less than 40%, respectively. For WT hu1B7, three variants were determined to be non-binding (L-W91A, H-W33A, and H-N58A) and three were determined to be lower binding (L-F31A, L-H94A, and H-S97A). PTx-S1 was had four non-binding variants (R79A, H83A, Y148A, and N150A) and six lower binding variants (E16A, R39A, T81A, T153A, T158A, and Y166A).

In order to verify these results, a second assay was performed on each of the variant types. For the hu1B7 variants, heat studies and in vitro CHO cell neutralization assays were performed. The heat studies resulted in all variants retaining >70% affinity at assay conditions, except L-F31A which only retained 60% affinity. The results of the CHO cell assay showed that L-W91A, H-W33A, H-N58A, L-H-94A, H-S97A, and L-F31A offer no protection in vitro, thereby confirming the ELISA results. SPR analysis confirmed that PTx-S1 variants R79A, H83A, Y148A, and N150A have significantly reduced affinity for monoclonal antibody 1B7 as seen by their rapid off-rates of 25, 10, 29, and $8\times 10^{-3}$ $\sec^{-1}$, respectively. Of the previously classified lower binding variants, R39A and T153A showed higher off rates than WT PTx-S1-220 at 3.0 and $2.0\times 10^{-3}$ $\sec^{-1}$, while the other four variants, E16A, T81A, T158A, and Y166A, had similar off rates of 1.6, 1.7, 1.3, and $1.4\times 10^{-3}$ $\sec^{-1}$ thereby changing their classification to binding. The computational methods used to guide experimental efforts correctly predicted residues with experimental $\Delta\Delta G_{(complex)}>1$ kcal/mol with approximately 50% accuracy. The experimental results confirm the most likely cluster predicted with Pepsurf as PTx-S1 residues R79A and H83A were non-binding in all assays.

Although several variants of both WT hu1B7 and PTx-S1 were identified as non-binding or reduced binding, this change could be due to indirect structural effects as opposed to a reduction in binding energy. Focusing first on WT hu1B7, three of the identified residues (L-W91, H-W33, and L-H94) are considered structurally relevant in the CDR regions of antibodies [40, 41]. The in silico alanine scanning results were then re-analyzed focusing on the value of the calculated $\Delta G$ (partner), for which a value of greater than 1.0 indicates the residue may play a role in stabilizing protein secondary and tertiary structure. This analysis identified residues L-W91, H-W33, and L-F31 as playing structural roles. The final method to determine each residues contribution to proper folding was experimental comparison of CD analysis of each variant with WT hu1B7. This indicated that experimentally only H-S97A and H-W33A were structurally different than the WT. Based upon these three methods, only H-W33 consistently appears to be structurally important. However, this residue has ~15% solvent accessibility and has been shown to form hydrogen and pi bonds with residues across the interface of the HEL/FabD44.1 interaction [40]. A similar method was used to determine the structural importance of the PTx-S1 residues. $\Delta G$ (partner) analysis identified all residues except R79 as structural, while CD analysis with comparison to WT PTx-S1-220 indicated only N150A and R79 as structurally different. Due to the results being method dependent, only N150 can definitely be classified as a structurally important residue. This conclusion is further cemented by structural analysis of PTx-S1 which shows N150 as 7% solvent accessible and playing a key role in a β-sheet structure with 5 hydrogen bonds with neighboring PTx-S1 residues. Despite the structural roles of both H-W33 on WT hu1B7 and N150 on PTx-S1, the docked model indicates hydrogen bonding of these residues with partner residues across the interface. The model indicates these residues serve dual roles maintaining structural conformation and mediating antigen/antibody binding.

Figure 4A:
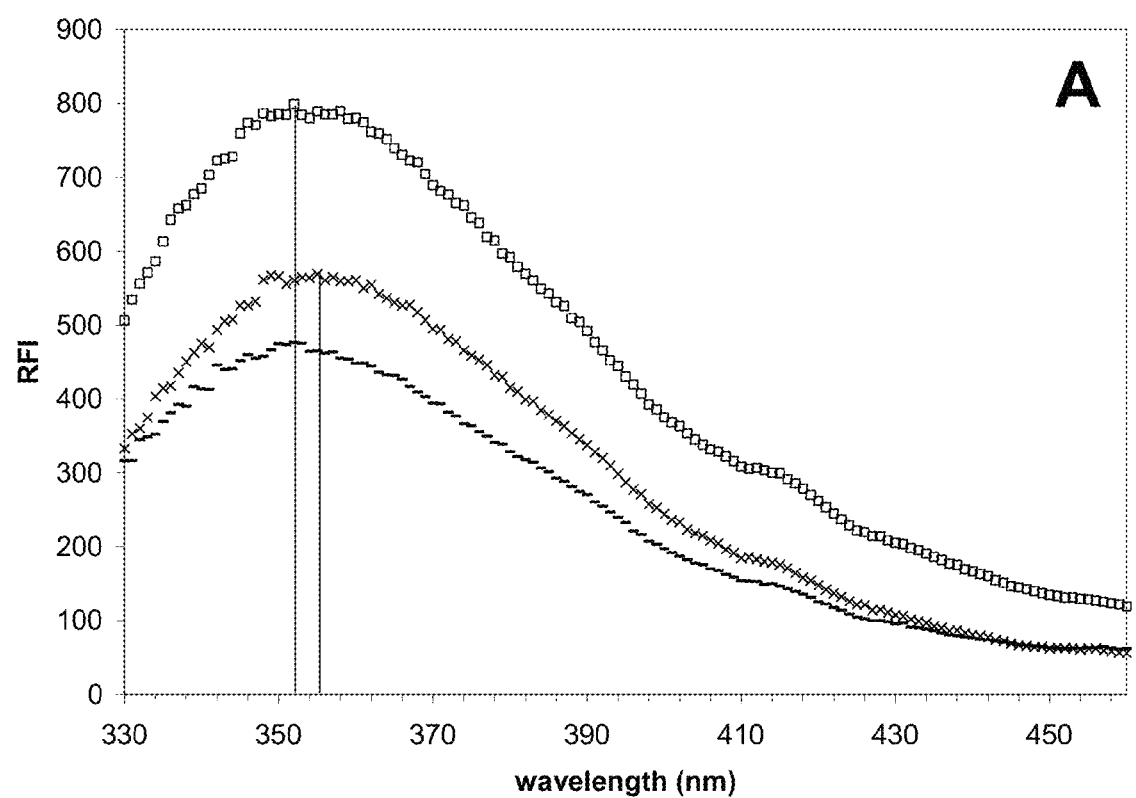
Figure 4B:
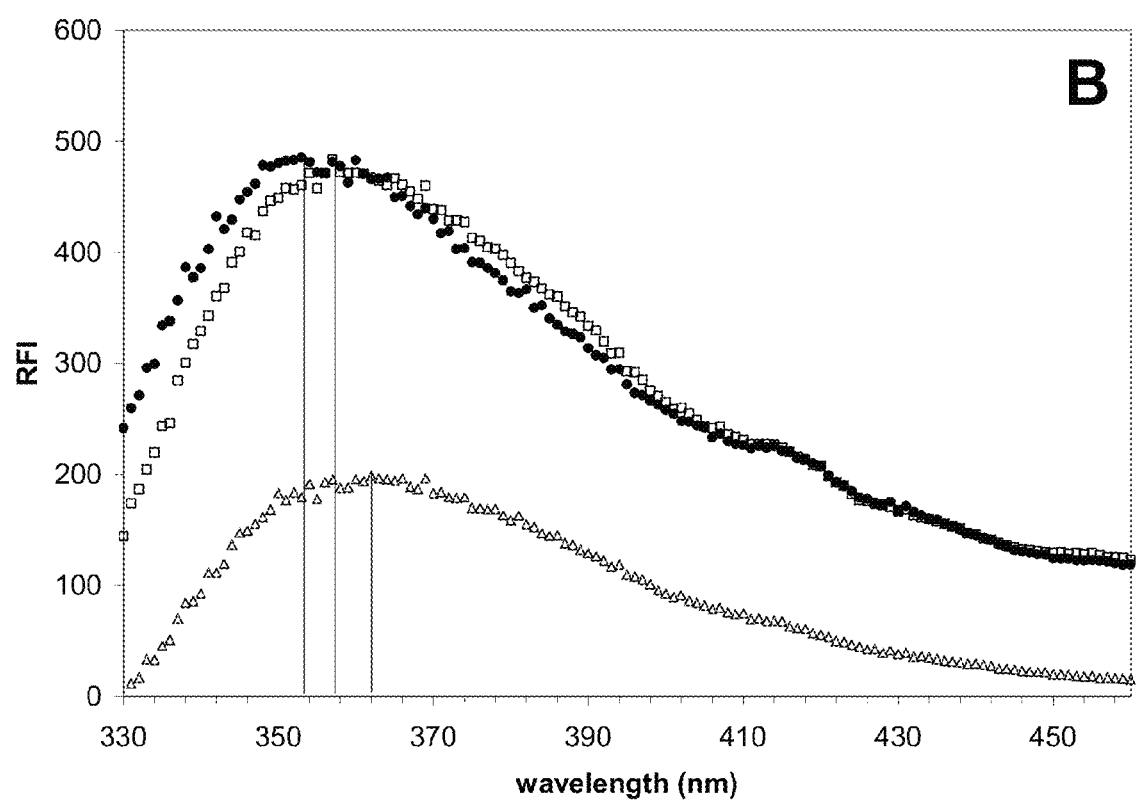

As a final check as to whether the identified tryptophan residues (L-W91 and H-W33) are located at the complex interface, tryptophan fluorescence measurements were collected individually for the two tryptophan deficient variants, L-W91-A and H-W33-A, in addition to WT hu1B7 and PTx-S1-220 (see FIG. 4A). Comparison of WT hu1B7 with L-W91-A and H-W33-A shows relative peaks of 60% and 70%, respectively, indicative of the decrease in the total number of tryptophan residues. While L-W91-A shows no shift in peak position, a red shift of 3 nm was observed for H-W33-A, signifying tryptophan exposure. This shift is most likely due to a conformational change, which is expected due to the structural role played by this residue. Fluorescence measurements of WT hu1B7, PTx-S1-220, and the equimolar complex of the two were then collected (see FIG. 4B). Comparison of the complex with WT hu1B7 and PTx-S1-220 resulted in blue shifts of 4 and 9 nm, respectively. This masking of the tryptophans [42] confirms their presence in the binding interface between WT hu1B7 and PTx-S1-220.

Development and Prediction of Best Fit Model of Interaction

Figure 5:
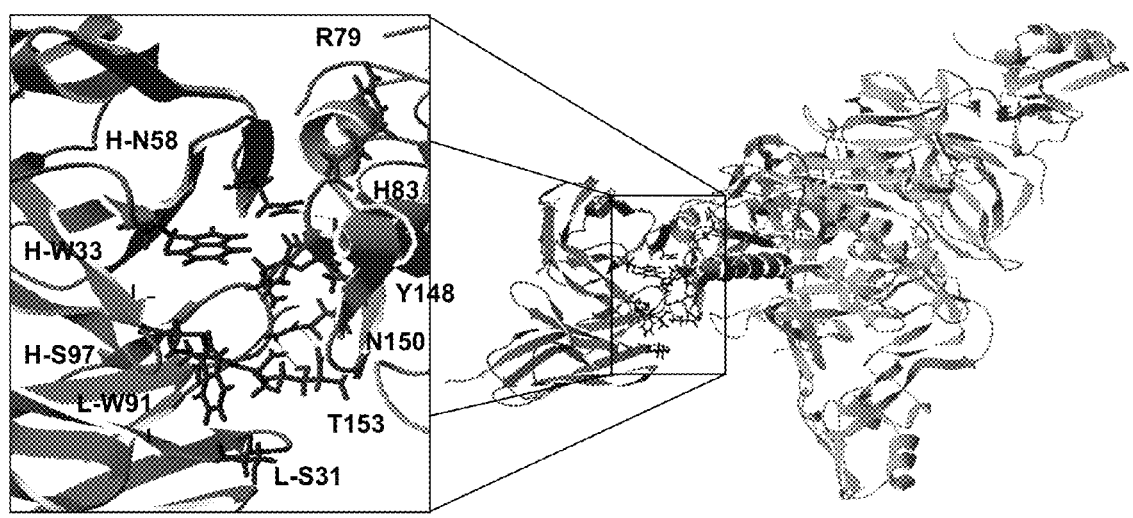

With these twelve "key binding residues" in mind, as well as the requirements for geometric and electrostatic complementarity to allow binding, WT hu1B7 was manually docked onto PTx-S1 using the molecular viewing programs Swiss PDB Viewer and Pymol to provide a starting complex for computational refinement. The resulting complex was submitted for computational docking using RosettaDock, which is able manipulate the two docked partners +/−3 Å toward or away from each other, 8 Å along each other's surface, 8 Å of tilt, and 360° around the center axis between the two [33]. Of the resulting models, the one which best fit the experimental data, predicting interactions of five of the six PTx-S1 residues and also five of the six WT hu1B7 residues, was selected (see FIG. 5). The model predicts hydrogen bonding between N150 and the backbone oxygen of L-W91, H-N58 and the backbone oxygen of H83, N150 and the backbone oxygen of L-S92, and T153 and the backbone oxygen of L-S92. It also predicts hydrogen bonding between several residues determined to be unimportant for binding: E16, R146, L-S92, and L-S93. Although Y148 does not form any predicted hydrogen bonds, it has a large solvation energy effect of 0.14 kcal/mol, indicating solvent interaction. Looking at the residue side chains, nearly half are aromatic residues with two tryptophans, two histidines, and one tyrosine. Since aromatic clusters are common at protein-protein binding interfaces, comprising ~30% of energetically important residues [41], the binding chemistry may involve π-bonding or stacking between the two tryptophans on the antibody and the histidine on PTx-S1. Changes in either salt or pH conditions did not significantly affect binding (data not shown), consistent with a binding interface dominated by hydrophobic interactions.

As a final check on the probability of the proposed model, the change in Gibbs free energy for the 1B7/PTx-S1 complex was calculated from experimental equilibrium affinity using the change in Gibbs free energy equation as follows (Eqn 1):

$$\Delta G = -RT\ln(K_{eq}) = \sum_{i=1}^{n} \Delta\Delta G_i$$

Using the known $K_d$ of 5 nM, the gas constant (R) of 1.987 cal/mol, and 277 K for temperature (T), the ΔG of the complex was calculated to be 10.5 kcal/mol. In the absence of non-additive co-operative effects [43], this value should also equal the sum of the ΔΔG for each binding residue of the complex, with any deviation between these values indicating one or more binding residues have been omitted. In silico computational alanine scanning of the hu1B7-Ptx-S1 complex results in a $(\Delta\Delta G)_{sum}$ of 10.5 kcal/mol, very similar to the predicted ΔG and in the predicted range for antibody-antigen complexes (ΔG=10.9-12.3 kcal/mol for $K_d$'s from 10-1 nM). This correspondence indicates that a majority of interacting residues have likely been identified.

As the *B. pertussis* organism has not been detected in the blood of patients, it has been suggested that the systemic manifestations are due to toxin release and dissemination. Pittman famously hypothesized that symptoms are mediated primarily by pertussis toxin (PTx), a theory which, 30 years later, remains to be proven. It is clear that PTx is a major antigen, as transposon-insertion mutants of *B. pertussis* manifest greatly reduced virulence in mice [44] and administration of purified toxin induces numerous effects associated with infection such as histamine-sensitization, leukocytosis, and insulin secretion. In terms of protection, it has been difficult to demonstrate a definitive correlation between a humoral response to any antigen and protection against disease although qualitatively high levels of antibody to PTx are associated with a lower likelihood of developing clinical disease upon exposure to pertussis. [11, 45]

After immunization with PTx, antibodies recognizing the S1 subunit are recovered at high frequency [15], indicating this subunit as a whole is strongly immunogenic. Analysis of monoclonal antibodies binding PTx have documented the presence of at least four non-overlapping epitopes on the PTx holotoxin; monoclonal antibodies binding two of these (on the S1 and S2/3 subunits) have been shown to be protective in mouse models [15-17]. Sato et at performed a detailed comparison of 10 anti-PTx-S1 antibodies, polyclonal anti-PTx sera, and 10 anti-B-oligomer antibodies in the mouse aerosol model [8]. Remarkably, only the 1B7 antibody conferred significant survival when administered between zero and seven days after infection while also reducing the number of bacteria and amount of PTx in the lungs [8]. This anti-PTx-S1 antibody may protect by binding an epitope which prevents substrate access to the catalytic cleft or restricts unfolding of the S1-subunit necessary for translocation to the cytoplasm, while non-protective anti-PTx-S1 antibodies bind a separate epitope and do not interfere with PTx-S1 function (see FIG. 1). The infrequent recovery of antibodies displaying 1B7-like neutralizing activities suggests that (1) the antibody or the epitope recognized possess unique protective qualities and (2) that the epitope is poorly immunogenic.

Location of the Neutralizing Epitope on PTx Recognized by Monoclonal Antibody 1B7

Prior efforts to characterize the conformational epitope on PTx-S1 bound by 1B7 using truncations, deletions, and peptide fragments identified two linear sub-epitopes involved in the binding (AA 8-14 and 124-186) [18, 21]. These appeared to be independent linear sub-epitopes as mutations in either region was associated with loss of binding on a Western blot. Since 1B7 inhibits toxin-mediated ADP ribosylation of G proteins in vitro, early reports suggested the antibody may directly and predominately interact with the catalytic residues located in the linear region between AA 8-14 which shows homology with both cholera toxin and *E. coli* heat labile toxin. The PTx holotoxin structure, published subsequently [23], revealed that residues 9-13 are mostly buried (≤13% solvent accessible), making it unlikely that antibodies could interact directly with these in a properly folded protein. However, Western blot analysis showed that 1B7 was unable to bind Y8A and had a reduced ability to bind R13A (see Table 5). The relevance of this linear interaction is unclear since 15-mer PTx-S1 peptides capable of recapitulating this linear binding site could not be identified [16]. Furthermore, antibody conformational epitope prediction programs including ElliPro, Discotope, and Pepsurf did not predict binding residues in this region.

Using a combination of experimental and computational techniques, the PTx holotoxin structure and prior data, a model of the interaction between PTx and the neutralizing antibody 1B7 has been developed. Using primarily CDR loops L3 and H3, 1B7 binds the base of PTx-S1, possibly engaging in weak interactions with the S4 subunit (see FIG. 5). This region of PTx-S1 appears readily accessible to antibodies and is fairly flat, consisting of three anti-parallel β-sheets and two different turns: one between the aforementioned β-sheets and another prior to an α-helix. The energetically important PTx-S1 residues, assessed by alanine scanning mutagenesis, are R79, H83, N150, and Y148. Chemically, the surface is mostly hydrophobic with one arginine, nine hydrogen bonds, and a solvent-accessible area of ~1000 Å², typical for antibody-antigen interactions. Interestingly, both the model and data support a weak stabilizing interaction with the S4 subunit of the B-oligomer involving a separate turn between O-sheets. Although only S4 residue A40 was suggested by Pepsurf, due to their close proximity, residues S42 and S43 may also be involved in this interaction. Overall, this is a conformational epitope which includes a short linear sequence (Y148 to N150 along a β-sheet strand), consistent with 1B7's ability to bind reduced and denatured PTx-S1 on a Western blot. This is consistent with a linear sub-epitope between AA124-186. Binding of monoclonal antibody 1B7 to the PTx-S1-220 variants, N150A and Y148A, was not detected in ELISA with up to 1.6 µM antibody. Similarly, 1B7 monoclonal antibody had greatly reduced ability to bind N150A and no ability to bind Y148A on a Western blot using very sensitive chemiluminescence detection (see Table 5).

Figure 6:
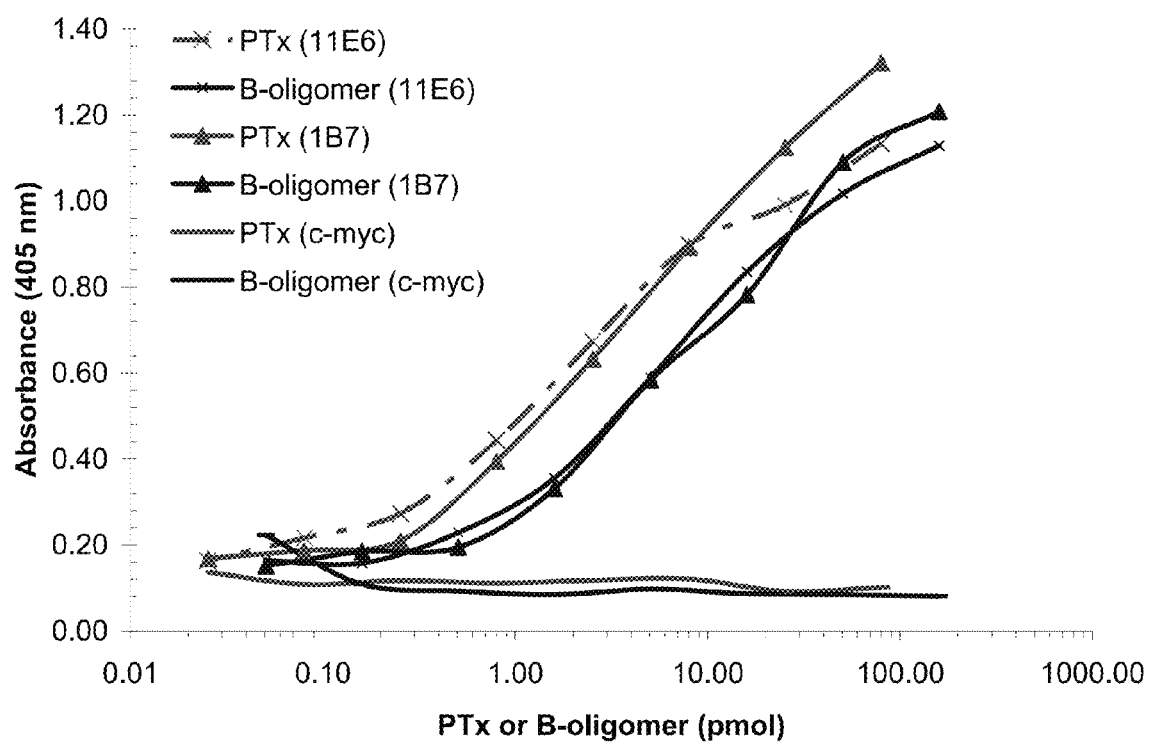

Involvement of the B-oligomer in this protective epitope is indicated by the marked reduction in mAb 1B7 binding to PTx holotoxin ($k_d$ of $0.4+/-0.6 \times 10^3$ sec$^{-1}$) versus PTx-S1 ($k_d$ of $1.9+/-0.3 \times 10^3$ sec$^{-1}$). This reduction in binding affinity is observed with both the commercially prepared S1-235 and the recombinant, truncated S1-220, indicating it is not an artifact of the recombinant version (see Table 1). Interestingly, although both ELISA and SPR analysis measured a weak interaction between the B-oligomer and mAb 1B7 (see FIG. 6), no recognition of the B-oligomer was detected by chemiluminescent Western (see FIG. 3). There are three possibilities to explain this result: (1) 1B7 recognizes a separate conformational epitope on the B-oligomer at significantly lower affinity than PTx-S1; (2) 1B7 recognizes a single epitope dominated by PTx-S1 but supplemented by a weak B-oligomer interaction; (3) PTx-S1 is stabilized by its interaction with the B-oligomer resulting in reduced entropic costs of 1B7 binding. If 1B7 does interact with both the S1 and S4 subunits, this may explain both the low frequency at which 1B7-like antibodies are recovered, since the antibody would need to span the A-B subunit interface. Moreover, it suggests a mechanism of protection: 1B7 may act as a molecular staple linking PTx-S1 to the B-oligomer, slowing PTx-S1 unfolding and dissociation from the B-oligomer in the ER, reducing the ability of PTx-S1 to escape to the cytosol and perform catalysis. Validation of this model by co-crystallization of 1B7 with PTx is on-going to provide direct experimental evidence of the 1B7 binding site.

Contribution of mAb 1B7 to PTx Recognition

Although previous studies have focused on the 1B7 epitope on PTx-S1, the antibody itself may possess unique qualities which result in effective neutralization. In addition to blocking toxin catalysis, 1B7 binding may, for instance, slow toxin unfolding necessary for escape from the ER into the cytoplasm (see FIG. 1). To understand the antibody's role in binding and to aid in creating a docked model of the interaction, twelve hu1B7 residues predicted to contribute significantly to the energetics of binding were individually altered to alanine. These experiments identified six key residues required for high-affinity binding to S1, L: F31, H94, W91 and H: S97, W33 and N58. These six residues are equally distributed over the heavy and light chains, with a slight bias towards CDR L3. Of the CDRs, only L2 contains no key residues and does not appear to contribute significantly to the interaction. This is consistent with most antibody-antigen contacts wherein CDR-L2 only has the least involvement of all the CDR loops with contacting residues on 42% of the time (www.bioinf.org.uk). Of the six key residues, H-W33, L-W91, H-S97 and L-H94 are common interacting residues with contacts in over 70% of complexes. The other two residues, L-F31 and H-N58, are less common at 15 and 38% respectively. However, L-F31 mutation to alanine only resulted in reduced binding and is thus not thought to be a large contributor to the interaction. Overall, the residues chosen on 1B7 for analysis using RosettaDock and ZDock were correctly predicted in 50% of the cases. Based on these results, further optimization of 1B7 binding could be achieved by targeted mutagenesis of CDRs L3 and H3, which often dominate binding in antibody complexes.

Epitope Conservation Across Naturally Occurring and Engineered Strains

A consequence of broad vaccination programs is the potential to select for escape variants of the major virulence factors, which may be accelerated by the use of acellular vaccines. Detailed genotyping of strains, primarily in the Netherlands, has aimed to track naturally occurring and vaccine-induced variation in pertussis antigens [46]. The naturally occurring mutations in these strains (PTx-S1A, PTx-S1D, and PTx-S1E) are mainly found in the S1 subunit with each variant containing up to three amino acid substitutions with respect to PTx-S1B (Tohama-I) [47]. The most divergent PTx-S1 gene is found in *B. bronchiseptica* with four amino acid mutations but is not expressed due to promoter mutations [39, 46].

Given this modest level of natural variation, a key question is whether variation impacts in the 1B7 epitope, and if so, whether 1B7 bind these variants with the same affinity. After expression and purification of truncated versions (1-220) of three of the four naturally occurring strain variants, it was found that PTx-S1E is bound by 1B7 with identical (within error) off-rates versus WT PTx-S1-220 (see Table 1). However, 1B7 had approximately a two-fold decrease in off-rates with respect to PTx-S1A and PTx-S1D, indicating an increase in affinity. A second question is whether the catalytically inactive PTx-S1 variant used in some acellular vaccines (containing amino acid substitutions R9K and E129G) will also be recognized by 1B7. 1B7 binds this PTx-S1 variant with identical affinity as WT (within error), suggesting that acellular vaccines containing the R9K, E129G variant will be able to elicit 1B7-like protective antibodies. The value of the 1B7 epitope as a target for passive immunization and a potential correlate of protective immunity will depend both on its ability to elicit neutralizing 1B7-like antibodies and conservation within the pool of circulating clinical strains. The ability of hu1B7 to bind existing PTx-S1 variants indicates that the epitope recognized by 1B7 is conserved in the presence of natural antigenic drift.

Mechanism of PTx Neutralization by mAb 1B7

When originally characterized, the 1B7 monoclonal antibody was thought to protect against toxin effects by blocking catalysis, either by directly associating with catalytic residues or blocking substrate access to these residues. However, several other monoclonal antibodies have been characterized which block ADP ribosylation in vitro but are not neutralizing in vivo [15]. Furthermore, the mechanism of toxin cellular binding and internalization has been characterized in detail and it is not clear whether an antibody would remain associated with PTx-S1 during retrograde transport—in the low pH of the endosome, the reducing environment of the ER, or during translocation into the cytoplasm (see FIG. 1). The fact that 1B7 can bind reduced and unfolded PTx-S1 on a Western blot and under the cytoplasmic conditions replicated during in vitro ADP ribosylation assays suggests that it could block catalysis in the cytoplasm if present in that compartment, but 1B7 ligation may protect by altering PTx trafficking within the cell.

Burns and colleagues [39] demonstrated that PTx is transiently expressed on the bacterial cell surface during secretion and *B. pertussis* knock-out mutants have shown that along with FHA, PTx is necessary and sufficient for bacterial adherence. Thus, 1B7 may bind whole bacteria, blocking bacterial adhesion to respiratory epithelial cells or potentially mediating effector functions. 1B7 was isolated as a murine IgG2a antibody, an isotype able to opsonize bacteria and fix complement, while murine IgG1 isotypes are more commonly associated with toxin neutralization or blocking bacterial adherence. It is not clear if the isotype has mechanistic relevance or is a result of the Th1/Th2 bias induced by the toxin itself. F(ab')$_2$ fragments of anti-PTx antibodies [48] and Fab fragments of 1B7 [15] displayed identical in vitro CHO clustering effects as the parental monoclonal antibody. While the requirement for an Fc has not been directly tested in vivo, anti-PTx antibodies in human immune sera do not display opsonic activity or induce phagocytosis by human leukocytes [7, 11]. Similar to other toxin-mediated diseases, such as botulinum and anthrax [49], toxin neutralization may not require Fc-mediated effector functions, but remains an intriguing area of future investigation.

A uniquely neutralizing epitope on PTx using PTx-S1 variants and humanized scAb versions of the 1B7 monoclonal antibody has been indentified herein. This epitope is adjacent to but does not include the catalytically active residues on PTx-S1 and spans the junction between the S1 and S4 subunits. This model suggests a mechanism of 1B7 antibody protection: antibody ligation may anchor the catalytically active S1 subunit to the B-oligomer, thereby preventing PTx-S1 dissociation and subsequent transport into the cytosol, where PTx-S1 disrupts G-protein signaling. Confirmation of this model awaits additional co-crystallization and cellular experiments of antibody-toxin complex trafficking within cell. Notably, numerous anti-PTx-S1 antibodies have been produced with the ability to neutralize in vitro ADP-ribosylation activity, but most perform poorly in in vivo mouse models of disease. Thus Applicants propose that the molecular details of epitope recognition are critical in discriminating between antibodies capable of in vitro versus in vivo protection and that this epitope is a unique target to exploit for passive immunotherapy and acellular vaccine design. Moreover, it suggests that the search for immune correlates in pertussis may require careful examination of serum responses to specific epitopes, not just individual virulence factors [20, 22].

Experimental Procedures

PTx (holotoxin), the full length PTx-S1 (1-235) protomer, and the B oligomer were purchased from List Biological Laboratories, Inc., Campbell, Calif.

Antibody and Toxin Expression

The S1 subunit was amplified using oligonucleotide primers which truncated PTx-S1 from the amino terminus of the mature, processed protein to the carboxy-terminal residue 220, renamed PTx-S1-220 and sub-cloned into the expression vector pAK400 [25]. The expression vector pMoPac16, a pAK400 derivative with a c-terminal human constant κ-domain, was used to express scFvs as scAbs and the residues were numbered using the Kabat numbering system [26]. Point mutations for both scAbs and the truncated toxin S1 subunit were introduced by around the plasmid PCR [27].

Recombinant proteins were expressed in the bacterial periplasm of E. coli strain BL21 followed by osmotic shock and immobilized metal affinity chromatography purification was used to produce and purify all recombinant proteins as previously reported [28]. Size-exclusion chromatography with PBS as eluant was used as a polishing step for PTx-S1-220 and m1B7 scAb proteins (Superdex 75 and 200, respectively, GE Healthcare, Uppsala, Sweden). Protein L affinity chromatography was used as a second purification step for the hu1B7 scAb proteins (immobilized Protein L, Pierce, Rockford, Ill.) using 100 mM Na$_2$HPO$_4$, 150 mM NaCl pH 7.2 during binding and low pH IgG elution buffer (Pierce, Rockford, Ill.) followed by 1 M Tris pH 8.0 to neutralize eluted fractions. Micro-bicinchonoinic acid assay (Pierce, Rockford, Ill.) was used to measure protein concentrations while SDS-PAGE with GelCode Blue stain reagent (Pierce, USA) was used to verify protein preparation homogeneity and purity.

Antibody-Antigen Binding Analysis

High binding enzyme-linked immunosorbent assay (ELISA) plates (Costar) were coated with PTx at 1.3 μg/mL or serial dilutions of PTx-S1-220 or its variants and incubated at 4° C. overnight. The plates were then blocked with PBS+ 1% milk for an hour at room temperature. After washing 3 times with PBS+0.05% Tween 20, anti-PTx antibody (mAb 1B7, m1B7, hu1B7, or hu1B7 variants), was added either in serial dilution or at 8 μg/mL and allowed to equilibrate at room temperature for one hour. After washing an additional three times, peroxidase conjugated anti-human C$_k$ (Sigma) or peroxidase conjugated anti-mouse IgG (Sigma) was added for one hour at room temperature. Finally, the plate was washed 3 times and developed with tetramethylbenzidine dihydrochloride substrate (Pierce). The reaction was quenched with 1 N HCl and read using a SpectraMax M5 (Molecular Devices) at 405 nm. EC$_{50}$'s were calculated as the concentration at 50% of the maximum response from the linear range of a dose-response curve (EC$_{50}$= A$_{405,max}$−A$_{405,min}$/2). The % EC$_{50}$ values were calculated as the ratio of the EC$_{50}$ wild-type reference to the EC$_{50}$ variant (EC$_{50\text{-}WT}$/EC$_{50\text{-}variant}$*100%). Reported % EC$_{50}$'s are average values with each experiment being performed at least in triplicate and outliers, defined as values greater than three times the median, omitted.

Antibody stability analysis was performed by incubating duplicate samples of scAb variant or 1B7 IgG in PBS at 37, 50, and 4° C. for 24, 2, and 24 hrs, respectively. After incubation, the fraction of active antibody remaining was determined by ELISA and calculated with reference to untreated sample maintained at 4° C.

CHO cell clustering assays were performed by incubating 1039 pg/mL PTX with 100,000 molar excess scAb protein for ½ hr at room temperature in 96 well tissue culture plates. Freshly trypsinized confluent Chinese hamster ovary (CHO) cells were then seeded into the plates at a concentration of 10$^5$ cells/well. After 24 h of incubation at 37° C., a microscope was used to examine and score the wells based on clustering morphology on a scale of 0 to 3 with 0=no clusters and 3=all clustered, as described by Hewlett et al [29]. Final protective molar ratios were reported as the lowest ratio resulting in no clusters. The working concentration of PTx was determined from a preliminary toxin concentration series which resulted in scoring of 1 to 3 over the concentration range of 65-1039 pg/mL PTx. In order to observe this same range with protective scAb activity, the lowest concentration resulting in complete clustering was chosen along with a 100,000× molar ratio of scAb to PTx based upon CHO cell sensitivity to any free PTx.

Surface plasmon resonance (SPR) analysis was performed using a BIAcore 3000 instrument (GE Healthcare, Uppsala, Sweden). CM5 chips (GE Healthcare, Uppsala, Sweden) which contain carboxymethylated dextran covalently attached to a gold surface were used for all SPR experiments. After activation using a 50/50 solution of 1-ethyl-3-(3-dimethylaminopropyl)-carbodiimide hydrochloride and N-hydroxy-succinimide, the monoclonal antibody 1B7 was immobilized on the chip surface in 100 mM sodium acetate pH 5.0 until 750 response units was obtained at which point the reaction was quenched using 1.0 M ethanolamine-HCl at pH 8.5. Samples of the B-oligomer, PTx, PTx-S1, or PTx-S1-220 and variants in HBS buffer pH 7.4 with 3 mM EDTA and 0.005% Tween at five different concentrations between 50-3500 nM were run in duplicate over the chip with a 1 minute injection, a 5 minute dissociation, and a flow rate of 50 μL/min. A 30 second injection of 2 M magnesium chloride at 30 μL/min was used to regenerate the surface in between antibody injections. Baseline correction was calculated by subtracting simultaneous runs over a second flow cell which had been activated and quenched with no protein immobilized on its surface. The off-rates were calculated using BIAevaluation software (version 3.0) from Pharmacia Biosensor. Due to the low expression levels and varying purity of the PTx-S1-220 variants, the concentration dependent association and dissociation constants, $K_A$ and $K_D$, were not calculated. Instead, off-rates, which are typically very sensitive to amino acids changes and do not depend on precise concentration measurements, were compared. Reported values are the average and standard deviation of all off-rates calculated for each protein.

Fluorescence measurements were performed on a Molecular Devices SpectraMax M5 using 96 well special optics low fluorescence assay plates (Corning). Measurements were made on a 200 μL volume of 0.65 gm filtered samples diluted from stock in PBS. Excitation wavelengths of 278 and 295 nm were used for tyrosine and tryptophan, respectively. Emission spectra were recorded every nm from 330 to 460 nm. The emission spectrum for PBS was subtracted as background from all sample spectrums.

Immunoblotting (western blotting) was performed using samples electrophoresed on a 12% SDS-PAGE gel followed by transfer to a nitrocellulose filter using standard methods. All toxin samples were loaded at equimolar concentrations except truncated PTx-S1 which was loaded at approximately double concentration to compensate for impurities and cleavage. After blocking with 5% PBS-Tween-milk, the membrane was incubated with 1B7 monoclonal antibody, m1B7, or hu1B7 with scAbs at double the concentration of the monoclonal antibody for 1½ hrs. Secondary antibody, either peroxidase conjugated anti-mouse Fc or anti-human $C_k$ (Sigma), was then added for 1 hr with washing both before and after addition. The resulting bound protein bands were visualized using SuperSignal West Dura Extended Duration Substrate (Pierce) coupled with exposure to X-ray film.

Circular dichroism spectra from 300 to 190 nm were recorded on a JASCO-815 chiro-optical spectrometer at room temperature. A 1 mm path length quartz cell was used to take triplicate readings on 200 μL samples in PBS. A spectrum of PBS was taken and subtracted from each sample spectrum to correct for background. The average of the three spectra for each sample was used for secondary structure analysis using the JASCO software.

Computational Methods

Antibody modeling programs: Web Antibody Modeling (WAM), on the World Wide Web at antibody.bath.ac.uk/, predicts antibody structure from sequence data by finding template matches for the light and heavy chains separately and then fitting them together using conserved interface residues. Rosetta Antibody Beta, on the World Wide Web at antibody.graylab.jhu.edu/, searches the protein database (PDB) of crystal structures to find template matches and then utilizes Lennard-Jones potentials, a Lazaridis-Karplus solvation energy model, rotamer internal energies, and H-bonds to predict the antibody structure [31]. Z-dock, on the World Wide Web at zdock.bu.edu/, is a Fast-Fourier Transform based docking program used to generate initial docked models of the antigen, PTx-S 1, and antibody, hu1B7, from separate structural pdb files[32]. Once initial experimental data was collected, a pre-docked model was constructed manually, based on prior experimental data. RosettaDock, on the World Wide Web at graylab.jhu.edu:8088/, was then used to refine the model by optimizing side-chain and rigid-body orientation using a Monte-Carlo coupled with an energy function to return ten different models [33]. All probable docked models were submitted for further analysis using Rosetta computational alanine point mutagenesis, on the World Wide Web at robetta.bakerlab.org/, which replaces each residue with an alanine and computes the resulting interface energies [34, 35]. This results in identification of energetically important residues at the protein-protein interface for each docked model. Pepsurf, on the World Wide Web at pepitope.tau.ac.il/index.html, is a computational program that predicts both linear and conformational epitope based upon the crystal structure of the antigen and experimentally determined peptide sequences [36]. Six peptide sequences determined via phage screening of monoclonal antibody 1B7by the Cortese lab [37] were used in conjunction with the crystal structure of PTx [23] to predict the three "best clusters" on the toxin surface most likely to contain the desired epitope.

Example 2

Whooping cough is a serious illness in infants for which there is no known therapy for established disease. The disease is caused by the *Bordetella pertussis* bacterium, and is mediated by a number of virulence factors. One factor, pertussis toxin, is the primary component of an effective acellular vaccine, and polyclonal antisera has historically been used to treat infection (Scheinblum, et al., 1944). More recently, efforts to develop human hyperimmune antibody preparations (Granstrom et al., 1991; Bruss et al., 1999) have suggested that high anti-PT titres result in a more effective treatment (Bruss et al., 1999) and can even reverse established disease in a rodent model (Bruss and Siber, 1999).

The murine monoclonal antibodies 1B7 and 11E6 have been shown to be highly effective at treating pertussis infections in aerosol and intracerebral challenge mouse models (Sato and Sato, 1990). As a preliminary step in evaluating their potential as human therapeutics, Applicants cloned and expressed 1B7 and 11E6 as recombinant antibodies. Applicants also evaluated parameters that determine the success of antibody neutralization of pertussis toxin, in particular, the stability of these recombinant antibodies. Further, Applicants humanized the antibody binding site prior to production as a full-length humanized IgG.

The antibody variable regions were cloned and expressed using standard methods (Krebber et al., 1997). Humanization was based upon the method of Baca 110 (1997), in which the antibody CDR loops replace the CDRs of the human germline consensus sequence, and certain framework residues are retained with the murine identity. Screening by phage display of directed randomized libraries was used to identify humanized variants which retain binding capacity.

Antibody expression problems were solved by the use of a C-terminal protein fusion (HuCκ), and co-expression of the molecular chaperone, skp. Yields of purified protein increased from ~10 μg/L to almost 7 mg/L culture for the best-expressed variant. Pertussis toxin assays are much longer than anthrax toxin assays (48 hours for in vitro assays; 18 days for in vivo) magnifying the need for stable molecules. In contrast to the anti-PA antibodies, the anti-PT molecules are rapidly deactivated at 37° C., compromising their ability to protect cells in vitro. In fact, antibodies with the same affinity but dramatically different stabilities at 37° C., such as the 1B7 and 3A scAbs, required four-fold difference in antibody concentrations to provide equal protection. Similarly, an antibody with higher stability but lower affinity than 1B7, 1B7-Cys23, also required a four times higher concentration to provide equal neutralization as 1B7. Fab fragments of 1B7 that have been shown to be very stable and to have the same affinity as the 1B7 scAb, required nine-fold lower antibody concentration to protect cells as compared to the 1B7 scAb. Initial humanized constructs of 1B7 have been produced, but their affinity is greatly reduced (which is not surprising as the similarity between 1B7 and the human sequence is <50%). Targeted directed evolution followed by selection using phage display will most likely solve this problem.

Engineering Antibodies to Neutralize Pertussis Toxin

Figure 7:
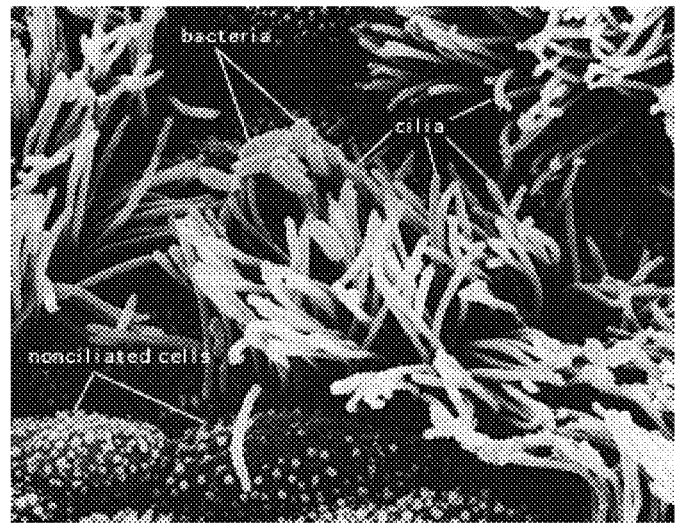

*Bordetella pertussis*, the etiologic agent of whooping cough, is a highly infectious human pathogen with a strong capacity to infect the human respiratory tract (Kerr and Matthews, 2000) (see FIG. 7). It is presently one of the ten most common causes of death from infectious disease, reported by the World Health Organization to cause 50 million cases per year (Kerr and Matthews, 2000). Infection occurs primarily in the unvaccinated populations in developing countries. While once effectively controlled in industrialized countries through vaccination, pertussis cases have been rebounding in the last ten years, due to decreased vaccination, antigenic drift (deMelker et al., 2000; Mooi et al., 2001) and transmission from adult reservoirs (Anonymous, 1995b; Deen et al., 1995; Senzilet et al., 2001).

A whole cell vaccine that has been used successfully for many years is currently being replaced by acellular vaccines. These are composed of inactivated toxins, primarily pertussis toxin (Jadhav and Gairola, 1999; Sato and Sato, 1999). Current care for infected individuals involves the administration of antibiotics, but this is only effective during the catarrhal phase, after which bacteria can no longer be cultured from the respiratory tract, and treatment is limited to supportive care. Of the ~9500 cases annually in the US, over half under one year of age, 70% were hospitalized, 20% contracted pneumonia, 3% experienced seizures, 0.9% experienced encephalopathy and 0.7% did not survive (Anonymous, 1995a). *B. pertussis* produces a number of adhesins and toxins which mediate virulence (Locht and Antoine, 1999) (see Table 6) and there is controversy as to which antigens confer protective humoral immunity (Oda et al., 1984; Taranger et al., 2000). However, administration of hyperimmune antibody preparations with high specific activity against pertussis toxin appears to be protective in humans (Bruss et al., 1999; Granstrom et al., 1991; Scheinblum and Bullowa, 1945) as does immunization with an acellular pertussis toxoid. Polyclonal anti-PT antibodies have even been shown to reverse established disease in mice (Bruss and Siber, 1999), suggesting that anti-PT antibodies may be therapeutically useful.

Figure 8:
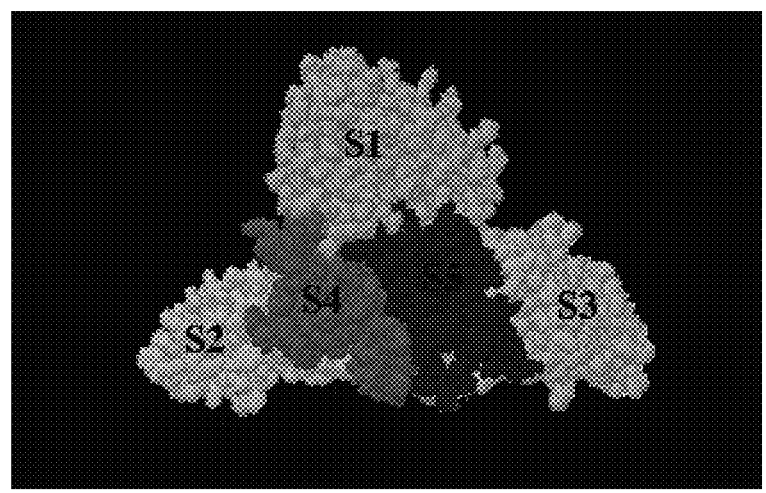

Pertussis toxin is a 105 kDa protein toxin, composed of an enzymatically active A subunit, and a B subunit primarily responsible for binding to the cell-surface. It is structurally similar to cholera and shiga toxins, conforming to the A-B5 class of toxins (Tamura et al., 1982). The toxin is an ADP ribosylase with specificity for Gi/o proteins (Katada and Ui, 1982; Hsia et al., 1984). The B domain of the pertussis toxin is composed of four unique proteins: a dimer of S2 and S4 subunits, a dimer of the S3 and S4 subunits, and S5. Together they form an asymmetric pentamer about a central pore. The active subunit, S1, sits atop the pore with its C-terminus penetrating halfway through the pore (see FIG. 8; Stein et al., 1994). The B subunit has been shown to bind with low affinity to N-linked sialoglycoproteins (van't Wout et al., 1992), including fetuin, haptoglobin, and transferrin. The S2 and S3 subunits each contain two binding clefts; an amino-terminal fold which resembles a family of mammalian calcium-dependent lectins, and a carboxy-terminal oligomer fold found in a number of proteins that bind carbohydrates (Stein et al., 1994). While no single universal receptor has been identified, pertussis toxin is capable of binding to all cell lines tested. Binding of the B region alone can result in cellular changes, including mitosis in lymphocytes and glucose oxidation in adipocytes, probably as a result of aggregating membrane proteins (Arciniega et al., 1987; Bibiero-Neto and Rodbell, 1989).

Figure 9:
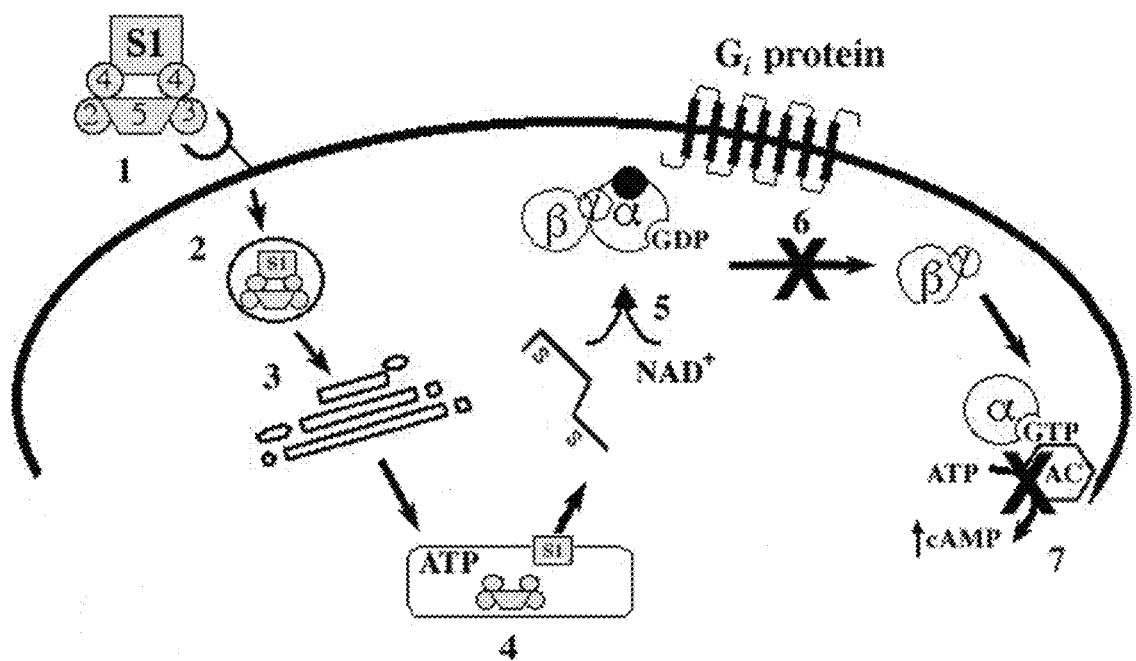
Figure 10:
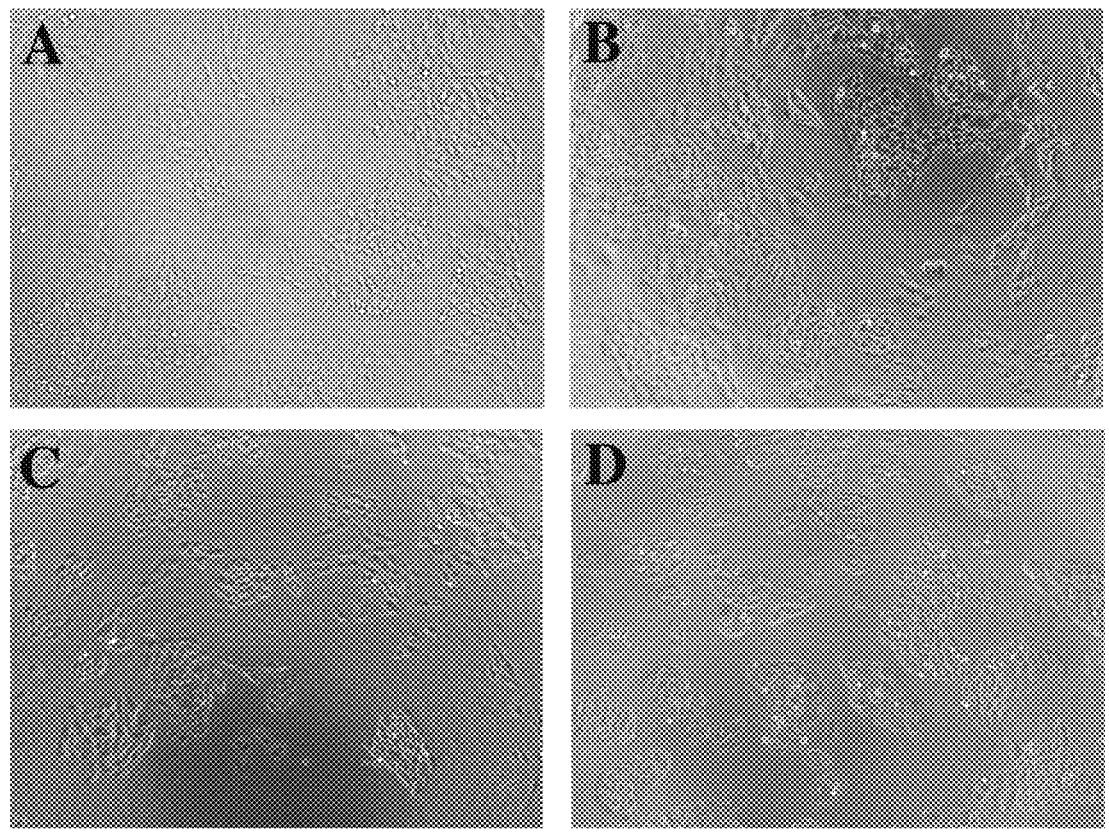
Figure 11:
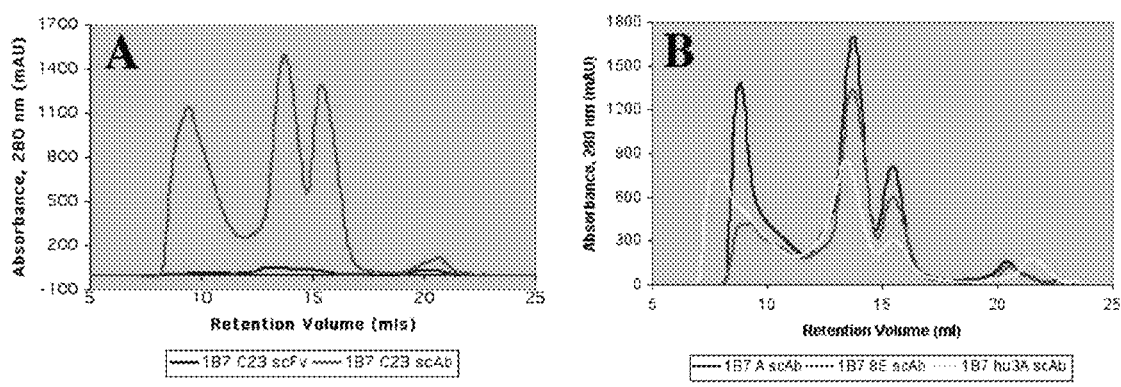
Figure 12:
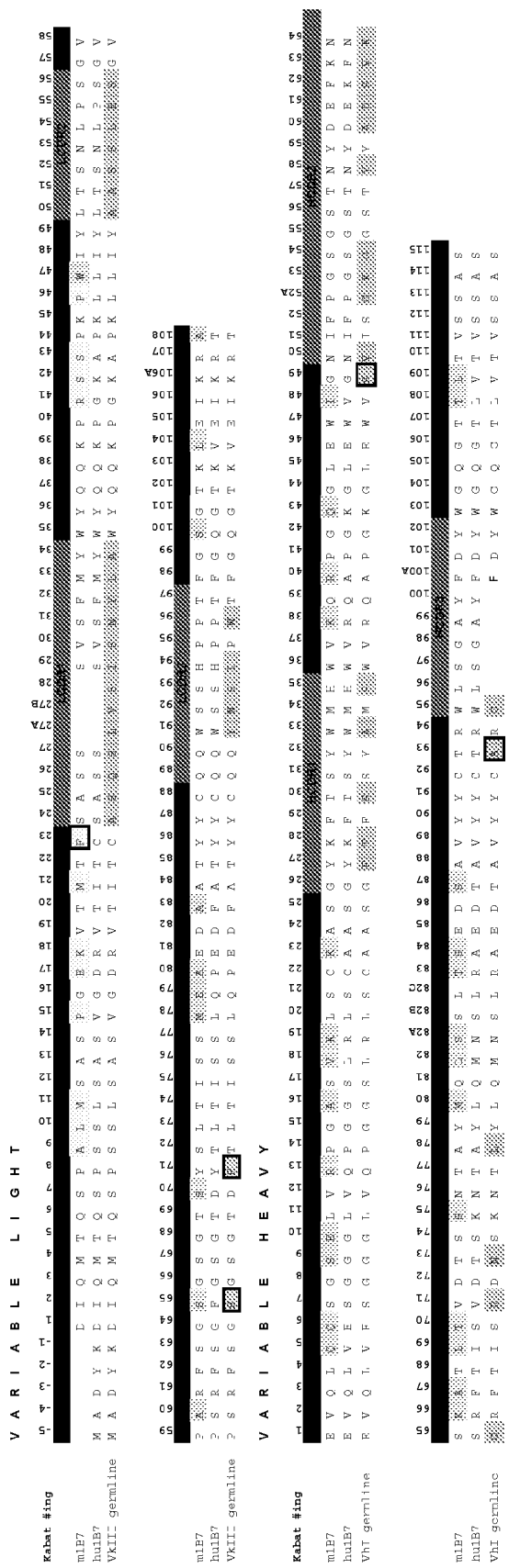

Cellular entry of the toxin is thought to be via endocytosis and retrograde transport (Xu and Barbieri, 1995; el Baya et al., 1997), most likely to the endoplasmic reticulum. In this organelle, ATP and a reducing environment are present, enabling the S1 subunit to dissociate and unfold (Kaslow et al., 1987), exposing its active site and a phospholipid binding domain which is thought to facilitate direct translocation into the cellular cytosol. Here, the S1 subunit catalyzes the transfer of an ADP-ribose from NAD+ to cysteine-351, near the N-termini of $\alpha$ subunits of inhibitory and olfactory G proteins and transducin (Bokoch et al., 1983). This modification blocks the G protein inhibition of adenylate cyclase (Katada and Ui, 1982), and the G proteins lose their signal transducing ability (See FIG. 9). This modification has a number of effects in vivo, including stimulation of insulin secretion, histamine sensitization and lymphocytosis (Tamura et al., 1983), and in vitro modifies CHO cellular morphology, inducing growth in small clumps (Hewlett et al., 1983). Several excellent reviews on the mechanism of pertussis toxin have been published, to which the interested reader is referred (Gierschik, 1992; Kaslow and Burns, 1992; Locht and Antoine, 1999; Locht, 1999).

Human or humanized antibodies that block the action of pertussis toxin represent a potential therapeutic for the specific treatment of pertussis in conjunction with antibiotic therapy. Previously, Williamson and Matthews (1999) reported the cloning of three unique anti-pertussis toxin scFvs from the circulating B lymphocytes of human volunteers recovering from *B. pertussis* infections. These scFv, when displayed on filamentous phages, were shown to neutralize PT in an in vitro assay. However, the antibodies were not analyzed as purified proteins, nor have their affinity and epitopes been characterized. Thus, their potential as therapeutic agents is unclear. In contrast, a large number of murine monoclonal antibodies have been produced and extensively characterized (Anwar et al., 1987; Frank and Parker, 1984; Halperin et al., 1991a; Halperin et al., 1991b; Kenimer et al., 1989; Kim et al., 1989; Lang et al., 1989; Shahin et al., 1990; Walker et al., 1991). Among the more promising of these monoclonal antibodies, on the basis of protection in in vitro and in vivo mouse models, are the 1B7 and 11E6 antibodies produced by Sato and Sato (Sato et al., 1984; Sato and Sato, 1990).

The 1B7 antibody binds to the catalytic S1 subunit, inhibiting enzymatic activity, and has been shown to be protective in the in vitro CHO cell assay, as well as in in vivo intracerebral and aerosol challenge experiments (Sato et al., 1984). 11E6 binds to the S2 and S3 subunits, blocking binding and entry of the toxin into cells. 11E6 has been shown to be protective in vitro, but in vivo only in the aerosol model (Sato and Sato, 1990). The co-administration of these two antibodies has been shown to be synergistic and to be as potent as conventional polyclonal antibody therapy (Sato and Sato, 1990). One-hundred percent of mice survived an aerosol challenge when 2.5 µg 1B7 and 7.5 µg 11E6 were administered two hours prior to aerosol challenge with *B. pertussis*, compared with 17% given PBS and 70-84% given 5 µg either 1B7 or 11E6 alone (Sato and Sato, 1990). Here, Applicants describe the cloning and characterization of these two murine hybridomas, their in vitro neutralization of pertussis toxin, and the humanization of 1B7. Humanization, the grafting of CDR loops from the murine antibodies onto a human antibody framework is a key step in the development of these antibodies as a potential human therapeutic, as humanization greatly reduces the risk of inducing a human anti-mouse antibody (HAMA) response.

Methods

Cloning from hybridomas The heavy and light variable chain regions were cloned from two anti-PT hybridomas (1B7, 11E6) via RT-PCR exactly as described by Krebber et al. (Krebber et al., 1997). VH and VL genes were joined by overlap PCR and cloned into pAK100 phage display vector using 5' and 3' SfiI sites. Single colonies in *E. coli* strain TG1 were grown in a 96-well plate, and phage displaying scFv were produced. Phage from single colonies were screened by direct ELISA: after overnight coat with 50 μl 0.5 μg/ml PA in 0.05 M sodium carbonate buffer pH 9.6, plates were blocked for two hours with 5% milk in PBS, then coated with 50 μl phage plus 50 μl 2% milk in PBS for 1.5 hours. Plates were washed three times with PBS-0.05% Tween-20, and bound phage detected with anti-M13 (1:3000, AmershamPharmacia) for 1.5 hours. After a final wash, signal was developed with 50 μl OPD substrate (Sigma) and quenched with 50 μl 4N H2SO4.

Expression and purification scFvs were subcloned from the phage display vector pAK100 via SfiI-SfiI restriction sites into the following expression vectors: pAK300 for scFv expression or pMoPac16, a pAK400 derivative for scAb expression (scFv with a C-terminal human constant kappa domain fusion) and co-expressing the periplasmic chaperone, skp, which is known to assist with recombinant antibody expression in *E. coli* (Bothmann and Pluckthun, 1998; Hayhurst and Harris 2000; A. Hayhurst, unpublished results). All expression and purification steps were performed exactly as described in Chapter 2.

Humanization Humanization was accomplished by total gene synthesis (Stemmer et al., 1995) of the scFv gene using 38×40-mer oligonucleotide primers (see Table 7) synthesized by Midland Certified Reagent Company (Midland, Tex.) at a 50 μM scale with standard purification. Each primer was diluted to 100 μM with 10 mM Tris pH 8.0, 1 mM EDTA and equal volumes combined such that each primer is present at 2.5 μM. Separate primer mixtures were prepared to assemble the VH and VL genes individually (preliminary analysis found this to be a more reliable approach than assembling the entire gene at once). Each primer mix was diluted 1:100 in 50 μl PCR mix without outside primers (10 mM Tris pH 8.5, 1.5 mM MgCl2, 50 mM KCl, 0.2 mM each dNTP, 5 units Taq polymerase) and cycled on an MJR DNA Engine for 45 cycles of 94° C. for 30 seconds, 45° C. for 30 seconds, 74° C. for 60 seconds to assemble the gene. Agarose gel electrophoresis (1.5% w/v in TAE buffer) showed the presence of primary bands at 350 bp (VL) or 400 bp (VH). The genes were amplified by diluting the assembly reaction 1:40 in PCR mix with either light or heavy gene specific outside primers from the Plückthun primer set (Krebber et al., 1997) (10 mM Tris pH 8.0, 1.5 mM MgCl2, 50 mM KCl, 0.2 mM each dNTP, 2.5 units Taq polymerase, 1 μM each outside primer). The amplification cycle consisted of 30 cycles at 94° C. for 60 seconds, 52° C. for 60 seconds, and 74° C. for 75 seconds. Bands corresponding to the heavy and light chain variable regions were purified by gel electrophoresis (1.5% w/v agarose; the appropriate band was cut out, frozen at −80° C. for at least five minutes in a 1.5 ml eppendorf tube, thawed and centrifuged at 14K rpm for 10 minutes). The gel supernatant was used at a 1:40 dilution as DNA template. A final cycle to overlap the genes was performed as above in a 400 μl volume, except that both heavy and light chain DNA was included in the reaction mixture and the outside primers used were 5' scFv VL SfiI and 3' scFv VH SfiI. The full-length product (~750 bp) was concentrated using Qiagen columns, digested with SfiI, gel purified (Qiagen), and cloned into the scFv expression vector, pAK100, for screening by phage display to identify active clones. DNA sequencing (using a di-deoxy terminator protocol) confirmed the sequence of individual clones.

Preparation of monoclonal antibody and Fab Fragments Hybridomas were grown in serum-free media (Gibco-BRL) for ~1 month. Antibodies were precipitated from 100 mls tissue culture supernatant with 50% saturated ammonium sulfate overnight at 4° C., centrifuged for 30 minutes at 3000 rpm, and the pellet resuspended in protein G binding buffer (0.1 M sodium acetate, pH 5.0). Antibodies were dialyzed overnight against three changes of protein G binding buffer to remove ammonium sulfate and applied to a recombinant Protein G column (Pierce) via an ÄKTA FPLC (Amersham Pharmacia). Antibodies bound to the column were eluted using low pH Protein G Elution Buffer (Pierce) and immediately neutralized by the addition of 1 M Tris, pH 8.5. Antibodies were dialyzed against three changes of PBS and concentrated to ~10 mg/ml using Centricon-30 columns. As a final step, antibodies were applied to a size exclusion chromatography column (Superdex 200, Amersham-Pharmacia) to remove aggregates.

Fab fragments were prepared by a 4 hour digestion at 37° C. with papain (10 μg papain/mg immunoglobulin in PBS-1 mM EDTA-20 mM cysteine). The digest was diluted 10-fold in high salt protein A binding buffer (1.5 M Glycine, 3 M NaCl, pH 8.9) and applied to a recombinant protein A column (Sigma) via an ÄKTA FPLC. The use of a high salt buffer enhances the otherwise weak interaction between Protein A and murine IgG1 antibodies (Harlow and Lane, 1988). Flowthrough contained the Fab fragments, while the Fc and intact IgG were retained by the column. The column was regenerated with Protein A elution buffer (0.5 M acetic acid, pH 2.5 or 0.1 M Glycine, pH 2.8), followed by binding buffer to neutralize the pH. The absence of contaminating Fc and intact IgG was confirmed by a direct ELISA, as described in Chapter 2. Briefly, ELISA plates were coated with the Fab fraction, followed by blocking (5% milk in PBS) and detection with either rabbit-anti-mouse-Fc-HRP (Pierce) or rabbit-anti-mouse-F(ab)2-HRP (Sigma). F(ab)2 fragments were prepared by digestion with pepsin (in 0.1 M citric acid, pH 3.5; 5 μg/ml pepsin per mg antibody, overnight at 37° C., reaction quenched by the addition of 1/10 volume 1M Tris ph 8.5); F(ab)2 was separated from intact immunoglobulin by separation on a Superdex-200 size exclusion column. Concentrations were determined by the BCA assay (Pierce), using BSA as a standard.

Equilibrium Affinity Analysis by Competition ELISA Affinity was measured by the method of Friguet et al. (1985). A high binding ELISA plate (Costar #3595) was coated overnight at 4° C. with 0.5 μg/ml unactivated PT (Sigma #P-7208), and was blocked along with an uncoated plate for two hours with PBS-5% milk at room temperature. The uncoated plate was washed, and PT serially diluted in 50 μl PBS-milk from 50 nM to 0.4 nM. The last row contained no PT. In separate tubes, antibody preparations were diluted to 10 nM in PBS-milk, and 50 μl applied to each well in triplicate (final concentrations 5 nM antibody, 25 nM pertussis toxin in row A). This plate was allowed to reach equilibrium at 25° C. for two hours before being transferred to the coated and blocked plate. Antibody binding to coated PT was detected by rabbit-anti-mouse-Fab (Pierce, 1:3000), followed by goat anti-rabbit-HRP (Pierce, 1:3000). Signal was visualized with 50 μl OPD substrate (Sigma) and quenched with 50 μl 4 N H2SO4. Wells were read as the absorbance at 490 nm minus the background absorbance at 405 nm. Data were analyzed as described (Djavadi-Ohaniance et al., 1996), using a Scatchard plot of [Ab:Ag]/[Abt]/[Ag] versus [Ab-Ag]/[Abt] in which the slope is equal to 1/Kd.

Figure 13:
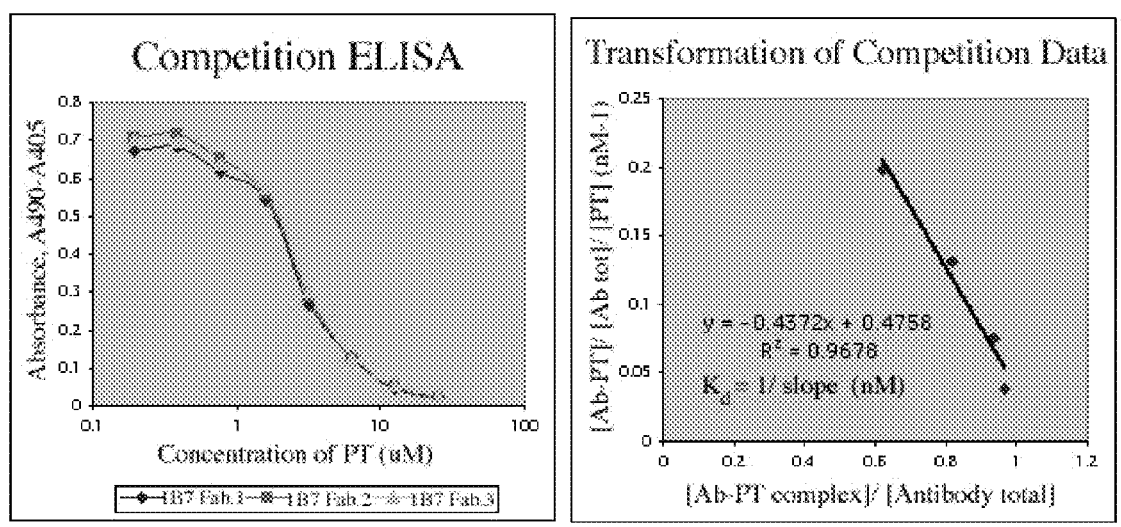

Surface plasmon resonance could not be used to measure the binding kinetics because of issues specific to the pertussis toxin system. Preliminary analysis demonstrated that the pentameric protein can be coupled to a chip via EDC-NHS chemistry, but the conditions (2-4 M magnesium chloride) used to remove bound antibody at the end of a run also dissociated the toxin subunits, complicating subsequent runs. Moreover, the subunit of primary interest for 1B7 variants, S1, contains no lysines and is therefore not available for NHS-EDC coupling. Attempts to express and purify active S1 with a lysine containing tag were not successful (data not shown). Strategies to prevent the dissociation of the toxin after coupling to the chip; i.e. crosslinking with glutaraldehyde, were not pursued out of concern that key epitopes might be altered.

In vitro neutralization assay The CHO clustering assay was performed as previously described (Gillenius et al., 1985; Hewlett et al., 1983). CHO-K1 cells (ATCC #CCL-61) were grown to confluence in Ham's F12K media (Sigma) supplemented with 10% FBS and gentamicin at 37° C. and 5% CO2. Just prior to use, they were trypsinized and diluted to 2×105 cells/ml. To determine the sensitivity of the assay, PT was serially diluted in 50 μl media across a 96-well cell culture plate, and 100 μl/well CHO cells were added. After 48 hours, cells were examined by phase contrast light microscopy with 10× magnification. The transition from normal to clustered growth was found to occur at pertussis toxin concentrations of ~0.03 ng/ml (see FIG. 10).

To determine antibody neutralization of PT, a sterile-filtered (0.22 μm) antibody preparation was diluted in media with toxin (10 ng/ml=0.095 nM) to 14.5 μM. Antibodies were then serially diluted in 2-fold steps in a 96-well cell culture plate with 50 μl media containing PT (10 ng/ml). After incubation of antibodies with toxin for 2 hours at 37° C., 100 μl media with cells (2×105/ml) were added (final concentration of PT is 3.3 ng/ml; antibody dilutions start at 4.8 μM). After 48 hours of growth at 37° C., 5% CO2, cells were examined by light microscopy. Wells were scored for the absence of clustering (normal morphology), the presence of mixed normal and clustered groups of cells (transition region), and the presence of only clustered cells (clustered morphology; see FIG. 10). Because the transition region is apparent over several antibody concentrations, it is difficult to determine the concentration that completely neutralizes the toxin (i.e., no clustering). In contrast, the minimum protective concentration (the concentration at which only clustering morphology is seen) is fairly easy to determine. For this reason, the concentration above which antibodies begin to protect the cells is reported (see Table 8).

Results

Cloning and expression The variable heavy and variable light chains of the 1B7 and 11E6 antibodies were cloned into an scFv format as described in the Materials and Methods section. Because of the greater neutralizing ability of 1B7 in previous aerosol challenge experiments and intracerebral mouse models, this antibody was selected for humanization and is the focus of this chapter. Expression of both antibodies proved to be very problematic, an issue that plagues many antibody engineering studies (Hayhurst and Harris, 1999; Hayhurst 2000). A possible explanation for the poor expression of 1B7 is the presence of an unusual L23Phe instead of a conserved cysteine in light framework one. This 1B7 scFv was very poorly expressed in the bacterial periplasm, with purified yields of approximately 10 μg/L culture in the expression vector pAK300. By comparison, yields 50-100 times greater were obtained for the 14B7 anti-PA scFv antibody (see Chapter 2). It was hypothesized that the poor expression of the 1B7 antibody was due to the missing cysteine, thus, this residue was restored by primer mutagenesis as described in Chapter 3. The resulting mutant antibody could be produced at a 20-fold higher yield. However, FPLC of the purified antibody following purification by metal affinity chromatography indicated that the scFv had a strong tendency to oligomerize in solution. To prevent oligomerization by shielding exposed hydrophobic patches of the variable fragments, the 1B7 recombinant antibody fragment was expressed as a scAb by fusion a human Cκ chain. This modification resulted in a drastic reduction in the propensity of the antibody to multimerize (see FIG. 11). To further increase the yield of correctly folded scAb antibody, the scAb gene was expressed from a plasmid co-expressing the *E. coli* periplasmic chaperone skp. Co-expression of skp has been shown to markedly increase the yield of several antibody fragments in bacteria (Bothmann and Pluckthun, 1998; Hayhurst, 2000). Indeed, the HuCκ-skp combination resulted in a dramatic increase in the expression of the 1B7 scAb. A purified protein yield of 6.8 mg/L culture was obtained from bacterial cultures grown in shake flasks. Thus, the reintroduction of the conserved cysteine residue, expression as a scAb, and co-expression of the skp chaperone resulted in a nearly 1000-fold higher expression relative to the original construct (see FIG. 11). The 11E6 antibody also expressed quite poorly as an scFv in pAK300, and yields increased dramatically when expressed as a scAb with the co-expression of skp (see Table 8, page 129).

Humanization To transfer the specificity of the 1B7 antibody to a human framework, the 1B7 CDR loops were grafted onto a human antibody framework (see FIG. 12) (Vaughan et al., 1998). The human framework selected for this study, VLκ subgroup I (VLκI) and VH subgroup III (VHIII), is derived from consensus sequences of the most abundant human subclasses. It is therefore less likely to induce an immune response in human recipients than other frameworks, which have been based on human myeloma lines (i.e., NEWM, KOL, REI). Lastly, this framework has been used successfully by several groups, including the development of several FDA approved antibody therapeutics (Baca et al., 1997; Jung and Pluckthun, 1997; Presta et al., 1997; Presta et al., 1993; Werther et al., 1996). It should also be noted that the selected human framework has been demonstrated to give good yields of stable antibody when expressed recombinantly both in *E. coli* and in eukaryotic systems.

During the humanization process, it is typical that several non-CDR residues must be restored to their murine identity in order to retain the original level of antigen affinity. Based on the collective literature from studies using the VLκ and VHIII sequences, it has been observed that the framework residues that most often influence binding are consistently derived from a set of 11 residues (Baca et al., 1997). Therefore, the murine identity of these residues was retained in the initial humanized antibody construct of 1B7 (hu1B7). The sequence of the murine 1B7 antibody, its humanized counterpart, an antibody successfully humanized using these frameworks (4D5; Carter et al., 1992), and the germline consensus regions for VLκ and VHIII are shown in FIG. 12 below.

Affinity Antigen binding affinity was determined by competition ELISA using the method of Friquet et al. (1985; see FIG. 13). Affinity measurements compared well with previously reported measurements: previously, Nencioni et al. (1990) reported a Kd of 4.2 nM by radioimmunoassay for the 1B7 mAb. In this work, the affinity of 1B7 was determined to be 1.1±0.2 nM, which is similar to the previous measurement, given experimental errors between different methods and different preparations of antibody. The 1B7 Fab and scAb variants appear to be of similar affinity, about 2 nM, with the exception of the 1B7-Cys23 that has reduced affinity, about 8 nM. The 11E6 Fab and scAb fragments also appear to be of similar affinity, about 20 nM. Preliminary humanized constructs of 1B7 have been produced and confirmed by sequencing, but their affinity is significantly reduced, as determined by ELISA reactivity. See Table 8 for complete results.

Figure 14:
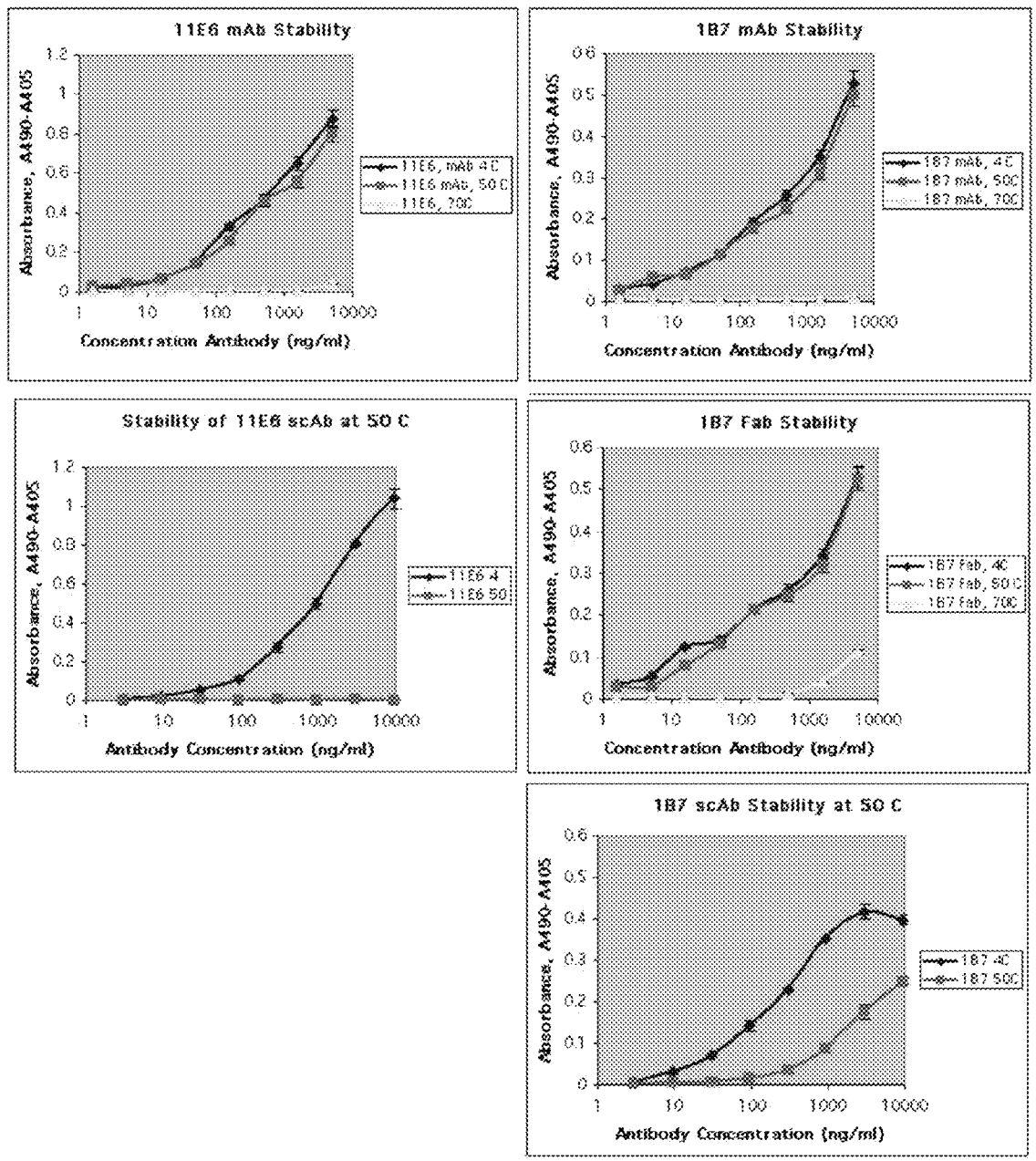
Figure 15:
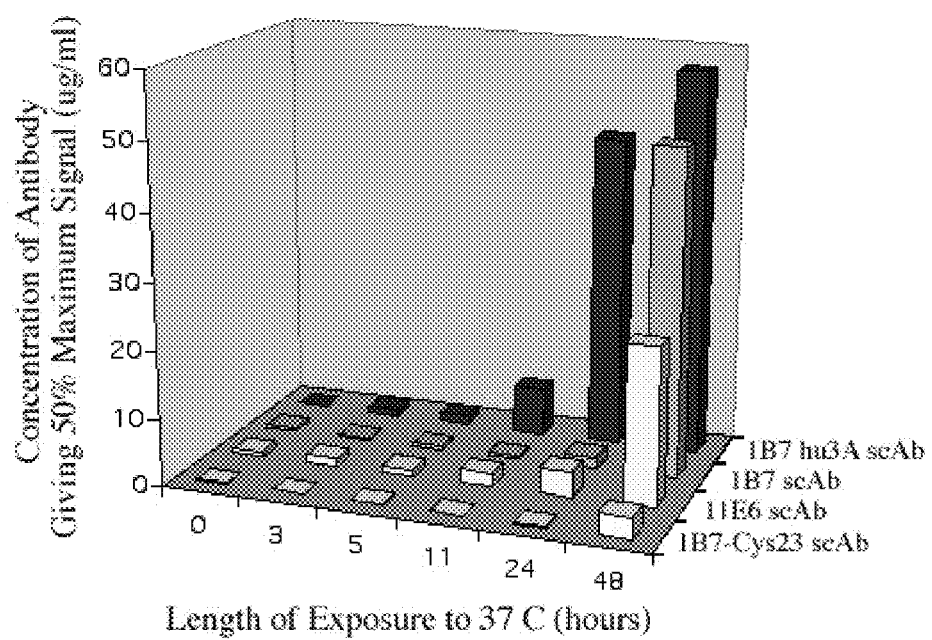
Figure 16:
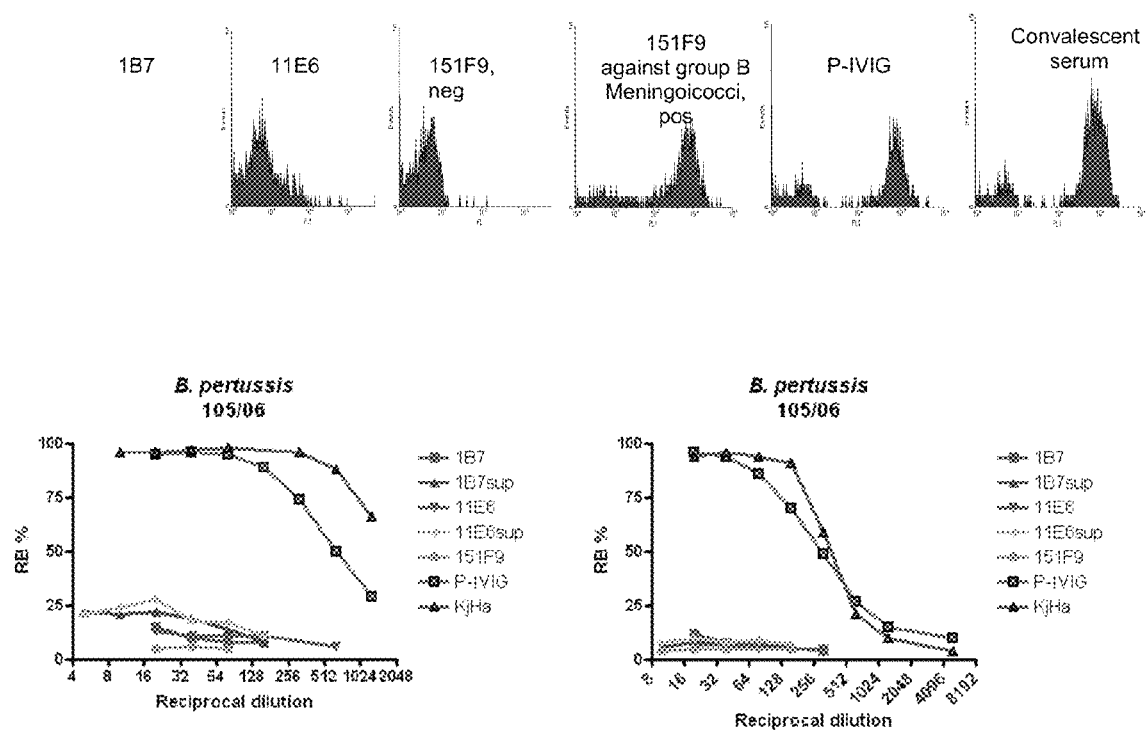
Figure 17:
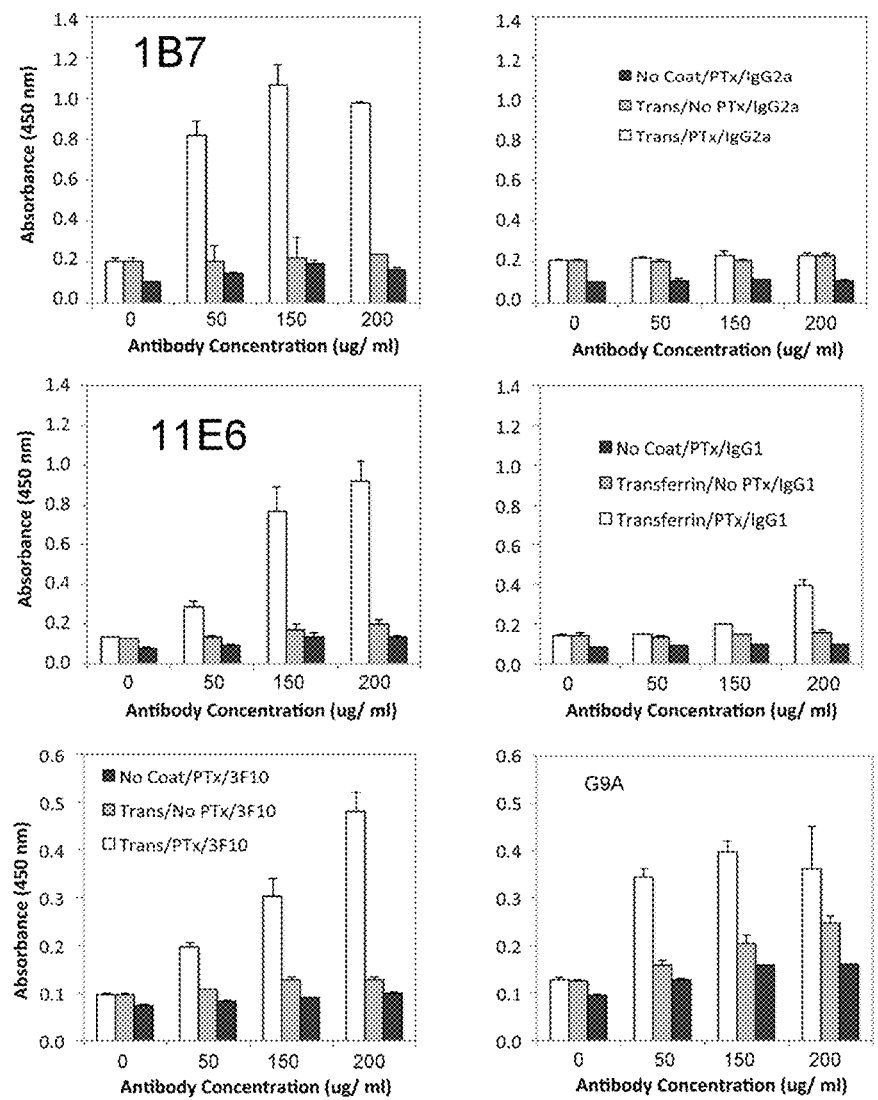
Figure 18:
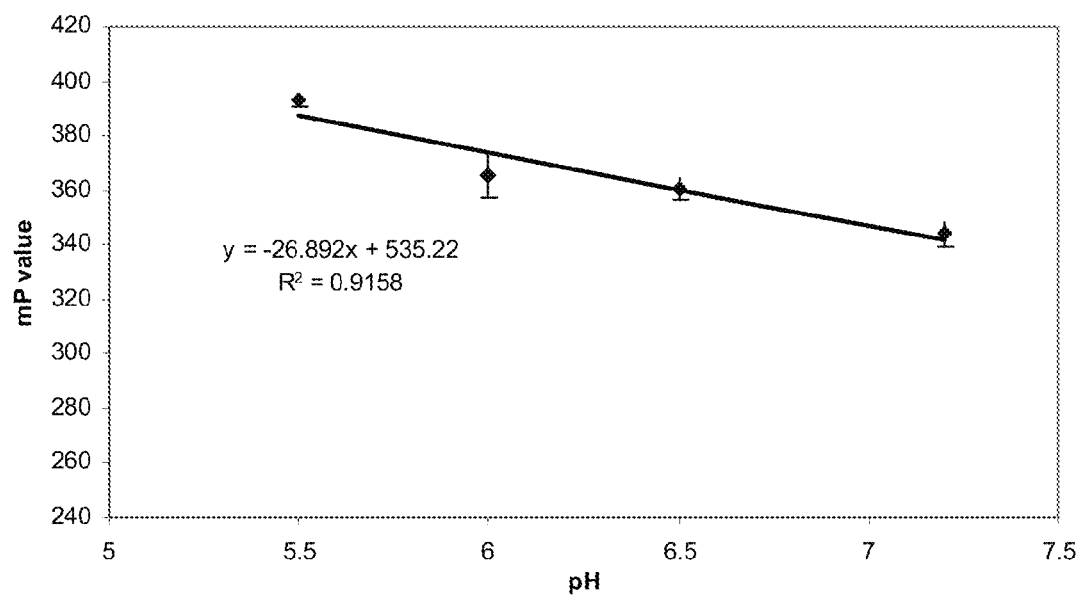
Figure 19:
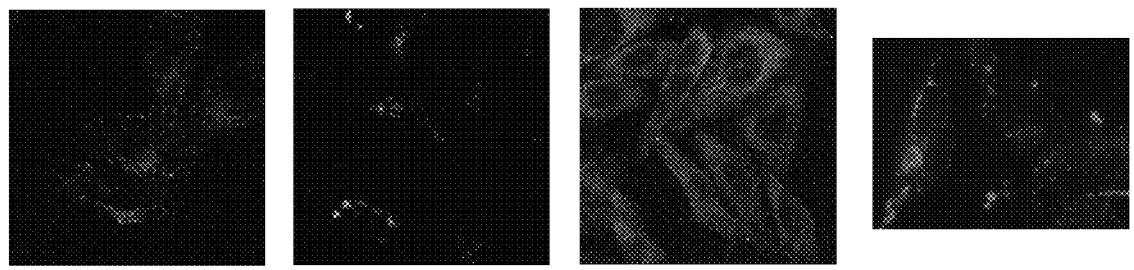
Figure 20:
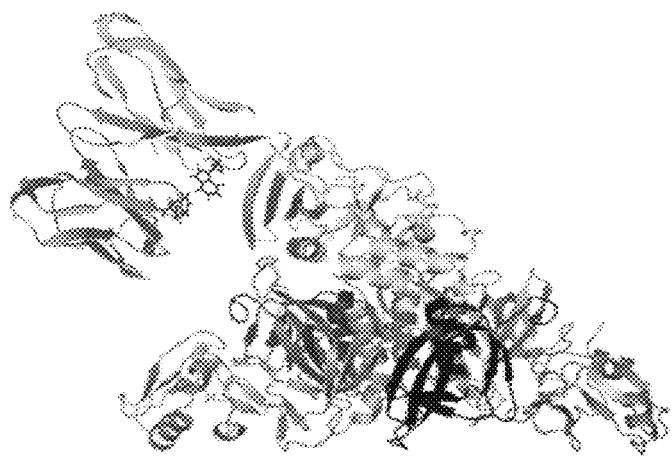

Stability Compared with other monoclonal antibodies (i.e., the 14B7 anti-PA antibody and its derivatives; see Chapter 2), the anti-PT antibodies are significantly less stable. After a two hour incubation at 70° C., the parental 1B7 and 11E6 antibodies and their respective Fab fragments are reduced to 0.1-1% activity compared to controls maintained at 4° C., as measured by reactivity in an indirect PT ELISA (see FIG. 14). Less stringent conditions, two hour incubations at 50° C., did not affect mAb and Fab reactivity, but completely abolished scAb activity.

To assess scAb stability in a setting relevant to in vitro and in vivo experiments, pertussis binding activity was examined after 0, 3, 5, 11, 24, and 48 hour incubations in PBS at 37° C. Variations in stability were seen for the three 1B7 scAb variants tested. The 1B7 variant with a restored cysteine 23 (1B7-Cys23) retained the greatest PT binding activity after all treatments, consistent with previous reports in which disulfide bonds have been shown to be critical for scFv stability (Glockshuber et al., 1992). The wild-type 1B7 and 11E6 scAbs were less stable, losing activity rapidly after 24 hours at temperature. 1B7 variant 3A was particularly unstable, exhibiting detectable losses in activity after only 3 hours at 37° C. (see FIG. 15).

In vitro neutralization All antibody fragments tested were able to block toxin action and prevent the CHO cell clustering morphology in a 48 hour experiment. The minimum protective concentration of antibody (the minimum concentration at which protection occurs and normal morphology appears in combination with clustering) is reported, as this is least ambiguous and most reproducible transition (see Table 8). The parental monoclonal antibodies protected better than other fragments (about 8-fold), presumably as a result of bivalency. This idea is reinforced by the fact that the 1B7 F(ab)2 also protects better than the 1B7 Fab. The mAb and F(ab)2 values, while similar, do not agree exactly, most likely as a result of experimental error (see Table 8).

Surprisingly, even though Fab and scAb fragments have very similar affinities, as measured by competition ELISA, their in vitro neutralization profiles are remarkably different. This is most likely due to differences in stability, which are significant on the 48-hour time scale of the experiment. In fact, all scAb variants tested lose activity rapidly after ~24 hours at 37° C. The most resistant variant, 1B7-Cys23 scAb, only retains about 8% activity as measured by ELISA after a 48 hour incubation. Interestingly, 1B7 scAb variant 3A which exhibited identical affinity, but substantially reduced stability at 37° C. (after only 3 hours, activity was reduced to 21%), protected less well than the parental scAb (minimum protective concentrations of 1500 and 377 nM, respectively). The rapid deactivation at physiological temperatures severely compromised scAb neutralization abilities, and indicates that the humanized binding site needs to be produced as an intact IgG prior to in vivo studies with a mouse model. This data further emphasizes the notion that stability is a key parameter which must be addressed when developing antibody therapeutics.

A point which deserves attention regards the CHO clustering assay itself. While this assay is extraordinarily sensitive, is suffers from being highly subjective and qualitative, particularly as there is no clear transition between protected and unprotected cells, but a gradual transition over several two-fold dilution steps (see FIG. 10). This assay has been standardized as a method to detect and quantitate serum antibody levels to pertussis toxin (after vaccination or infection; Gillenius et al., 1985) and is widely used. However, assays based on objective, quantifiable outcomes that do not require the use of radioactivity could be developed and would represent a significant advance over available assays. In particular, the establishment of a stable CHO cell line containing a reporter gene (e.g., destabilized enhanced green fluorescent protein (d2EGFP)) under a cAMP responsive promoter could couple cellular intoxication to a fluorescent signal. Previous reports (Katada and Ui, 1981; Hazeki and Ui, 1981) demonstrated cAMP accumulation in whole cells after exposure to pertussis toxin concentrations of 0.01-10 ng/ml when cAMP breakdown was prevented by the addition of 1 mM methylxanthine (3-isobutyl-1-methylxanthine, IBMX). cAMP levels were measured by a radioactive assay, and found to increase 2-4-fold. Control experiments could include treatment with forskolin (which activates adenylate cyclase to increase cAMP levels) and mastoporan/compound 48/80 (which inhibits pertussis toxin ADP-ribosylation; Tomita et al., 1991). Whole populations could be analyzed by flow cytometry or in opaque 96-well plates with antibody titrations in the presence of a fixed concentration of pertussis toxin. A second reporter gene under a constitutive promoter could be used to normalize for the number of cells seeded in each well of a 96-well plate. Such an assay would prove useful not only for the analysis of pertussis toxin, but also other toxins which affect cAMP levels (i.e., cholera toxin, anthrax edema factor, and pertussis adenylate cyclase). Some attempts have been made to develop this assay, but have not been completed.

The 1B7 antibody has been previously demonstrated to be successful in neutralizing pertussis toxin and thus preventing full manifestation of the disease. As a first step in evaluating the potential of this antibody as a human therapeutic, Applicants have cloned this antibody, expressed it in *E. coli* and engineered a humanized form. The humanized version of 1B7 was engineered using total gene synthesis by oligonucleotide primers followed by phage display to isolate functional clones (Baca et al., 1997). As acceptor frameworks, Applicants chose the VHI and VκIII germline sequences. These are the most common germline sequences in the human population (Walter et al., 1995) and because they have not been rearranged, are far less likely to induce immune responses than the rearranged myeloma genes used previously (i.e., NEWM, KOL, REI). Moreover, these frameworks have been successfully used numerous times by workers at Genentech and elsewhere (Baca et al., 1997; Carter et al., 1992; Presta et al., 1997; Presta et al., 1993; Werther et al., 1996; Wu et al., 1999).

Both the scFv and scAb antibody forms were shown to be capable of neutralizing pertussis toxin in vitro, as determined by the CHO cell clustering assay. Stability was shown to be an important determinant of neutralizing ability in these studies, and is able to at least partially compensate for differences in affinity. In future studies, the humanized version of the 1B7 antibody will be cloned into plasmids containing FDA-approved human constant regions, to produce antibody in transiently transfected CHO or NSO cells. These molecules would be appropriate for use in mouse aerosol challenge studies, to determine the protection conferred by a humanized 1B7 as compared to the parental 1B7 IgG and polyclonal anti-PT sera.

Hyperimmune human sera has previously been shown to be promising for treating pertussis in human clinical trials (Bruss et al., 1999), but is no longer being produced. Applicants anticipate that a humanized version of 1B7 may be more effective than hyperimmune sera due to its higher specific activity, analogous to work with tetanus toxin in which 0.7 mgs of two monoclonal antibodies provided similar protection as 100-170 mg of a polyclonal preparation (Lang et al., 1993). Furthermore, because a continuous source of antibody is available from immortal cells lines, a humanized 1B7 IgG may eventually prove useful for the clinical treatment of pertussis.

Example 3

Pertussis is a growing problem in industrialized countries with a five-fold increase in reported cases in the US alone from 1995-2005 (51). Vaccination, while able to the prevent severe manifestations of disease, has been unable to eliminate asymptomatic carriage of bacteria. In fact, the general wane in immunity post-vaccination has resulted in a change in disease demographics with adults and adolescents now predominantly constituting the carrier population (141, 159). Although the disease is typically only manifested as subclinical infection in this group, it is easily spread to more susceptible groups including infants, elderly, and immunocompromised individuals who are then left with only supportive care, since antibiotics are ineffective past the catarrhal stage (137, 167).

Part of the difficulty in treating or vaccinating against pertussis is the fact that of the several virulence factors associated with the bacteria there are no clear correlates of protection. Pertussis toxin (PTx) has been shown to be a major protective antigen as it is not only included in all acellular vaccines but is also used as a marker in serological diagnosis of the disease (134). It is an AB type toxin which includes cholera toxin (CT), ricin, shiga toxin (ST), shiga-like toxins (SLT), heat labile enterotoxin (LT), and *pseudomonas aeruginosa* exotoxin A (ExoA). These toxins consist of a catalytically active A subunit attached to a receptor binding B subunit. Upon binding to cell surface receptors, they undergo receptor mediated endocytosis followed by retrograde transport to the Golgi and the ER. Here the disulfide bond either attaching the A and B subunits (ricin and ExoA) or an internal disulfide bond within the A subunit (CT in the Golgi, ST, and SLT) is reduced resulting in the release of the A subunit and its subsequent escape into the cytosol (96, 120, 162). PTx has been shown to follow this same retrograde pathway with the release of its A subunit hypothesized to occur upon ATP binding to the pore of the B-subunit while in the ER (95). The exact mechanisms of PTx trafficking to the ER and escape into the cytosol is yet to be determined.

Due to its high immunogenicity and clear role as a major protective antigen, several anti-PTx antibodies have been generated and characterized. Serum from vaccinated adult volunteers was pooled and used for passive immunization studies which resulted in a reduction in the length and severity of the cough in Phase I trials. However, it proved inconclusive in further Phase III trials with human infants (61, 62, 85). This is because most antibodies elicited upon vaccination with PTx recognize non-neutralizing epitopes. Through extensive mouse studies, rare highly neutralizing antibodies such as 1B7 and 11E6 have been isolated and extensively characterized resulting in the identification of four major neutralizing epitopes on the toxin. Antibodies recognizing these epitopes either block the binding of the B-oligomer to the cell surface receptors or block catalysis by preventing the dissociation of the two subunits.

Of these rare antibodies, 1B7 has been shown to be potently neutralizing as it alone was able to not only protect mice from disease, but also reverse it after 7 days of infection (151). Its mechanism was originally thought to consist in the prevention of ADP-ribosylation by blocking substrate access to the catalytic site (64, 71, 107). However, now that more is known about the retrograde transport mechanism and how the catalytic activity occurs in the highly reductive and proteolytic cytosol, it is clear that the antibody cannot directly impact catalysis and/or substrate access to the catalytic site. Detailed epitope mapping has characterized this unique epitope to lie on the S1 and S4 subunit interface primarily on the S1 or A-subunit (165). This suggests a type of stapling mechanism whereby the A-subunit would be unable to separate from the B-subunit.

Because 1B7 is potently neutralizing, has a high potential for passive immunization or therapeutic use, and recognizes a unique epitope that is destroyed upon the toxoiding process in vaccine development (Sutherland & Maynard, in prep), Applicants sought to understand the molecular mechanism by which 1B7 protects against intoxication. Using immunofluorescence microscopy to track PTx intracellular transport in the absence and presence of the mAb 1B7, Applicants observed that 1B7 redirects PTx transport either through the prevention of toxin dissociation and thus the release of the S1 subunit into the cytosol or through blocking PTx signaling for retrograde trafficking trapping it in the early/recycling endosomes.

Experimental Procedures

Antigens and Antibodies

PTx (holotoxin) in glycerol was purchased from List Biological Laboratories, Inc. (Campbell, Calif.). The plasmids encoding a soluble, truncated version of the PTx S1 subunit, PTx-S1-220, and a recombinant, humanized single-chain antibody (scAb) version of the murine monoclonal antibody 1B7, expression and purification details have been described previously (165). Murine hybridoma cells producing the IgG2a antibody 1B7 or the IgG1 antibody 11E6 (152) were grown in T-flasks in Hybridoma-SFM serum-free media (Invitrogen) at 37° C. with 5% $CO_2$ until cell death (~1-2 months). After centrifugation at 3 krpm for 20 minutes, the supernatant was filter sterilized using a 0.45 μm filter and loaded directly onto a pre-equilibrated Protein-G column (GE Healthcare) with running buffer (20 mM sodium phosphate, pH 7.0). The mAb was eluted using low pH IgG elution buffer (Pierce, Rockford, Ill.) into collection tubes containing 1 M Tris pH 8.0 for neutralization. Protein concentrations were measured with micro-bicinchonoinic acid assay (Pierce, Rockford, Ill.), while SDS-PAGE stained with GelCode Blue (Pierce, Rockford, Ill.) verified protein preparation homogeneity and purity.

Quantitation antibody binding to live *B. pertussis* by flow cytometry. Specific IgG antibodies against *B. pertussis* were measured with the same preparation of live bacteria that was used in the OPA assay. The method was a slightly modified form of a similar procedure used to quantify IgG antibodies against group B meningococci (2). A twofold dilution, in HBSS/BSA, of a serum sample from an adult who had just recovered from confirmed pertussis was used to create the standard curve, and unknown serum samples were screened at a 1:40 dilution. Onto a U-shaped 96-well microtiter plate, 50 μl of diluted serum or standard serum was mixed with 10

μl of live *B. pertussis* (OD650 0.5). After incubation for 50 min at 37° C. with agitation, the bacteria were washed three times in HBSS/BSA by centrifugation at 1,100 g for 3 min. Finally, bound antibody was visualized after 1 h of incubation at 37° C. with a fluorescein iso-thiocyanate (FITC)-labeled goat anti-human IgG conjugate (Cappel, ICN Pharmaceuticals, Aurora, Ohio), followed by one washing. The samples were analyzed with the Partec CyFlow flow cytometer, and the pertussis-specific serum IgG concentration was calculated from the geometric mean fluorescence intensity with GraphPad Prism software, version 1.02 (GraphPad Software Inc., San Diego, Calif.). Pertussis-specific serum IgG concentrations are reported in arbitrary units (AU) with the standard serum IgG concentration designated as 1,000 AU/ml. The upper and lower limits of detection were 8,000 and 62.5 AU/ml, respectively; serum samples falling above or below these limits were set to 8,000 or 31.2 AU/ml.

Opsonophagocytic Activity

OPA was measured as a respiratory burst, as previously described for group B meningococci (2). Live *B. pertussis* cells were used as targets, and dihydrorhodamine 123 (DHR 123; Molecular Probes, Invitrogen)-primed PMNs from a donor heterozygous for the FcγRIIa allotype were used as effector cells. DHR 123 is a nonfluorescent probe that is converted to green-fluorescent rhodamine 123 within a phagocyte during a respiratory burst (28). Briefly, on 96-well microtiter plates, twofold dilution series of the various serum samples (50 ul) in Hanks' balanced salt solution supplemented with bovine serum albumin (2 mg/ml) (HBSS/BSA) were mixed with a 5-ul suspension of *B. pertussis* (OD at 650 nm [OD650] 0.53) and incubated for 50 min at 37° C. under agitation. As a negative control, the test serum was replaced with HBSS/BSA. Next, 5 μl human serum which had been passed through a protein G column (HiTrap protein G HP; GE Healthcare, Oslo, Norway) to remove IgG antibodies against *B. pertussis* was added as a complement source and the mixture was incubated further for 10 min. Finally, DHR 123-primed PMNs (50 ul) were added and incubation was continued for another 10 min. The PMNs were prepared from 21 ml heparinized venous blood from which the red cells had been removed by lysis in an ammonium chloride solution. The PMNs were washed three times with HBSS/BSA, resuspended in 11 ml HBSS/BSA, and primed with 11 ul DHR 123 (10 mg/ml). The responses were measured by flow cytometry with a Partec CyFlow flow cytometer (Partec GmbH, Münster, Germany), gating on the PMN population with a two-parameter forward scatter/side scatter dot plot. The analytical region for detecting respiratory-burst-positive cells was set on an FL1 histogram while running a negative control sample. The positive region was thus drawn to include less than 15% of the PMNs (exemplified in FIG. 1F, stippled line). The highest reciprocal serum dilution giving a 50% respiratory burst of the PMNs was recorded as the serum titer. A late-convalescent-phase serum sample from a subject with a confirmed case of pertussis that was collected 18 months after the onset of the disease was included on every microtiter plate.

The OPA were done as respiratory burst using the dihydrorhodamine 123 as a probe and human neutrophils as effector cells. Human serum (10%) passed through a ProteinG column (to remove IgG) was used as complement source. The bacteria (*B. pertussis* 105/06) is a clinical isolate grown on B-G agar. The antibodies were diluted two-fold starting 1:10 (supernatants) and 1:20 (purified). An anti-meningococcal monoclonal (151F9; anti-porA P1.16) was included as a negative control. The responses are read by flow cytometry, looking for fluorescence of the PMNs, and the percent positive PMNs are plotted on the Y-axis. As you can see from the curves both the two monoclonals have negligible activity compared to the P-IVIG and the KjHa-serum (a convalescent serum). I also measured the binding of the antibodies to live *B. pertussis*, as shown in the lower histogram panel. The mouse antibodies were stained with anti-mouse Ig-FITC and the human antibodies with anti-human IgG-FITC. (The 151F9 against meningococci is just a positive control to check the conjugate.) The binding results strongly indicate that the PT epitopes (or PT at all(?)) is not significantly expressed at the bacterial surface. I guess the P-IVIG has a broad specificity similar to the KjHa serum; these two also bound similar to a *B. parapertussis* (not shown).

Haptoglobin ELISA

Haptoglobin was used as a model soluble receptor to detect PTx binding using a method adapted from Antoine, 1990 (54). High binding ELISA plates (Costar) were coated with 50 μL/well of haptoglobin (ProSpec) at 2 μg/mL in 0.1 M $NaHCO_3$ buffer, pH 9.6. All plated volumes were 50 μL/well unless otherwise indicated. Plates were washed three times in wash buffer (phosphate buffered saline (PBS), pH 7.4+0.05% Tween-20) after each incubation. After overnight incubation at 4° C., the plates were blocked with 200 μL/well blocking buffer (PBS+0.05% Tween-20+4% BSA+4% FBS) at room temperature for 6 hours. Meanwhile, 5 μg/well of antibody (1B7, 11E6, or isotype control) was combined with PTx at 2 μg/mL in blocking buffer with no FBS and allowed to equilibrate at 37° C. for 1 hour. Pre-incubated antibody-toxin complex was then added to each well and incubated at 4° C. overnight. Anti-mouse-IgG-Biotin (MP Biomedicals) was added at a 1/500 dilution in wash buffer and incubated at 37° C. for 1½ hrs. Next, streptavidin-HRP (Pierce, Rockford, Ill.) was added at a 1/8000 dilution in blocking buffer and incubated at 37° C. for ½ hr. Signal was developed by adding 50 μL/well of developing buffer (0.1 M citrate buffer, pH 4.5; 0.4 mg/mL O-phenylenediamine dihydrochloride (Sigma-Aldrich) and 1 μL/mL hydrogen peroxide) for ~5 min. The reaction was quenched with 50 μL/well of 3 N HCl, and the plate read using a SoftMax Pro v5 (Molecular Devices) at 492 nm.

Effects of organelle-specific conditions on antibody/toxin interaction

As PTx undergoes retrograde transport in cells, it is exposed to different biochemical conditions in the different organelles. To determine whether 1B7 can maintain high affinity for PTx under these conditions, Applicants performed a series of ELISAs mimicking organelle environments. PTx-S1-220 was reduced by incubation with 20 mM DTT at 37° C. for 30 min. Subsequent di-sulfide bond reformation was prevented by the addition 100 mM iodoacetamide for 30 min at room temperature. High binding ELISA plates were coated with PTx-S1-220 or reduced PTx-S1-220 at 35 μg/mL and subsequently serially diluted 1: $\sqrt{10}$ in PBS. All plated volumes were 50 μL/well unless otherwise indicated After overnight incubation at 4° C., the plates were blocked with 200 μL/well blocking buffer (PBS+5% milk) at room temperature for 1 hour. After washing three times with PBS containing 0.05% Tween-20, 50 μL/well of hu1B7 was added at 5 μg/mL in buffer containing 5% milk and adjusted to the desired pH with HCl (50 mM Tris-HCl pH 7.2; 20 mM Bis-Tris pH 7.0, 6.5, and 6.0; 20 mM L-histidine pH 5.5 and 5.0). The plate was incubated at 4, 25, 37, 42 or 55° C. for 1 hour. After washing an additional three times, peroxidase conjugated anti-mouse IgG (Sigma-Aldrich, St. Louis, Mo.) was added at a 1:2500 dilution in blocking buffer, and the plates were incubated again at room temperature for 1 hour. After a final three washes, the plates were developed with tetramethylbenzidine dihydrochloride substrate (Pierce). The reaction was quenched with 1 N HCl and read using a SoftMax Pro v5

(Molecular Devices) at 405 nm. The same software was used to calculate IC50's using a 4 parameter logistic (4PL) model for each individual curve (146).

To evaluate the effect of specific molecules present in the ER on the antibody-toxin interaction (e.g., ATP, NAD and protein disulfide isomerase [PDI]), indirect ELISAs were performed as above with the following exceptions. Plates were coated with 2.0 µg/mL PTx in PBS, pH 7.4. After blocking, samples were added in two steps. In the first step, ATP at 0.5 mM or NAD at 7.5 µM was added to the wells in 1:2 serial dilutions while mAb 1B7 was added at a constant concentration of 0.5 µg/well in blocking buffer. Plates were incubated at 37° C. for 1 hr. The mAb 1B7 at 0.5 µg/well was added to the wells previously incubated with ATP or NAD and ATP at 0.5 mM or NAD at 7.5 µM was added in 1:2 serial dilutions to the wells previously incubated with mAb 1B7. The plates were once again incubated at 37° C. for 1 hr, prior to signal development.

Fluorescent labeling and anisotropy

PTx-S1-220 was buffer exchanged into 50 mM borate buffer, pH 8.5 at 2 mg/mL. Fluorescein iso-thio-cyanate (FITC, Pierce) was dissolved in 50 µL DMSO for a final concentration of 10 mg/mL and added at 20-fold molar excess to the buffer exchanged PTx-S1-220. After incubation in the dark with stirring at room temperature, the labeled protein was separated from free FITC by centrifugation in a PBS equilibrated Micro-Bio-Spin 30 (Bio-RAD). Fluorescent anisotropy measurements were collected at 0.2 µM in the same buffers used for pH/temperature studies (pH 5.5, 6.0, 6.5, and 7.2) using the Envision Microplate Reader (Perkin Elmer).

Immunofluorescence microscopy

Coverslips were seeded with Chinese Hamster Ovary (CHO) cells and allowed to grow to 50-70% confluency. To visualize PTx trafficking, cells were incubated with 10 nM PTx for varying amounts of time (from 20 minutes to 4 hours), at which point the cells were, fixed and stained to detect PTx and to localize organelles. To examine the effects of 1B7 on PTx trafficking, PTx was pre-incubated with 500-fold molar excess of 1B7 or mouse IgG2a isotype control (Santa Cruz Biotech), at 37° C. with 5% $CO_2$ for ½ hour prior to incubation with cells. The cells were then incubated in serum and antibiotic-free RPMI media containing 2 mg/mL BSA at 37° C. with 5% $CO_2$ for ½ hour. All samples were washed two times with Hanks Balanced Salt Solution (HBSS) prior to further processing.

After rinsing with PBS, the cells were fixed with 4% paraformaldehyde for 20 min at 37° C. Following three PBS washes, the cells were permeabilized with PBS containing 3% FBS and 0.1% Triton X-100 for 1 hr and subsequently blocked with PBS containing 3% FBS for 1 hr at 37° C. Primary antibody labeling using mAb 1B7 or human polyclonal P-IGIV (to detect PTx) or mouse IgG2a (to detect 1B7), at 0.1 µg/mL in the same buffer in humid conditions at 4° C. overnight. The next day, the cells were washed three times with PBS and labeled with secondary antibodies, anti-mouse-IgG-Cy5 (Molecular Probes) or anti-human-IgG-Dylight™ 405 (KPL, Gaithersburg, Md.), at 1:1000 dilutions in PBS with 3% FBS in the dark at 37° C. for 1 hr. After three final washes, the coverslips were mounted on slides using a drop of fluoromount-G (SouthernBiotech, Birmingham, Ala.). Imaging was performed with a Zeiss Axiovert fluorescent microscope (Carl Zeiss, Inc) and AxioVision software or Leica SP2 AOBS confocal microscope (Leica, Bannockburn, Ill.).

To visualize endosomes, 25 µg/mL transferrin-Cy3 (Molecular Probes) was added to cells with the PTx solution in RPMI with 2 mg/mL BSA at 37° C. for 5-240 min. To detect lysosomes, 200 µg/mL dextran-Cy3 (Molecular Probes) was added in the same manner. The endoplasmic reticulum was detected by primary labeling with a rabbit antibody binding the ER-resident protein, protein disulfide isomerase (PDI, SigmaAldrich) at 1:1000 dilution and detected with 1:1000 anti-rabbit-IgG-Cy3 (Molecular Probes). To fluorescently label the Golgi, the day before the experiment, Golgi-GFP Organelle Lights reagent (Molecular Probes) was added to cells. The transduction solution and cells were incubated in PBS for three hours at room temperature. Transduction solution was removed by aspiration and replaced with enhancer solution in DMEM for a 2 hr incubation at 37° C. with 5% $CO_2$. This solution was then replaced with fresh DMEM for overnight incubation.

Results

PTx can simultaneously bind 1B7 and a model receptor Many neutralizing antibodies act by sterically blocking key interactions or through Fc-mediated effector functions such as complement activation. In contrast, 1B7 binds an epitope located primarily on the S1 subunit, distal to the receptor binding site contained in subunits S2 and S3, and is unlikely to interfere directly with toxin-receptor interactions. Detailed analysis of the epitope bound by 1B7 indicates that it binds across the S1-S4 interface, in effect "stapling" the two subunits together (Sutherland ref). Additionally, many anti-toxin antibodies, including those against botulinum, shiga and anthrax toxins, do not require Fc functions to protect in vivo (REFS-JD Marks or Lang/Cryz; Tzipori, JAM). As Fc-free versions of 1B7, such as Fab and recombinant single-chains, are able to protect CHO cells during in vitro neutralization assays, effector functions do not seem crucial for 1B7 activity. Taken together, the interfacial epitope and lack of Fc involvement suggest that 1B7 neutralizes PTx by affecting cellular trafficking steps, perhaps by preventing S1 release from holotoxin in the endoplasmic reticulum (ER).

In order for 1B7 to directly influence PTx intracellular trafficking, the 1B7-PTx complex must be competent for binding terminally sialated glycoproteins as cellular receptors(59, 76, 180). Applicants first aimed to determine whether PTx is able to simultaneously bind 1B7 and a model cellular receptor, the glycoconjugate haptoglobin (156). An indirect ELISA was used to determine whether or not PTx pre-complexed with 1B7 is able to bind to immobilized haptoglobin. Compared to a control antibody, the PTx-1B7 complex is able to bind haptoglobin above control levels.

1B7 binds PTx under organelle conditions but not cytosolic conditions After binding to a cellular receptor, PTx is endocytosed and follows a path of retrograde transport, traveling through the early/recycling endosomes to the Golgi and then presumably to the ER. Here, the presence of a reducing potential and PDI cleave a disulfide bond in the S1 subunit, facilitating release from the PTx B subunit and transport out of the ER into the cytosol. In order for 1B7 to directly influence PTx in any of these compartments, the antibody would need to retain high affinity binding in the unique biochemical conditions corresponding to each sub-cellular compartment.

Indirect ELISAs to monitor the equilibrium 1B7-PTx interaction were performed under conditions mimicking those of each sub-cellular compartment. describe unique conditions of each compartment and how tested variable represent organelle conditions. Binding at increased temperatures was assessed, as ER-mediated unfolding is reported to be similar to thermal unfolding for PTx at various temperatures (25, 37, 42, and 55° C.) and at the pH conditions (pH 5-7.2) of the organelles. At 25 or 37 C, decreasing the pH from 7.2 to 5.0 had no significant effect on 1B7 binding to PTx. At higher temperatures, binding is reduced only at the lowest pH, 5.0 (see Table 1). Fluorescent anisotropy to measure the protein flexibility of FITC-labeled PTx-S1-220 indicates that the toxin becomes more rigid/compact with decreased pH. However, if PTx is reduced, 1B7 binding becomes much weaker at all pHs (xx-fold), indicating this complex will be unstable in the reducing environments of the cytosol and possibly the ER.

In the ER, ATP binds the central pore of the B-subunit, destabilizing the S1-B subunit interaction, possibly triggering S1 release and subsequent transport out of the ER (95). To determine whether 1B7 remains bound to oxidized PTx under ER conditions or can perhaps block PDI-mediated reduction of the S1 disulfide bond, Applicants performed another series of ELISAs. The complex is stable at 37° C. with 2 mM and up to 0.5 mM ATP indicating that 1B7 is able to remain in complex with PTx upon binding of ATP to the B-subunit. This is in agreement with studies done by Sato which showed that mAb 1B7 was able to neutralize the toxin's ATP-ribosylase activity in the presence of 4 nM ATP even after the complex was reduced with DTT (154).

1B7 alters PTx retrograde trafficking The typical protein trafficking pathway consists of newly translated proteins entering the ER in which ATP and various chaperones including PDI facilitate their folding in a neutral, pH 7.0, environment. Misfolded proteins are secreted from the ER into the cytosol for proteolytic degradation through the ERAD pathway which is known to be exploited by some AB type toxins including cholera for release into the cytosol (120). Once properly folded, the protein traffics to the Golgi where it is properly processed and packaged for its final destination also utilizing ATP at a slightly lower pH of 6.5. Early endosomes travel to or from the Golgi or the late endosomes/lysosomes while recycling endosomes recycle back to the outer membrane low pH of these organelles for unfolding and subsequent escape into the cytosol (75). The retrograde trafficking of AB type toxins is the opposite of the typical protein trafficking pathway with the toxin entering the early/recycling endosomes and subsequently trafficking through the Golgi to the ER and eventually the cytosol.

In order to determine the effects of 1B7 on PTx intracellular trafficking, four organelles were looked at in detail in immunofluorescent microscopy studies including the early/recycling endosomes, the Golgi, the ER, and the late endosomes. PTx was allowed to incubate with CHO cells for 15-240 min, the cells were fixed, and subsequently labeled using mAb 1B7 and anti-mouse-Cy5. 1B7 specificity for PTx was tested by labeling non-intoxicated cells with 1B7 and intoxicated cells with an isotype control mouse IgG2a antibody. Staining at the same concentrations, conditions, and settings with these controls resulted in no detectable fluorescence. The toxin bound to the cell surface receptors and underwent receptor mediated endocytosis into the early/recycling endosomes after ~30 min incubation as seen via co-incubation with transferrin-ALEXA. The toxin was then transported to and began accumulating in the Golgi with almost 100% localization around 2 hrs. The toxin did not enter the ER until xx hrs since the Golgi is the slow step in the retrograde trafficking pathway and subsequently the cytosol at xx hrs. The toxin did not appear to localize in the late endosomes at any time as seen via co-incubation with dextran-ALEXA.

Co-trafficking experiments of the 1B7/PTx complex were then undertaken using control antibodies of an IgG2a mouse isotype control and polyclonal mAb, P-IGIV, along with the same 15-240 min time scale, conditions, and labeling used in PTx trafficking. The complex undergoes the same receptor mediated endocytosis into the early/recycling endosomes after ~30 min incubation. (A) However, it remains in these early/recycling endosomes or traffics to the late endosomes/lysosomes after xx hr. (B) Accumulation in the Golgi is also observed with max localization around 2 hrs followed by transport to the ER at xx hrs. The complex, however, remains in the ER and is unable to enter the cytosol possibly due to the "stapling" action of mAb 1B7 on the two subunits. After xx hrs, the complex starts to localize in the late endosomes/lysosomes where it will be degraded. The ability of antibodies to protect against toxins by binding and co-internalizing with them in order to redirect intracellular trafficking has been shown previously with anti-Shiga Toxin 2 mAbs (116, 160) and also anti-botulism toxin mAbs (53).

1B7 is a unique antibody that potently neutralizes PTx activity by binding the toxin and co-internalizing with it into target mammalian cells. Once inside the cell, 1B7 confines PTx to the early/recycling endosomes and ultimately the lysosomes thus rerouting it from its typical retrograde pathway of early endosomes to Golgi to ER to cytosol. This ultimately prevents the intracellular toxic effects of PTx by circumventing the escape of the catalytic S1 subunit into the cytosol. The exact mechanism of this rerouting is yet to be determined, but may be closely linked to 1B7's unique epitope which spans the S1 and S4 subunit interface thereby "stapling" the subunits together.

Given 1B7's unique ability to co-internalize with and redirect PTx intracellular trafficking, the role of effector functions appears to be a secondary if not a mute point. Although originally isolated as a mouse IgG2a antibody (152), various constructs of 1B7 including Fabs, scFvs, and scAbs which all lack Fc regions are able to protect in in vitro CHO cell neutralization assays despite the lack of Fc receptors in CHO cells (165). Furthermore, several mAbs of various isotypes bind PTx with high affinity but are non-neutralizing further indicating that effector functions are not the primary protective mechanism (152). This may be due to the relatively fast internalization time of PTx, which enters cells within 30 min thus escaping into the cell before either activation of complement or uptake by phagocytes. Another possible explanation would be if PTx can undergo retrograde transport upon Fc receptor mediated endocytosis. This is less likely since there are protective anti-B-subunit antibodies such as 11E6 which block PTx from binding to cellular receptors. These resultant antibody/toxin complexes would ultimately undergo phagocytosis, thus making retrograde trafficking or intoxication of phagocytes unlikely. Thus, effector functions may be involved secondarily in other target cells such as macrophages, APCs, or neutrophils which do contain Fc receptors most likely in further recycling the antibody/toxin complexes out of the cells.

Since PTx is highly immunogenic, immunization with it results in the generation of several antibodies with various affinities and recognizing a plethora of epitopes on the toxin. Interestingly, only a small subset of these antibodies is neutralizing and of the many toxin epitopes, only four are protective. One of these major protective epitopes lies near or in the pore of the B subunit and effectively blocks receptor binding and thus internalization. Most antibodies recognizing the S1 subunit of the toxin are non-neutralizing. However, epitopes spanning the S1/B interface are highly neutralizing in that they staple the subunits together resulting in co-trafficking into target cells and redirection of intracellular trafficking by preventing dissociation. 1B7 and 7F2 are two such mAbs which both bridge the S1/S4 interface with 1B7 being predominantly S1 and 7F2 predominantly S4.

There are obscure but potently neutralizing epitopes which result in protection even at relatively modest serum concentrations (172). In the case of PTx, 1B7 recognizes one such epitope. Similar rare protective antibodies and a novel small molecule have been isolated and characterized for Shiga toxin 2 (116, 160) and Shiga-like toxins (158), respectively, which co-traffic into target cells and redirect intracellular trafficking. These also block retrograde trafficking of the toxin at the early endosome-Golgi interface resulting in a shift to recycling endosomes. This similarity indicates that co-trafficking and redirecting may be a common mechanism of protection against AB-type toxins. Further research either into engineering or isolating unique mAbs which span A/B subunit interfaces may be the future in developing passive immunization strategies for these various diseases.

Current acellular vaccines for pertussis utilize chemically detoxified PTx. This has been shown to destroy the protective epitope recognized by 1B7 (136) resulting in lower protective antibody titers upon vaccination than upon actual infection (Sutherland and Maynard, in prep). Other focuses in pertussis vaccine design include S1 subunit DNA and protein vaccines which also have lower protective activity most likely because they too lack this protective epitope (105, 106). Improvements in vaccine design can be made to elicit 1B7-like antibodies for this unique and difficult epitope similar to current HIV research (172). One possibility would be to use catalytically inactive genetically detoxified PTx (9K/129G) with some additional genetic modifications to the B-subunit in order to block cellular binding and side-effects such as histamine sensitization and leukocytosis while retaining protective epitopes. Another possibility could be to design a fusion protein of the S1/S4 complex which would elicit antibodies that would recognize the unique and protective interface between these two subunits.

1B7 recognizes a unique and potently neutralizing epitope on PTx resulting not only in its co-internalization into target cells but also redirecting of intracellular trafficking. This mAb neutralizes PTx function by preventing its dissociation and retrograde trafficking resulting in its accumulation and segregation to the early and recycling endosomes. Thus 1B7 and the unique epitope it recognizes are strong potential candidates for not only passive immunization strategies but also further vaccine improvements.

VIII. Tables

TABLE 1

Binding between PTx, its subunits, and naturally occurring variants to 1B7

| PTx | Mutations wt Tohama I (PTx-S1B) | ELISA* % EC$_{50\,PTx}$ | m1B7 mAb~1000 RU $k_d \times 10^{-3}$ (sec$^{-1}$) |
|---|---|---|---|
| PTx | — | 100 | 0.4 +/− 0.6 |
| B-oligomer | — | 8 | 2.7 +/− 0.6 |
| PTx-S1 235 | — | 20** | 1.9 +/− 0.3 |
| PTx-S1 220 | — | 90 +/− 10*** | 1.4 +/− 0.1 |
| PTx-S1A | M194I | 50 +/− 40 | 0.71 +/− 0.04 |
| PTx-S1D | D34E, I198V | 90 +/− 50 | 0.95 +/− 0.05 |
| PTx-S1E | D34E, S162P, I198M | 80 +/− 30 | 1.8 +/− 0.5 |
| PTx-S1 9K/129G | R9K, E129G | 60 +/− 30 | 1.6 +/− 0.7 |

*All ELISAs were run using hu1B7 as the primary antibody.
**S1 235 maintained in soluble form in 0.03% CHAPS, 0.1 mM Na$_2$EDTA, and 10 mM Tris
***Due to low expression, only the purest samples were used for these numbers

TABLE 2

Binding and neutralizing activity of 1B7 variants

| Antibody | Heat Studies % EC$_{50\,4°\,C}$ | | CHO cell Neutralization |
|---|---|---|---|
| | 37° C./24 hr | 50° C./2 hr | Assay (µg) |
| mAb 1B7 | 100 | 20 | 0.09 |
| M1B7 | 100 | 40 | 3 |
| Hu1B7 | 70 | 10 | 9 |

TABLE 3

In silico and experimental characterization of hu1B7 and variants

| Antibody | CDR | Alanine Scan Highest ΔΔG$_{(complex)}$ (kcal/mol) | ΔG$_{(partner)}$ (kcal/mol) | *CD spec % α | % β | ELISA % EC$_{50\,hu1B7}$ | Heat Studies EC$_{50}$ 4° C. 37° C. 24 hr | 50° C. 2 hr | CHO Cell Neutralization Assay µg |
|---|---|---|---|---|---|---|---|---|---|
| Binding | | | | | | | | | |
| hu1B7 | — | — | — | 34 | 38 | 100 | 70 | 10 | 9 |
| S30A | L1 | 2.9 | 0.6 | 33 | 49 | 100 +/− 0 | 100 | 2 | 9 |
| N53A | L2 | 1.2 | 0.4 | 23 | 37 | 390 +/− 30 | 70 | 30 | 9 |
| S92A | L3 | 1.2 | 0.3 | 31 | 68 | 50 +/− 10 | 100 | 5 | 9 |
| S93A | L3 | 2.8 | 1.5 | 34 | 28 | 80 +/− 60 | 100 | 20 | 9 |
| S31A | H1 | 0.2 | −0.2 | 25 | 19 | 70 +/− 20 | 100 | 5 | 9 |
| F52A | H2 | 2 | 2.9 | 31 | 44 | 120 +/− 50 | 70 | 9 | 9 |
| Reduced Binding | | | | | | | | | |
| F31A | L1 | 1.8 | 2.4 | 28 | 28 | 2 +/− 3 | 60 | <1% | NP |
| H94A | L3 | 3.1 | 0.8 | 27 | 45 | 3 +/− 4 | 90 | <1% | NP |
| S97A | H3 | 2.5 | −0.2 | 29 | 19 | 5 +/− 4 | 100 | 30 | NP |
| Non-Binding | | | | | | | | | |
| W91A | L3 | 2 | 3.6 | 27 | 44 | <1% | — | — | NP |
| W33A | H1 | 2 | 3.5 | 54 | 32 | <1% | 80 | <1% | NP |
| N58A | H2 | 4.2 | 0.5 | 32 | 23 | <1% | 90 | <1% | NP |

These secondary structure values are typical for scFv-huCκ.
NP, no protection

TABLE 4

In silico and experimental characterization of PTx-S1-220 and variants

| PTx | Alanine Scan Average ΔΔG$_{(complex)}$ (kcal/mol) | ΔG$_{(partner)}$ (kcal/mol) | CD spec % α | % β | ELISA % EC$_{50\ PTX}$ | m1B7 mAb ~1000 RU k$_d$ × 10$^{-3}$ sec$^{-1}$ |
|---|---|---|---|---|---|---|
| Binding | | | | | | |
| PTx-S1-220 | — | — | 11 | 40 | 90 +/− 10 | 1.4 +/− 0.1 |
| R146A | 10.9 | 3.8 | 12 | 42 | 60 +/− 40 | 1.5 +/− 0.1 |
| E155A | 0.4 | 0.6 | 8 | 44.1 | 50 +/− 40 | 1.1 +/− 0.1 |
| T156A | 0.5 | 2.5 | 12 | 41.6 | 70 +/− 30 | 1.1 +/− 0.1 |
| T159A | 3.7 | 2.1 | 6 | 49.8 | 90 +/− 30 | 1.4 +/− 0.2 |
| Y161A | 6.5 | 2.3 | 11 | 41.1 | 50 +/− 20 | 1.3 +/− 0.6 |
| N176 | 0.6 | −0.4 | 13 | 54 | 50 +/− 20 | 1.1 +/− 0.1 |
| E210A | 2.2 | 0.4 | 17 | 33.7 | 70 +/− 40 | 1.6 +/− 0.2* |
| E16A | 2.9 | −0.3 | 9 | 44 | 20 +/− 10 | 1.6 +/− 0.1 |
| T81A | 2.8 | 1.1 | 9 | 58 | 30 +/− 10 | 1.7 +/− 0.9 |
| T158A | 1.5 | 1.2 | 10 | 42.8 | 30 +/− 20 | 1.3 +/− 0.2 |
| Y166A | 4.9 | 6.8 | 29 | 27.2 | 30 +/− 10 | 1.4 +/− 0.2 |
| Reduced Binding | | | | | | |
| R39A | 1.1 | −0.3 | 15 | 43 | 30 +/− 10 | 3.0 +/− 0.4 |
| T153A | 1.2 | 1.0 | 14 | 39.2 | 11 +/− 5 | 2.0 +/− 0.4 |
| Non-Binding | | | | | | |
| R79A | 0.8 | 0.1 | 9 | 61 | 1 +/− 1 | 25 +/− 4 |
| H83A | 3.3 | 1.4 | 12 | 41 | <1% | 10 +/− 2 |
| Y148A | 6.6 | 4.7 | 9 | 42 | <1% | 29 +/− 6 |
| N150A | 2.1 | 2.2 | 6 | 46 | <1% | 8 +/− 1 |

TABLE 5

Binding analysis of PTx-S1-220 variants

| PTx | ELISA % EC$_{50\ PTx}$ | Western Blot mAb 1B7 |
|---|---|---|
| PTx-S1-220 | 90 +/− 10 | +++ |
| 9K/129G | 60 +/− 30 | +++ |
| Y8A | <1% | − |
| R9A | 9 | +++ |
| Y10A | 5 | + |
| D11A | 7 | + |
| S12A | 20 | ++ |
| R13A | 8 | +/− |
| E16A | 20 +/− 10 | ++ |
| R79A | 1 +/− 1 | +/− |
| T81A | 30 +/− 10 | +++ |
| H83A | <1% | + |
| Y148A | <1% | − |
| N150A | <1% | +/− |
| T153A | 11 +/− 5 | ++ |

TABLE 6

Virulence Factors Associated with *Bordetella pertussis* pathogenesis (Kerr and Matthews, 2000)

| Virulence Factor | MolWt (kDa) | Mechanism | Stage of Disease | Protective Immunity | Location, other features |
|---|---|---|---|---|---|
| Agglutinin 2/ fimbria 2 | 22 | Fim2 binds heparin; FimD binds heparin and integrin VLA-5 | A | + | Located on fimbriae (major subunit); Abs to agg2 confer protective immunity against serotype 1, 2 |
| Agglutinin 3 | | | A | + | Either a somatic or fimbrial antigen; agg3 confers protective immunity against serotype 1, 3 |
| Fimbria 3 | 21.5 | FimD binds heparin and integrin VLA-5 | A | + | Major fimbrial subunit |
| P.69 Pertactin | 69 | RGD motif probably binds CR3 | A | + | Somatic antigen |
| Pertussis toxin (PT) | 105 (sub-units of 26, 22, 22, 12, | PT binds ciliated epithelium and macrophages; mimic selectins and upregulates macrophage CR3 for | ADLS | + | Synergistic adhesin with FHA |

TABLE 6-continued

Virulence Factors Associated with *Bordetella pertussis* pathogenesis (Kerr and Matthews, 2000)

| Virulence Factor | MolWt (kDa) | Mechanism | Stage of Disease | Protective Immunity | Location, other features |
|---|---|---|---|---|---|
| | 12, 11) | FHA binding; ADP ribosylation of cellular G i/o proteins | | | |
| Filamentous hemagglutinin (FHA) | 220 | FHA binds both the bacterium and macrophage CR3 to facilitate phagocytosis | A | | Secreted: synergistic adhesin with PT |
| Adenylate cyclase/ haemolysin | 45 | ATP hydrolysis with raised intracellular cAMP in macrophages and lymphocytes; induces apoptosis | DLS | | Secreted by type I pathway; requires CyaB, D, E proteins; activated by eukaryotic calmodulin |
| Tracheal cytotoxin | 921 | DNA inhibition in ciliated epithelium | DL | | A muramyl peptide; derived from bacterial peptidoglycan |
| Dermonecrotic toxin | 102 (subunits of 30, 24) | Inhibition of Na+—K+ ATPase; vasoconstriction | LS | | localized to the bacterial cytoplasm; part of the molecule probably exposed at cell surface |
| Lipopolysaccharide | | Endotoxin-like effects; pyrogenic, sensitization to histamine | LS | | Two lipids, A and X; two different oligosaccharides, I and II |
| Tracheal colonization factor | 64 | Tcf binding probably mediated by RGD motif | A | | Secreted by type IV pathway |
| Serum resistance factor | BrkA, 103; BrkB 32 | | D | | Secreted by type IV pathway; *Bodetella* resistance to killing |
| Type III secretion | | Contact-dependent secretion | DL | | Exported molecules unknown |

A, attachment; D, evasion of host defense; L, local effects; S, systemic effects

TABLE 7

Primers for Total Gene Synthesis of Humanized 1B7 scFv (sequences in order of appearance: SEQ ID NOS: 14-54).

| Primer Name | Primer Sequence, 5' to 3' |
|---|---|
| 5' scFv V_L SfiI | TTACTCGCGGCCCAGCCGGCCATGGCGGACTACAAAG |
| 5' hu1B7 1-40 | ATGGCGGACTACAAAGACATCCAGATGACCCAGTCCCCGT |
| 5' hu1B7 41-80 | CCTCCCTGTCCGCTTCCGTTGGTGACCGCGTTACCATCAC |
| 5' hu1B7 81-120 | CTGCTCCGCTTCCTCCTCCGTTTCCTTCATGTACTGGTAC |
| 5' hu1B7 121-160 | CAGCAGAAACCGGGTAAAGCTCCGAAACTGCTGATCTACC |
| 5' hu1B7 161-200 | TGACCTCCAACCTGCCGTCCGGTGTTCCGTCCCGCTTCTC |
| 5' hu1B7 201-240 | CGGTTCCGGTTCCGGTACCGACTACACCCTGACCATCTCC |
| 5' hu1B7 241-280 | TCCCTGCAGCCGGAAGACTTCGCTACCTACTACTGCCAGC |
| 5' hu1B7 281-320 | AGTGGTCCTCCCACCCGCCGACCTTCGGTCAGGGTACCAA |
| 5' hu1B7 321-360 | AGTTGAAATCAAACGCACCGGTGGTGGTGGTTCTGGTGGT |
| 5' hu1B7 361-400 | GGTGGTTCTGGCGGCGGCGGCTCCGGTGGTGGTGGATCCG |
| 5' hu1B7 401-440 | AAGTTCAGCTGGTTGAATC |
| 5' hu1B7 441-480 | CGGTGGTGGTCTGGTTCAGCCGGGTGGTTCCCTGCGCCTG |
| 5' hu1B7 481-520 | TCCTGCGCTGCTTCCGGTTACAAATTCACCTCCTACTGGA |
| 5' hu1B7 521-560 | TGCACTGGGTTCGCCAGGCTCCGGGTAAAGGTCTGGAATG |
| 5' hu1B7 561-600 | GGTTGGTAACATCTTCCCGGGTTCCGGTTCCACCAACTAC |
| 5' hu1B7 601-640 | GACGAATTCAAAAACTCCCGCTTCACCATCTCCGTTGACA |
| 5' hu1B7 641-680 | CCTCCAAAAACACCGCTTACCTGCAGATGAACTCCCTGCG |

TABLE 7-continued

Primers for Total Gene Synthesis of Humanized 1B7 scFv (sequences in order of appearance: SEQ ID NOS: 14-54).

| Primer Name | Primer Sequence, 5' to 3' |
|---|---|
| 5' hu1B7 681-720 | CGCTGAAGACACCGCTGTTTACTACTGCACCCG CTGGCTG |
| 5' hu1B7 721-760 | TCCGGTGCTTACTTCGACTACTGGGGTCAGGGT ACCCTGG |
| 5' hu1B7 761-789 | TTACCGTTTCCTCGGCCTCGGGGCCGAA |
| 3' hu1B7 21-60 | AACGGAAGCGGACAGGGAGGACGGGACTGGGT CATCTGG |
| 3' hu1B7 61-100 | CGGAGGAGGAAGCGGAGCAGGTGATGGTAACGC GGTCACC |
| 3' hu1B7 101-140 | GCTTTACCCGGTTTCTGCTGGTACCAGTACATG AAGGAAA |
| 3' hu1B7 141-180 | GGACGGCAGGTTGGAGGTCAGGTAGATCAGCAG TTTCGGA |
| 3' hu1B7 181-220 | CGGTACCGGAACCGGAACCGGAGAAGCGGGACG GAACACC |
| 3' hu1B7 221-260 | AAGTCTTCCGGCTGCAGGGAGGAGATGGTCAGG GTGTAGT |
| 3' hu1B7 261-300 | CGGCGGGTGGGAGGACCACTGCTGGCAGTAGTA GGTAGCG |
| 3' hu1B7 301-340 | CGGTGCGTTTGATTTCAACTTTGGTACCCTGAC CGAAGGT |
| 3' hu1B7 341-380 | CCGCCGCCGCCAGAACCACCACCACCAGAACCA CCACCAC |
| 3' hu1B7 381-420 | GGATTCAACCAGCTGAACTTCGGATCCACCACC ACCGGAG |
| 3' hu1B7 421-460 | GCTGAACCAGACCACCACCGGATTCAACCAGCT GAACTTC |
| 3' hu1B7 461-500 | TAACCGGAAGCAGCGCAGGACAGGCGCAGGGAA CCACCCG |
| 3' hu1B7 501-540 | AGCCTGGCGAACCCAGTGCATCCAGTAGGAGGT GAATTTG |
| 3' hu1B7 541-580 | CCGGGAAGATGTTACCAACCCATTCCAGACCTT TACCCGG |
| 3' hu1B7 581-620 | CGGGAGTTGAATTTTCGTCGTAGTTGGTGGAA CCGGAAC |
| 3' hu1B7 621-660 | GTAAGCGGTGTTTTGGAGGTGTCAACGGAGAT GGTGAAG |
| 3' hu1B7 661-700 | AAACAGCGGTGTCTTCAGCGCGCAGGGAGTTCA TCTGCAG |
| 3' hu1B7 701-740 | TAGTCGAAGTAAGCACCGGACAGCCAGCGGGTG CAGTAGT |
| 3' hu1B7 741-780 | CGAGGCCGAGGAAACGGTAACCAGGGTACCCTG ACCCCAG |
| 3' scFv $V_H$ SfiI | CCTCGGCCTCGGGGCCGAATTCC |

TABLE 8

Characterization of Anti-Pertussis Toxin Antibodies Antibody

| Antibody | Purified Yield (mg/L)[1,2] | Affinity, $K_d$ (nM) | 50° C. Stability (2 hrs) | 37° C. Stability (24 hrs) | In Vitro Neutral-ization (nM) |
|---|---|---|---|---|---|
| 1B7 mAb | — | 1.1 ± 0.2 | 100% | ND[3] | 5.2 |
| 1B7 F(ab)$_2$ | — | ND | ND | ND | 15 |
| 1B7 Fab | — | 2.0 ± 0.8 | 100% | ND | 42 |
| 1B7 scFv | 0.01 | ND | ND | ND | ND |
| 1B7 scAb | 2.7 | 2.4 ± 0.8 | 3.5% | 31% | 377 |
| 1B7 scFv Cys23 | 0.20 | ND | 0% | ND | ND |
| 1B7 scAb Cys23 | 6.8 | 7.6 ± 0.4 | 0% | 96% | 720 |
| hu1B7 scFv | ND | >500 | ND | ND | ND |
| 1B7 3A scAb | 2.8 | 1.0 ± 0.2 | ND | 0.5% | 1500 |
| 11E6 mAb | — | 20 ± 5 | 100% | ND | 5.2 |
| 11E6 Fab | — | 9.3 ± 2 | 100% | ND | 42 |
| 11E6 scFv | <0.01 | ND | ND | ND | ND |
| 11E6 scAb | 4.0 | 19 ± 4.5 | 0% | 24% | 377 |

TABLE 9

Anti-PT scAbs Activity after Incubation at 37° C.

| scAb | 0 hrs | 3 hrs | 5 hrs | 11 hrs | 24 hrs | 48 hrs |
|---|---|---|---|---|---|---|
| 1B7 | 100% | 100% | 100% | 100% | 31% | 1.2% |
| 1B7-Cys23 | 100% | 100% | 100% | 94% | 96% | 7.8% |
| 1B7 3A | 100% | 22% | 18% | 3.4% | 0.5% | 0.2% |
| 11E6 | 100% | 70% | 77% | 43% | 24% | 4% |

Activity measured by direct PT ELISA after incubation at 37° C. for the indicated time. Percent remaining activity calculated from the antibody concentration resulting in 50% of the maximum ELISA signal, i.e., % activity=(Conc 50%, 4° C.*100%/Conc 50%, 37° C.).

TABLE 10

Effects of changes in pH and temperature on the IC$_{50}$ of the hu1B7/PTx-S1-220 complex measured using indirect ELISAs.

| | 25° C. | 37° C. | 42° C. | 55° C. |
|---|---|---|---|---|
| pH 7.2 | 3 | 4 | 3 | 100 |
| pH 7.0 | 2 | 6 | 3 | 4 |
| pH 6.5 | 2 | 4 | 3 | 10 |
| pH 6.0 | 2 | 4 | 2 | 5 |
| pH 5.5 | 2 | 4 | 4 | 4 |
| pH 5.0 | 2 | 4 | 400 | 40 |

IX. References

1. Kerr, J. R. 2000. Pathogenesis of human parvovirus B19 in rheumatic disease. *Ann Rheum Dis.* 59: 672-683.
2. Roush, S. W. and T. V. Murphy. 2007. Historical comparisons of morbidity and mortality for vaccine-preventable diseases in the United States. *JAMA.* 298: 2155-2163.
3. Jadhav, S. S. and S. Gairola. 1999. Composition of acellular pertussis and combination vaccines: a general review. *Biologicals.* 27: 105-110.
4. Kamachi, K., T. Konda, and Y. Arakawa. 2003. DNA vaccine encoding pertussis toxin S1 subunit induces protection against *Bordetella pertussis* in mice. *Vaccine.* 21: 4609-4615.
5. Pichichero, M. E., et al. 2006. Acellular pertussis vaccine booster combined with diphtheria and tetanus toxoids for adolescents. *Pediatrics.* 117: 1084-1093.
6. Taranger, J., et al. 2000. Correlation between pertussis toxin IgG antibodies in postvaccination sera and subsequent protection against pertussis. *J Infect Dis.* 181: 1010-1013.

7. Hellwig, S. M., et al. 2003. Crucial role of antibodies to pertactin in *Bordetella pertussis* immunity. *J Infect Dis.* 188: 738-742.
8. Sato, H. and Y. Sato. 1990. Protective activities in mice of monoclonal antibodies against pertussis toxin. *Infect Immun.* 58: 3369-3374.
9. Bruss, J. B. and G. R. Siber. 1999. Protective effects of pertussis immunoglobulin (P-IGIV) in the aerosol challenge model. *Clin Diagn Lab Immunol.* 6: 464-470.
10. Bruss, J. B. and G. R. Siber. 2002. Quantitative priming with inactivated pertussis toxoid vaccine in the aerosol challenge model. *Infect Immun.* 70: 4600-4608.
11. Cherry, J. D., et al. 1998. A search for serologic correlates of immunity to *Bordetella pertussis* cough illnesses. *Vaccine.* 16: 1901-1906.
12. Halperin, S. A., et al. 2007. Is pertussis immune globulin efficacious for the treatment of hospitalized infants with pertussis? No answer yet. *Pediatr Infect Dis J.* 26: 79-81.
13. Weingart, C. L., et al. 2000. Characterization of bactericidal immune responses following vaccination with acellular pertussis vaccines in adults. *Infect Immun.* 68: 7175-7179.
14. Mills, K. H. 2001. Immunity to *Bordetella pertussis*. *Microbes Infect.* 3: 655-677.
15. Sato, H., Y. Sato, and I. Ohishi. 1991. Comparison of pertussis toxin (PT)-neutralizing activities and mouse-protective activities of anti-PT mouse monoclonal antibodies. *Infect Immun.* 59: 3832-3835.
16. Kim, K. J., et al. 1989. Epitopes on the S1 subunit of pertussis toxin recognized by monoclonal antibodies. *Infect Immun.* 57: 944-950.
17. Kenimer, J. G., et al. 1989. Monoclonal antibodies to pertussis toxin: utilization as probes of toxin function. *Hybridoma.* 8: 37-51.
18. Bartoloni, A., et al. 1988. Mapping of a protective epitope of pertussis toxin by in vitro refolding of recombinant fragments. *Nat Biotechnol.* 6: 709-712.
19. Cieplak, W., et al. 1988. Identification of a region in the S1 subunit of pertussis toxin that is required for enzymatic activity and that contributes to the formation of a neutralizing antigenic determinant. *Proc Natl Acad Sci USA.* 85: 4667-4671.
20. Raupach, B. and M. A. Schmidt. 1994. Elucidation of linear epitopes of pertussis toxin using overlapping synthetic decapeptides: identification of a human B-cell determinant in the S1 subunit indicative of acute infections. *Microb Pathog.* 17: 213-226.
21. Burnette, W. N., et al. 1988. Pertussis toxin S1 mutant with reduced enzyme activity and a conserved protective epitope. *Science.* 242: 72-74.
22. Kaslow, H. R., et al. 1992. Detection of antibodies inhibiting the ADP-ribosyltransferase activity of pertussis toxin in human serum. *J Clin Microbiol.* 30: 1380-1387.
23. Stein, P. E., et al. 1994. The crystal structure of pertussis toxin. *Structure.* 2: 45-57.
24. Krueger, K. M. and J. T. Barbieri. 1994. Assignment of functional domains involved in ADP-ribosylation and B-oligomer binding within the carboxyl terminus of the S1 subunit of pertussis toxin. *Infect Immun.* 62: 2071-2078.
25. Krebber, A., et al. 1997. Reliable cloning of functional antibody variable domains from hybridomas and spleen cell repertoires employing a reengineered phage display system. *J Immunol Methods.* 201: 35-55.
26. Hayhurst, A., et al. 2003. Isolation and expression of recombinant antibody fragments to the biological warfare pathogen *Brucella melitensis*. *J Immunol Methods.* 276: 185-196.
27. Hemsley, A., et al. 1989. A simple method for site-directed mutagenesis using the polymerase chain reaction. *Nucleic Acids Res.* 17: 6545-6551.
28. Hayhurst, A. and W. J. Harris. 1999. *Escherichia coli* skp chaperone coexpression improves solubility and phage display of single-chain antibody fragments. *Protein Expr Purif.* 15: 336-343.
29. Hewlett, E. L., et al. 1983. Induction of a novel morphological response in Chinese hamster ovary cells by pertussis toxin. *Infect Immun.* 40: 1198-1203.
30. Whitelegg, N. R. and A. R. Rees. 2000. WAM: an improved algorithm for modelling antibodies on the WEB. *Protein Eng.* 13: 819-824.
31. Sood, V. D. and D. Baker. 2006. Recapitulation and design of protein binding peptide structures and sequences. *J Mol Biol.* 357: 917-927.
32. Chen, R. and Z. Weng. 2002. Docking unbound proteins using shape complementarity, desolvation, and electrostatics. *Proteins.* 47: 281-294.
33. Lyskov, S, and J. J. Gray. 2008. The RosettaDock server for local protein-protein docking *Nucleic Acids Res.* 36: W233-238.
34. Kortemme, T. and D. Baker. 2002. A simple physical model for binding energy hot spots in protein-protein complexes. *Proc Natl Acad Sci USA.* 99: 14116-14121.
35. Kortemme, T., D. E. Kim, and D. Baker. 2004. Computational alanine scanning of protein-protein interfaces. *Sci STKE.* 2004: pl 2.
36. Mayrose, I., et al. 2007. Epitope mapping using combinatorial phage-display libraries: a graph-based algorithm. *Nucleic Acids Res.* 35: 69-78.
37. Felici, F., et al. 1993. Mimicking of discontinuous epitopes by phage-displayed peptides, II. Selection of clones recognized by a protective monoclonal antibody against the *Bordetella pertussis* toxin from phage peptide libraries. *Gene.* 128: 21-27.
38. Pizza, M., et al. 1989. Mutants of pertussis toxin suitable for vaccine development. *Science.* 246: 497-500.
39. Hausman, S. Z. and D. L. Burns. 2000. Use of pertussis toxin encoded by ptx genes from *Bordetella bronchiseptica* to model the effects of antigenic drift of pertussis toxin on antibody neutralization. *Infect Immun.* 68: 3763-3767.
40. Braden, B. C., et al. 1995. Structure and thermodynamics of antigen recognition by antibodies. *Ann N Y Acad. Sci.* 764: 315-327.
41. Davies, D. R. and G. H. Cohen. 1996. Interactions of protein antigens with antibodies. *Proc Natl Acad Sci USA.* 93: 7-12.
42. Viswanathan, M., et al. 1996. Modeling the structure of the combining site of an antisweet taste ligand monoclonal antibody NC 10.14. *Biopolymers.* 39: 395-406.
43. Yang, J., et al. 2003. Dissecting cooperative and additive binding energetics in the affinity maturation pathway of a protein-protein interface. *J Biol Chem.* 278: 50412-50421.
44. Weiss, A. A., et al. 1983. Tn5-induced mutations affecting virulence factors of *Bordetella pertussis*. *Infect Immun.* 42: 33-41.
45. Storsaeter, J., et al. 1998. Levels of anti-pertussis antibodies related to protection after household exposure to *Bordetella pertussis*. *Vaccine.* 16: 1907-1916.
46. Mooi, F. R., I. H. van Loo, and A. J. King. 2001. Adaptation of *Bordetella pertussis* to vaccination: a cause for its reemergence? *Emerg Infect Dis.* 7: 526-528.
47. Makinen, J., et al. 2002. Rapid typing of *Bordetella pertussis* pertussis toxin gene variants by LightCycler real- 48. Sato, H., et al. 1987. Effect of monoclonal antibody to pertussis toxin on toxin activity. *Infect Immun.* 55: 909-915.
49. Maynard, J. A., et al. 2002. Protection against anthrax toxin by recombinant antibody fragments correlates with antigen affinity. *Nat Biotechnol.* 20: 597-601.
50. Hazes, B., et al. 1996. Crystal structure of the pertussis toxin-ATP complex: a molecular sensor. *J Mol Biol.* 258: 661-671.
51. Outbreaks of respiratory illness mistakenly attributed to pertussis—New Hampshire, Massachusetts, and Tennessee, 2004-2006. *MMWR Morb Mortal Wkly Rep,* 2007. Vol: p. 837-842.
52. Senzilet, L. D., et al., Pertussis is a frequent cause of prolonged cough illness in adults and adolescents. *Clin Infect Dis,* 2001. Vol: p. 1691-1697.
53. Pichichero, M. E., et al., Acellular pertussis vaccine booster combined with diphtheria and tetanus toxoids for adolescents. *Pediatrics,* 2006. Vol: p. 1084-1093.
54. Tanaka, M., et al., Trends in pertussis among infants in the United States, 1980-1999. *JAMA,* 2003. Vol: p. 2968-2975.
55. O'Brien, J. A. and J. J. Caro, Hospitalization for pertussis: profiles and case costs by age. *BMC Infect Dis,* 2005. Vol: p. 57.
56. Granstrom, M. and G. Granstrom, Serological correlates in whooping cough. *Vaccine,* 1993. Vol: p. 445-448.
57. Hazes, B. and R. J. Read, Accumulating evidence suggests that several AB-toxins subvert the endoplasmic reticulum-associated protein degradation pathway to enter target cells. *Biochemistry,* 1997. Vol: p. 11051-11054.
58. Lencer, W. I., Retrograde transport of cholera toxin into the ER of host cells. *Int J Med Microbiol,* 2004. Vol: p. 491-494.
59. Stechmann, B., et al., Inhibition of retrograde transport protects mice from lethal ricin challenge. *Cell,* Vol: p. 231-242.
60. Hazes, B., et al., Crystal structure of the pertussis toxin-ATP complex: a molecular sensor. *J Mol Biol,* 1996. Vol: p. 661-671.
61. Bruss, J. B. and G. R. Siber, Protective effects of pertussis immunoglobulin (P-IGIV) in the aerosol challenge model. *Clin Diagn Lab Immunol,* 1999. Vol: p. 464-470.
62. Bruss, J. B., et al., Treatment of severe pertussis: a study of the safety and pharmacology of intravenous pertussis immunoglobulin. *Pediatr Infect Dis J,* 1999. Vol: p. 505-511.
63. Granstrom, M., et al., Specific immunoglobulin for treatment of whooping cough. Lancet, 1991. Vol: p. 1230-1233.
64. Sato, H., et al., Monoclonal antibody against pertussis toxin: effect on toxin activity and pertussis infections. *Infect Immun,* 1984. Vol: p. 422-428.
65. Kaslow, H. R., et al., Detection of antibodies inhibiting the ADP-ribosyltransferase activity of pertussis toxin in human serum. *J Clin Microbiol,* 1992. Vol: p. 1380-1387.
66. Cieplak, W., et al., Identification of a region in the S1 subunit of pertussis toxin that is required for enzymatic activity and that contributes to the formation of a neutralizing antigenic determinant. *Proc Natl Acad Sci USA,* 1988. Vol: p. 4667-4671.
67. Burnette, W. N., et al., Pertussis toxin S1 mutant with reduced enzyme activity and a conserved protective epitope. Science, 1988. Vol: p. 72-74.
68. Sutherland, J. N. and J. A. Maynard, Characterization of a key neutralizing epitope on pertussis toxin recognized by monoclonal antibody 1B7. *Biochemistry,* 2009. Vol: p. 11982-11993.
69. Sato, H. and Y. Sato, Protective activities in mice of monoclonal antibodies against pertussis toxin. *Infect Immun,* 1990. Vol: p. 3369-3374.
70. Antoine, R. and C. Locht, Roles of the disulfide bond and the carboxy-terminal region of the S1 subunit in the assembly and biosynthesis of pertussis toxin. *Infect Immun,* 1990. Vol: p. 1518-1526.
71. Rieber, N., et al., Differences of humoral and cellular immune response to an acellular pertussis booster in adolescents with a whole cell or acellular primary vaccination. *Vaccine,* 2008. Vol: p. 6929-6935.
72. el Baya, A., et al., Pertussis toxin. Entry into cells and enzymatic activity. *Adv Exp Med Biol,* 1997. Vol: p. 83-86.
73. Witvliet, M. H., et al., Binding of pertussis toxin to eucaryotic cells and glycoproteins. *Infect Immun,* 1989. Vol: p. 3324-3330.
74. Brennan, M. J., et al., Lectin-like binding of pertussis toxin to a 165-kilodalton Chinese hamster ovary cell glycoprotein. *J Biol Chem,* 1988. Vol: p. 4895-4899.
75. Sato, Y., et al., Separation and purification of the hemagglutinins from *Bordetella pertussis. Infect Immun,* 1983. Vol: p. 313-320.
76. Sato, H., et al., Effect of monoclonal antibody to pertussis toxin on toxin activity. *Infect Immun,* 1987. Vol: p. 909-915.
77. Draper, R. K. and M. I. Simon, The entry of diphtheria toxin into the mammalian cell cytoplasm: evidence for lysosomal involvement. *J Cell Biol,* 1980. Vol: p. 849-854.
78. Smith, M. J., et al., Monoclonal antibody 11E10, which neutralizes shiga toxin type 2 (Stx2), recognizes three regions on the Stx2 A subunit, blocks the enzymatic action of the toxin in vitro, and alters the overall cellular distribution of the toxin. *Infect Immun,* 2009. Vol: p. 2730-2740.
79. Krautz-Peterson, G., et al., Intracellular neutralization of shiga toxin 2 by an a subunit-specific human monoclonal antibody. *Infect Immun,* 2008. Vol: p. 1931-1939.
80. Adekar, S. P., et al., Neutralization of botulinum neurotoxin by a human monoclonal antibody specific for the catalytic light chain. *PLoS One,* 2008. Vol: p. e3023.
81. Walker, L. M., et al., Broad and potent neutralizing antibodies from an African donor reveal a new HIV-1 vaccine target. *Science,* 2009. Vol: p. 285-289.
82. Seaman, M. N. and A. A. Peden, Ricin toxin hits a retrograde roadblock. *Cell,* Vol: p. 222-224.
83. Nencioni, L., et al., Properties of pertussis toxin mutant PT-9K/129G after formaldehyde treatment. *Infect Immun,* 1991. Vol: p. 625-630.
84. Kamachi, K. and Y. Arakawa, Development of safer pertussis DNA vaccine expressing non-toxic C180 polypeptide of pertussis toxin S1 subunit. *Vaccine,* 2007. Vol: p. 1000-1006.
85. Kamachi, K., T. Konda, and Y. Arakawa, DNA vaccine encoding pertussis toxin S1 subunit induces protection against *Bordetella pertussis* in mice. *Vaccine,* 2003. Vol: p. 4609-4615.
85. Outbreaks of respiratory illness mistakenly attributed to pertussis—New Hampshire, Massachusetts, and Tennessee, 2004-2006. MMWR Morb Mortal Wkly Rep, 2007. Vol: p. 837-842.
86. Senzilet, L. D., et al., Pertussis is a frequent cause of prolonged cough illness in adults and adolescents. Clin Infect Dis, 2001. Vol: p. 1691-1697.

87. Pichichero, M. E., et al., Acellular pertussis vaccine booster combined with diphtheria and tetanus toxoids for adolescents. Pediatrics, 2006. Vol: p. 1084-1093.
88. Tanaka, M., et al., Trends in pertussis among infants in the United States, 1980-1999. JAMA, 2003. Vol: p. 2968-2975.
89. O'Brien, J. A. and J. J. Caro, Hospitalization for pertussis: profiles and case costs by age. BMC Infect Dis, 2005. Vol: p. 57.
90. Granstrom, M. and G. Granstrom, Serological correlates in whooping cough. Vaccine, 1993. Vol: p. 445-448.
91. Hazes, B. and R. J. Read, Accumulating evidence suggests that several AB-toxins subvert the endoplasmic reticulum-associated protein degradation pathway to enter target cells. Biochemistry, 1997. Vol: p. 11051-11054.
92. Lencer, W. I., Retrograde transport of cholera toxin into the ER of host cells. Int J Med Microbiol, 2004. Vol: p. 491-494.
93. Stechmann, B., et al., Inhibition of retrograde transport protects mice from lethal ricin challenge. Cell, Vol: p. 231-242.
94. Hazes, B., et al., Crystal structure of the pertussis toxin-ATP complex: a molecular sensor. J Mol Biol, 1996. Vol: p. 661-671.
95. Bruss, J. B. and G. R. Siber, Protective effects of pertussis immunoglobulin (P-IGIV) in the aerosol challenge model. Clin Diagn Lab Immunol, 1999. Vol: p. 464-470.
96. Bruss, J. B., et al., Treatment of severe pertussis: a study of the safety and pharmacology of intravenous pertussis immunoglobulin. Pediatr Infect Dis J, 1999. Vol: p. 505-511.
97. Granstrom, M., et al., Specific immunoglobulin for treatment of whooping cough. Lancet, 1991. Vol: p. 1230-1233.
98. Sato, H., et al., Monoclonal antibody against pertussis toxin: effect on toxin activity and pertussis infections. Infect Immun, 1984. Vol: p. 422-428.
99. Kaslow, H. R., et al., Detection of antibodies inhibiting the ADP-ribosyltransferase activity of pertussis toxin in human serum. J Clin Microbiol, 1992. Vol: p. 1380-1387.
100. Cieplak, W., et al., Identification of a region in the S1 subunit of pertussis toxin that is required for enzymatic activity and that contributes to the formation of a neutralizing antigenic determinant. Proc Natl Acad Sci USA, 1988. Vol: p. 4667-4671.
101. Burnette, W. N., et al., Pertussis toxin S1 mutant with reduced enzyme activity and a conserved protective epitope. Science, 1988. Vol: p. 72-74.
102. Sutherland, J. N. and J. A. Maynard, Characterization of a key neutralizing epitope on pertussis toxin recognized by monoclonal antibody 1B7. Biochemistry, 2009. Vol: p. 11982-11993.
103. Sato, H. and Y. Sato, Protective activities in mice of monoclonal antibodies against pertussis toxin. Infect Immun, 1990. Vol: p. 3369-3374.
104. Antoine, R. and C. Locht, Roles of the disulfide bond and the carboxy-terminal region of the S1 subunit in the assembly and biosynthesis of pertussis toxin. Infect Immun, 1990. Vol: p. 1518-1526.
105. Rieber, N., et al., Differences of humoral and cellular immune response to an acellular pertussis booster in adolescents with a whole cell or acellular primary vaccination. Vaccine, 2008. Vol: p. 6929-6935.
106. el Baya, A., et al., Pertussis toxin. Entry into cells and enzymatic activity. Adv Exp Med Biol, 1997. Vol: p. 83-86.
107. Witvliet, M. H., et al., Binding of pertussis toxin to eucaryotic cells and glycoproteins. Infect Immun, 1989. Vol: p. 3324-3330.
108. Brennan, M. J., et al., Lectin-like binding of pertussis toxin to a 165-kilodalton Chinese hamster ovary cell glycoprotein. J Biol Chem, 1988. Vol: p. 4895-4899.
109. Sato, Y., et al., Separation and purification of the hemagglutinins from *Bordetella pertussis*. Infect Immun, 1983. Vol: p. 313-320.
110. Sato, H., et al., Effect of monoclonal antibody to pertussis toxin on toxin activity. Infect Immun, 1987. Vol: p. 909-915.
111. Draper, R. K. and M. I. Simon, The entry of diphtheria toxin into the mammalian cell cytoplasm: evidence for lysosomal involvement. J Cell Biol, 1980. Vol: p. 849-854.
112. Smith, M. J., et al., Monoclonal antibody 11E10, which neutralizes shiga toxin type 2 (Stx2), recognizes three regions on the Stx2 A subunit, blocks the enzymatic action of the toxin in vitro, and alters the overall cellular distribution of the toxin. Infect Immun, 2009. Vol: p. 2730-2740.
113. Krautz-Peterson, G., et al., Intracellular neutralization of shiga toxin 2 by an a subunit-specific human monoclonal antibody. Infect Immun, 2008. Vol: p. 1931-1939.
114. Adekar, S. P., et al., Neutralization of botulinum neurotoxin by a human monoclonal antibody specific for the catalytic light chain. PLoS One, 2008. Vol: p. e3023.
115. Walker, L. M., et al., Broad and potent neutralizing antibodies from an African donor reveal a new HIV-1 vaccine target. Science, 2009. Vol: p. 285-289.
116. Seaman, M. N. and A. A. Peden, Ricin toxin hits a retrograde roadblock. Cell, Vol: p. 222-224.
117. Nencioni, L., et al., Properties of pertussis toxin mutant PT-9K/129G after formaldehyde treatment. Infect Immun, 1991. Vol: p. 625-630.
118. Kamachi, K. and Y. Arakawa, Development of safer pertussis DNA vaccine expressing non-toxic C180 polypeptide of pertussis toxin S1 subunit. Vaccine, 2007. Vol: p. 1000-1006.
119. Kamachi, K., T. Konda, and Y. Arakawa, DNA vaccine encoding pertussis toxin S1 subunit induces protection against *Bordetella pertussis* in mice. Vaccine, 2003. Vol: p. 4609-4615.

What is claimed is:

1. A humanized antibody capable of binding a pertussis toxin protein, wherein the humanized antibody comprises the amino acid sequence of SEQ ID NO:1.

2. A pharmaceutical composition comprising a therapeutically effective amount of the humanized antibody of claim 1, and a pharmaceutically acceptable excipient 5.

3. A method of treating whooping cough in a subject in need thereof, comprising administering to the subject a therapeutically effective amount of the humanized antibody of claim 1 and a pharmaceutical carrier, thereby treating whooping cough in the subject.

* * * * *

UNITED STATES PATENT AND TRADEMARK OFFICE
CERTIFICATE OF CORRECTION

| | | |
|---|---|---|
| PATENT NO. | : 8,653,243 B2 | Page 1 of 1 |
| APPLICATION NO. | : 13/236530 | |
| DATED | : February 18, 2014 | |
| INVENTOR(S) | : Maynard et al. | |

It is certified that error appears in the above-identified patent and that said Letters Patent is hereby corrected as shown below:

In the Claims

Please delete "5" after the word "excipient" in Claim 2, column 103, line 34.

Signed and Sealed this
Seventh Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,653,243 B2  Page 1 of 1
APPLICATION NO. : 13/236530
DATED : February 18, 2014
INVENTOR(S) : Maynard et al.

It is certified that error appears in the above-identified patent and that said Letters Patent is hereby corrected as shown below:

In the Specification

Column 1, lines 25 - 27, delete

"This invention was made with government support under AI0662339 awarded by the National Institutes of Health. The Government has certain rights in the invention."

and replace with:

-- This invention was made with government support under AI066239 awarded by the National Institutes of Health. The Government has certain rights in the invention. --

Signed and Sealed this
Eighth Day of September, 2015

Michelle K. Lee
*Director of the United States Patent and Trademark Office*

SEQUENCE LISTING

<160> NUMBER OF SEQ ID NOS: 61

<210> SEQ ID NO 1
<211> LENGTH: 246
<212> TYPE: PRT
<213> ORGANISM: Artificial sequence
<220> FEATURE:
<223> OTHER INFORMATION: Synthetic polypeptide Hu1B7 scFv

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Phe Met
            20                  25                  30

Tyr Trp Tyr Gln Gln Lys Pro Gly Lys Ala Pro Lys Leu Leu Ile Tyr
        35                  40                  45

Leu Thr Ser Asn Leu Pro Ser Gly Val Pro Ser Arg Phe Ser Gly Phe
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser His Pro Pro Thr
                85                  90                  95

Phe Gly Gln Gly Thr Lys Val Glu Ile Lys Arg Thr Gly Gly Gly Gly
            100                 105                 110

Ser Gly Gly Gly Gly Ser Gly Gly Gly Ser Gly Gly Gly Gly Ser
            115                 120                 125

Glu Val Gln Leu Val Glu Ser Gly Gly Leu Val Gln Pro Gly Gly
            130                 135                 140

Ser Leu Arg Leu Ser Cys Ala Ala Ser Gly Tyr Lys Phe Thr Ser Tyr
145                 150                 155                 160

Trp Met His Trp Val Arg Gln Ala Pro Gly Lys Gly Leu Glu Trp Val
                165                 170                 175

Gly Asn Ile Phe Pro Gly Ser Gly Ser Thr Asn Tyr Asp Glu Lys Phe
                180                 185                 190

Asn Ser Arg Phe Thr Ile Ser Val Asp Thr Ser Lys Asn Thr Ala Tyr
                195                 200                 205

Leu Gln Met Asn Ser Leu Arg Ala Glu Asp Thr Ala Val Tyr Tyr Cys
        210                 215                 220

Thr Arg Trp Leu Ser Gly Ala Tyr Phe Asp Tyr Trp Gly Gln Gly Thr
225                 230                 235                 240

Leu Val Thr Val Ser Ser
                245

```
<210> SEQ ID NO 2
<211> LENGTH: 738
<212> TYPE: DNA
<213> ORGANISM: Artificial sequence
<220> FEATURE:
<223> OTHER INFORMATION: Synthetic DNA construct
<220> FEATURE:
<221> NAME/KEY: CDS
<222> LOCATION: (70)..(99)
<223> OTHER INFORMATION: CDR L1
<220> FEATURE:
<221> NAME/KEY: CDS
<222> LOCATION: (145)..(165)
<223> OTHER INFORMATION: CDR L2
<220> FEATURE:
<221> NAME/KEY: CDS
<222> LOCATION: (262)..(288)
<223> OTHER INFORMATION: CDR L3
<220> FEATURE:
<221> NAME/KEY: CDS
<222> LOCATION: (460)..(489)
<223> OTHER INFORMATION: CDR H1
<220> FEATURE:
<221> NAME/KEY: CDS
<222> LOCATION: (532)..(582)
<223> OTHER INFORMATION: CDR H2
<220> FEATURE:
<221> NAME/KEY: CDS
<222> LOCATION: (679)..(705)
```

<223> OTHER INFORMATION: CDR H3

<400> SEQUENCE: 2

```
gacatccaga tgacccagtc cccgtcctcc ctgtccgctt ccgttggtga ccgcgttacc      60 atcacctgc tcc gct tcc tcc tcc gtt tcc ttc atg tac tggtaccagc         109
          Ser Ala Ser Ser Ser Val Ser Phe Met Tyr
           1               5                  10 agaaaccggg taaagctccg aaactgctga tctac ctg acc tcc aac ctg ccg        162
                                        Leu Thr Ser Asn Leu Pro
                                                         15 tcc ggtgttccgt cccgcttctc cggtttcggt tccggtaccg actacaccct            215
Ser gaccatctcc tccctgcagc cggaagactt cgctacctac tactgc cag cag tgg        270
                                                   Gln Gln Trp
                                                            20 tcc tcc cac ccg ccg acc ttcggtcagg gtaccaaagt tgaaatcaaa              318
Ser Ser His Pro Pro Thr
             25 cgcaccggtg gtggtggttc tggtggtggt ggttctggcg gcggcggctc cggtggtggt     378 ggatccgaag ttcagctggt tgaatccggt ggtggtctag ttcagccggg tggttccctg     438 cgcctgtcct gcgctgcttc c ggt tac aaa ttc acc tcc tac tgg atg cac      489
                        Gly Tyr Lys Phe Thr Ser Tyr Trp Met His
                         30                          35 tgggttcgcc aggctccggg taaaggtctg gaatgggttg gt aac atc ttc ccg        543
                                                Asn Ile Phe Pro
                                                             40 ggt tcc ggt tcc acc aac tac gac gaa aaa ttc aac tcc cgcttcacca       592
Gly Ser Gly Ser Thr Asn Tyr Asp Glu Lys Phe Asn Ser
             45                          50 tctccgttga cacctccaaa aacaccgctt acctgcagat gaactccctg cgcgctgaag     652
acaccgctgt ttactactgc acccgc tgg ctg tcc ggt gct tac ttc gac tac     705
                                Trp Leu Ser Gly Ala Tyr Phe Asp Tyr
                                 55                      60 tggggtcagg gtaccctggt taccgtttcc tcg                                  738
```

<210> SEQ ID NO 3
<211> LENGTH: 10
<212> TYPE: PRT
<213> ORGANISM: Artificial sequence
<220> FEATURE:
<223> OTHER INFORMATION: Synthetic Construct

<400> SEQUENCE: 3

Ser Ala Ser Ser Ser Val Ser Phe Met Tyr
 1               5                  10

<210> SEQ ID NO 4
<211> LENGTH: 7
<212> TYPE: PRT
<213> ORGANISM: Artificial sequence
<220> FEATURE:
<223> OTHER INFORMATION: Synthetic Construct

<400> SEQUENCE: 4

Leu Thr Ser Asn Leu Pro Ser
 1               5

<210> SEQ ID NO 5
<211> LENGTH: 9
<212> TYPE: PRT
<213> ORGANISM: Artificial sequence
<220> FEATURE:
<223> OTHER INFORMATION: Synthetic Construct

<400> SEQUENCE: 5

Gln Gln Trp Ser Ser His Pro Pro Thr
1               5

<210> SEQ ID NO 6
<211> LENGTH: 10
<212> TYPE: PRT
<213> ORGANISM: Artificial sequence
<220> FEATURE:
<223> OTHER INFORMATION: Synthetic Construct

<400> SEQUENCE: 6

Gly Tyr Lys Phe Thr Ser Tyr Trp Met His
1               5                   10

<210> SEQ ID NO 7
<211> LENGTH: 17
<212> TYPE: PRT
<213> ORGANISM: Artificial sequence
<220> FEATURE:
<223> OTHER INFORMATION: Synthetic Construct

<400> SEQUENCE: 7

Asn Ile Phe Pro Gly Ser Gly Ser Thr Asn Tyr Asp Glu Lys Phe Asn
1               5                   10                  15

Ser

<210> SEQ ID NO 8
<211> LENGTH: 9
<212> TYPE: PRT
<213> ORGANISM: Artificial sequence
<220> FEATURE:
<223> OTHER INFORMATION: Synthetic Construct

<400> SEQUENCE: 8

Trp Leu Ser Gly Ala Tyr Phe Asp Tyr
1               5

<210> SEQ ID NO 9
<211> LENGTH: 235
<212> TYPE: PRT
<213> ORGANISM: Bordetella pertussis

<400> SEQUENCE: 9

Asp Asp Pro Pro Ala Thr Val Tyr Arg Tyr Asp Ser Arg Pro Pro Glu
1               5                   10                  15

Asp Val Phe Gln Asn Gly Phe Thr Ala Trp Gly Asn Asn Asp Asn Val
            20                  25                  30

Leu Glu His Leu Thr Gly Arg Ser Cys Gln Val Gly Ser Ser Asn Ser
        35                  40                  45

Ala Phe Val Ser Thr Ser Ser Ser Arg Arg Tyr Thr Glu Val Tyr Leu
    50                  55                  60

Glu His Arg Met Gln Glu Ala Val Glu Ala Glu Arg Ala Gly Arg Gly
65                  70                  75                  80

Thr Gly His Phe Ile Gly Tyr Ile Tyr Glu Val Arg Ala Asp Asn Asn
                85                  90                  95

Phe Tyr Gly Ala Ala Ser Ser Tyr Phe Glu Tyr Val Asp Thr Tyr Gly
            100                 105                 110

Asp Asn Ala Gly Arg Ile Leu Ala Gly Ala Leu Ala Thr Tyr Gln Ser
        115                 120                 125

Glu Tyr Leu Ala His Arg Arg Ile Pro Pro Glu Asn Ile Arg Arg Val
            130                 135                 140

Thr Arg Val Tyr His Asn Gly Ile Thr Gly Glu Thr Thr Thr Thr Glu
145                 150                 155                 160

Tyr Ser Asn Ala Arg Tyr Val Ser Gln Gln Thr Arg Ala Asn Pro Asn
                165                 170                 175

Pro Tyr Thr Ser Arg Arg Ser Val Ala Ser Ile Val Gly Thr Leu Val
            180                 185                 190

Arg Met Ala Pro Val Val Gly Ala Cys Met Ala Arg Gln Ala Glu Ser
            195                 200                 205

Ser Glu Ala Met Ala Ala Trp Ser Glu Arg Ala Gly Glu Ala Met Val
            210                 215                 220

Leu Val Tyr Tyr Glu Ser Ile Ala Tyr Ser Phe
225                 230                 235

<210> SEQ ID NO 10
<211> LENGTH: 196
<212> TYPE: PRT
<213> ORGANISM: Bordetella pertussis

<400> SEQUENCE: 10

Gly Ile Val Ile Pro Pro Gln Glu Gln Ile Thr Gln His Gly Ser Pro
1               5                   10                  15

Tyr Gly Arg Cys Ala Asn Lys Thr Arg Ala Leu Thr Val Ala Glu Leu
            20                  25                  30

Arg Gly Ser Gly Asp Leu Gln Glu Tyr Leu Arg His Val Thr Arg Gly
        35                  40                  45

Trp Ser Ile Phe Ala Leu Tyr Asp Gly Thr Tyr Leu Gly Gly Glu Tyr
    50                  55                  60

Gly Gly Val Ile Lys Asp Gly Thr Pro Gly Gly Ala Phe Asp Leu Lys
65                  70                  75                  80

Thr Thr Phe Cys Ile Met Thr Thr Arg Asn Thr Gly Gln Pro Ala Thr
                85                  90                  95

Asp His Tyr Tyr Ser Asn Val Thr Ala Thr Arg Leu Leu Ser Ser Thr
            100                 105                 110

Asn Ser Arg Leu Cys Ala Val Phe Val Arg Ser Gly Gln Pro Val Ile
        115                 120                 125

Gly Ala Cys Thr Ser Pro Tyr Asp Gly Lys Tyr Trp Ser Met Tyr Ser
    130                 135                 140

Arg Leu Arg Lys Met Leu Tyr Leu Ile Tyr Val Ala Gly Ile Ser Val
145                 150                 155                 160

Arg Val His Val Ser Lys Glu Glu Gln Tyr Tyr Asp Tyr Glu Asp Ala
                165                 170                 175

Thr Phe Glu Thr Tyr Ala Leu Thr Gly Ile Ser Ile Cys Asn Pro Gly
            180                 185                 190

Ser Ser Leu Cys
        195

<210> SEQ ID NO 11
<211> LENGTH: 196
<212> TYPE: PRT
<213> ORGANISM: Bordetella pertussis

<400> SEQUENCE: 11

Gly Ile Val Ile Pro Pro Lys Ala Leu Phe Thr Gln Gln Gly Gly Ala
1               5                   10                  15

Tyr Gly Arg Cys Pro Asn Gly Thr Arg Ala Leu Thr Val Ala Glu Leu
                20                  25                  30

Arg Gly Asn Ala Glu Leu Gln Thr Tyr Leu Arg Gln Ile Thr Pro Gly
            35                  40                  45

Trp Ser Ile Tyr Gly Leu Tyr Asp Gly Thr Tyr Leu Gly Gln Ala Tyr
 50                  55                  60

Gly Gly Ile Ile Lys Asp Ala Pro Pro Gly Ala Gly Phe Ile Tyr Arg
 65                  70                  75                  80

Glu Thr Phe Cys Ile Thr Thr Ile Tyr Lys Thr Gly Gln Pro Ala Ala
                85                  90                  95

Asp His Tyr Tyr Ser Lys Val Thr Ala Thr Arg Leu Leu Ala Ser Thr
            100                 105                 110

Asn Ser Arg Leu Cys Ala Val Phe Val Arg Asp Gly Gln Ser Val Ile
        115                 120                 125

Gly Ala Cys Ala Ser Pro Tyr Glu Gly Arg Tyr Arg Asp Met Tyr Asp
130                 135                 140

Ala Leu Arg Arg Leu Leu Tyr Met Ile Tyr Met Ser Gly Leu Ala Val
145                 150                 155                 160

Arg Val His Val Ser Lys Glu Glu Gln Tyr Tyr Asp Tyr Glu Asp Ala
                165                 170                 175

Thr Phe Gln Thr Tyr Ala Leu Thr Gly Ile Ser Leu Cys Asn Pro Ala
            180                 185                 190

Ala Ser Ile Cys
        195

<210> SEQ ID NO 12
<211> LENGTH: 110
<212> TYPE: PRT
<213> ORGANISM: Bordetella pertussis

<400> SEQUENCE: 12

Asp Val Pro Tyr Val Leu Val Lys Thr Asn Met Val Val Thr Ser Val
 1               5                  10                  15

Ala Met Lys Pro Tyr Glu Val Thr Pro Thr Arg Met Leu Val Cys Gly
                20                  25                  30

Ile Ala Ala Lys Leu Gly Ala Ala Ser Ser Pro Asp Ala His Val
            35                  40                  45

Pro Phe Cys Phe Gly Lys Asp Leu Lys Arg Pro Gly Ser Ser Pro Met
 50                  55                  60

Glu Val Met Leu Arg Ala Val Phe Met Gln Gln Arg Pro Leu Arg Met
 65                  70                  75                  80

Phe Leu Gly Pro Lys Gln Leu Thr Phe Glu Gly Lys Pro Ala Leu Glu
                85                  90                  95

Leu Ile Arg Met Val Glu Cys Ser Gly Lys Gln Asp Cys Pro
            100                 105                 110

<210> SEQ ID NO 13
<211> LENGTH: 98
<212> TYPE: PRT
<213> ORGANISM: Bordetella pertussis

<400> SEQUENCE: 13

Leu Pro Thr His Leu Tyr Lys Asn Phe Thr Val Gln Glu Leu Ala Leu
 1               5                  10                  15

Lys Leu Lys Gly Lys Asn Gln Glu Phe Cys Leu Thr Ala Phe Met Ser
                20                  25                  30

Gly Arg Ser Leu Val Arg Ala Cys Leu Ser Asp Ala Gly His Glu His

```
                        35                  40                  45
Asp Thr Trp Phe Asp Thr Met Leu Gly Phe Ala Ile Ser Ala Tyr Ala
 50                  55                  60

Leu Lys Ser Arg Ile Ala Leu Thr Val Glu Asp Ser Pro Tyr Pro Gly
 65                  70                  75                  80

Thr Pro Gly Asp Leu Leu Glu Leu Gln Ile Cys Pro Leu Asn Gly Tyr
                 85                  90                  95

Cys Glu

<210> SEQ ID NO 14
<211> LENGTH: 37
<212> TYPE: DNA
<213> ORGANISM: Artificial sequence
<220> FEATURE:
<223> OTHER INFORMATION: Synthetic DNA primer 5' scFc VL SfiI

<400> SEQUENCE: 14
ttactcgcgg cccagccggc catggcggac tacaaag                            37

<210> SEQ ID NO 15
<211> LENGTH: 40
<212> TYPE: DNA
<213> ORGANISM: Artificial sequence
<220> FEATURE:
<223> OTHER INFORMATION: Synthetic DNA primer 5' hu1B7 1-40

<400> SEQUENCE: 15
atggcggact acaaagacat ccagatgacc cagtccccgt                         40

<210> SEQ ID NO 16
<211> LENGTH: 40
<212> TYPE: DNA
<213> ORGANISM: Artificial sequence
<220> FEATURE:
<223> OTHER INFORMATION: Synthetic DNA primer 5' hu1B7 41-80

<400> SEQUENCE: 16
cctccctgtc cgcttccgtt ggtgaccgcg ttaccatcac                         40

<210> SEQ ID NO 17
<211> LENGTH: 40
<212> TYPE: DNA
<213> ORGANISM: Artificial sequence
<220> FEATURE:
<223> OTHER INFORMATION: Synthetic DNA primer 5' hu1B7 81-120

<400> SEQUENCE: 17
ctgctccgct tcctcctccg tttccttcat gtactggtac                         40

<210> SEQ ID NO 18
<211> LENGTH: 40
<212> TYPE: DNA
<213> ORGANISM: Artificial sequence
<220> FEATURE:
<223> OTHER INFORMATION: Synthetic DNA primer 5' hu1B7 121-160

<400> SEQUENCE: 18
cagcagaaac cgggtaaagc tccgaaactg ctgatctacc                         40

<210> SEQ ID NO 19
<211> LENGTH: 40
<212> TYPE: DNA
<213> ORGANISM: Artificial sequence
<220> FEATURE:
<223> OTHER INFORMATION: Synthetic DNA primer 5' hu1B7 161-200
```

```
<400> SEQUENCE: 19
tgacctccaa cctgccgtcc ggtgttccgt cccgcttctc                               40

<210> SEQ ID NO 20
<211> LENGTH: 40
<212> TYPE: DNA
<213> ORGANISM: Artificial sequence
<220> FEATURE:
<223> OTHER INFORMATION: Synthetic DNA primer 5' hu1B7 201-240

<400> SEQUENCE: 20
cggttccggt tccggtaccg actacaccct gaccatctcc                               40

<210> SEQ ID NO 21
<211> LENGTH: 40
<212> TYPE: DNA
<213> ORGANISM: Artificial sequence
<220> FEATURE:
<223> OTHER INFORMATION: Synthetic DNA primer 5' hu1B7 241-280

<400> SEQUENCE: 21
tccctgcagc cggaagactt cgctacctac tactgccagc                               40

<210> SEQ ID NO 22
<211> LENGTH: 40
<212> TYPE: DNA
<213> ORGANISM: Artificial sequence
<220> FEATURE:
<223> OTHER INFORMATION: Synthetic DNA primer 5' hu1B7 281-320

<400> SEQUENCE: 22
agtggtcctc ccacccgccg accttcggtc agggtaccaa                               40

<210> SEQ ID NO 23
<211> LENGTH: 40
<212> TYPE: DNA
<213> ORGANISM: Artificial sequence
<220> FEATURE:
<223> OTHER INFORMATION: Synthetic DNA primer 5' hu1B7 321-360

<400> SEQUENCE: 23
agttgaaatc aaacgcaccg gtggtggtgg ttctggtggt                               40

<210> SEQ ID NO 24
<211> LENGTH: 40
<212> TYPE: DNA
<213> ORGANISM: Artificial sequence
<220> FEATURE:
<223> OTHER INFORMATION: Synthetic DNA primer 5' hu1B7 361-400

<400> SEQUENCE: 24
ggtggttctg gcggcggcgg ctccggtggt ggtggatccg                               40

<210> SEQ ID NO 25
<211> LENGTH: 19
<212> TYPE: DNA
<213> ORGANISM: Artificial sequence
<220> FEATURE:
<223> OTHER INFORMATION: Synthetic DNA primer 5' hu1B7 401-440

<400> SEQUENCE: 25
aagttcagct ggttgaatc                                                     19

<210> SEQ ID NO 26
<211> LENGTH: 40
```

```
<212> TYPE: DNA
<213> ORGANISM: Artificial sequence
<220> FEATURE:
<223> OTHER INFORMATION: Synthetic DNA primer 5' hu1B7 441-480

<400> SEQUENCE: 26
cggtggtggt ctggttcagc cgggtggttc cctgcgcctg                               40

<210> SEQ ID NO 27
<211> LENGTH: 40
<212> TYPE: DNA
<213> ORGANISM: Artificial sequence
<220> FEATURE:
<223> OTHER INFORMATION: Synthetic DNA primer 5' hu1B7 481-520

<400> SEQUENCE: 27
tcctgcgctg cttccggtta caaattcacc tcctactgga                               40

<210> SEQ ID NO 28
<211> LENGTH: 40
<212> TYPE: DNA
<213> ORGANISM: Artificial sequence
<220> FEATURE:
<223> OTHER INFORMATION: Synthetic DNA primer 5' hu1B7 521-560

<400> SEQUENCE: 28
tgcactgggt tcgccaggct ccgggtaaag gtctggaatg                               40

<210> SEQ ID NO 29
<211> LENGTH: 40
<212> TYPE: DNA
<213> ORGANISM: Artificial sequence
<220> FEATURE:
<223> OTHER INFORMATION: Synthetic DNA primer 5' hu1B7 561-600

<400> SEQUENCE: 29
ggttggtaac atcttcccgg gttccggttc caccaactac                               40

<210> SEQ ID NO 30
<211> LENGTH: 40
<212> TYPE: DNA
<213> ORGANISM: Artificial sequence
<220> FEATURE:
<223> OTHER INFORMATION: Synthetic DNA primer 5' hu1B7 601-640

<400> SEQUENCE: 30
gacgaattca aaaactcccg cttcaccatc tccgttgaca                               40

<210> SEQ ID NO 31
<211> LENGTH: 40
<212> TYPE: DNA
<213> ORGANISM: Artificial sequence
<220> FEATURE:
<223> OTHER INFORMATION: Synthetic DNA primer 5' hu1B7 641-680

<400> SEQUENCE: 31
cctccaaaaa caccgcttac ctgcagatga actccctgcg                               40

<210> SEQ ID NO 32
<211> LENGTH: 40
<212> TYPE: DNA
<213> ORGANISM: Artificial sequence
<220> FEATURE:
<223> OTHER INFORMATION: Synthetic DNA primer 5' hu1B7 681-720

<400> SEQUENCE: 32
cgctgaagac accgctgttt actactgcac ccgctggctg                               40
```

<210> SEQ ID NO 33
<211> LENGTH: 40
<212> TYPE: DNA
<213> ORGANISM: Artificial sequence
<220> FEATURE:
<223> OTHER INFORMATION: Synthetic DNA primer 5' hu1B7 721-760

<400> SEQUENCE: 33
tccggtgctt acttcgacta ctggggtcag ggtaccctgg                             40

<210> SEQ ID NO 34
<211> LENGTH: 29
<212> TYPE: DNA
<213> ORGANISM: Artificial sequence
<220> FEATURE:
<223> OTHER INFORMATION: Synthetic DNA primer 5' hu1B7 761-789

<400> SEQUENCE: 34
ttaccgtttc ctcggcctcg ggggccgaa                                         29

<210> SEQ ID NO 35
<211> LENGTH: 40
<212> TYPE: DNA
<213> ORGANISM: Artificial sequence
<220> FEATURE:
<223> OTHER INFORMATION: Synthetic DNA primer 3' hu1B7 21-60

<400> SEQUENCE: 35
aacggaagcg gacagggagg acggggactg ggtcatctgg                             40

<210> SEQ ID NO 36
<211> LENGTH: 40
<212> TYPE: DNA
<213> ORGANISM: Artificial sequence
<220> FEATURE:
<223> OTHER INFORMATION: Synthetic DNA primer 3' hu1B7 61-100

<400> SEQUENCE: 36
cggaggagga agcggagcag gtgatggtaa cgcggtcacc                             40

<210> SEQ ID NO 37
<211> LENGTH: 40
<212> TYPE: DNA
<213> ORGANISM: Artificial sequence
<220> FEATURE:
<223> OTHER INFORMATION: Synthetic DNA primer 3' hu1B7 101-140

<400> SEQUENCE: 37
gctttacccg gtttctgctg gtaccagtac atgaaggaaa                             40

<210> SEQ ID NO 38
<211> LENGTH: 40
<212> TYPE: DNA
<213> ORGANISM: Artificial sequence
<220> FEATURE:
<223> OTHER INFORMATION: Synthetic DNA primer 3' hu1B7 141-180

<400> SEQUENCE: 38
ggacggcagg ttggaggtca ggtagatcag cagtttcgga                             40

<210> SEQ ID NO 39
<211> LENGTH: 40
<212> TYPE: DNA
<213> ORGANISM: Artificial sequence
<220> FEATURE:
<223> OTHER INFORMATION: Synthetic DNA primer 3' hu1B7 181-220

```
<400> SEQUENCE: 39
cggtaccgga accggaaccg gagaagcggg acggaacacc                              40

<210> SEQ ID NO 40
<211> LENGTH: 40
<212> TYPE: DNA
<213> ORGANISM: Artificial sequence
<220> FEATURE:
<223> OTHER INFORMATION: Synthetic DNA primer 3' hu1B7 221-260

<400> SEQUENCE: 40
aagtcttccg gctgcaggga ggagatggtc agggtgtagt                              40

<210> SEQ ID NO 41
<211> LENGTH: 40
<212> TYPE: DNA
<213> ORGANISM: Artificial sequence
<220> FEATURE:
<223> OTHER INFORMATION: Synthetic DNA primer 3' hu1B7 261-300

<400> SEQUENCE: 41
cggcgggtgg gaggaccact gctggcagta gtaggtagcg                              40

<210> SEQ ID NO 42
<211> LENGTH: 40
<212> TYPE: DNA
<213> ORGANISM: Artificial sequence
<220> FEATURE:
<223> OTHER INFORMATION: Synthetic DNA primer 3' hu1B7 301-340

<400> SEQUENCE: 42
cggtgcgttt gatttcaact ttggtaccct gaccgaaggt                              40

<210> SEQ ID NO 43
<211> LENGTH: 40
<212> TYPE: DNA
<213> ORGANISM: Artificial sequence
<220> FEATURE:
<223> OTHER INFORMATION: Synthetic DNA primer 3' hu1B7 341-380

<400> SEQUENCE: 43
ccgccgccgc cagaaccacc accaccagaa ccaccaccac                              40

<210> SEQ ID NO 44
<211> LENGTH: 40
<212> TYPE: DNA
<213> ORGANISM: Artificial sequence
<220> FEATURE:
<223> OTHER INFORMATION: Synthetic DNA primer 3' hu1B7 381-420

<400> SEQUENCE: 44
ggattcaacc agctgaactt cggatccacc accaccggag                              40

<210> SEQ ID NO 45
<211> LENGTH: 40
<212> TYPE: DNA
<213> ORGANISM: Artificial sequence
<220> FEATURE:
<223> OTHER INFORMATION: Synthetic DNA primer 3' hu1B7 421-460

<400> SEQUENCE: 45
gctgaaccag accaccaccg gattcaacca gctgaacttc                              40

<210> SEQ ID NO 46
<211> LENGTH: 40
```

```
<212> TYPE: DNA
<213> ORGANISM: Artificial sequence
<220> FEATURE:
<223> OTHER INFORMATION: Synthetic DNA primer 3' hu1B7 461-500

<400> SEQUENCE: 46
taaccggaag cagcgcagga caggcgcagg gaaccacccg                              40

<210> SEQ ID NO 47
<211> LENGTH: 40
<212> TYPE: DNA
<213> ORGANISM: Artificial sequence
<220> FEATURE:
<223> OTHER INFORMATION: Synthetic DNA primer 3' hu1B7 501-540

<400> SEQUENCE: 47
agcctggcga acccagtgca tccagtagga ggtgaatttg                              40

<210> SEQ ID NO 48
<211> LENGTH: 40
<212> TYPE: DNA
<213> ORGANISM: Artificial sequence
<220> FEATURE:
<223> OTHER INFORMATION: Synthetic DNA primer 3' hu1B7 541-580

<400> SEQUENCE: 48
ccgggaagat gttaccaacc cattccagac ctttacccgg                              40

<210> SEQ ID NO 49
<211> LENGTH: 40
<212> TYPE: DNA
<213> ORGANISM: Artificial sequence
<220> FEATURE:
<223> OTHER INFORMATION: Synthetic DNA primer 3' hu1B7 581-620

<400> SEQUENCE: 49
cgggagttga atttttcgtc gtagttggtg gaaccggaac                              40

<210> SEQ ID NO 50
<211> LENGTH: 40
<212> TYPE: DNA
<213> ORGANISM: Artificial sequence
<220> FEATURE:
<223> OTHER INFORMATION: Synthetic DNA primer 3' hu1B7 621-660

<400> SEQUENCE: 50
gtaagcggtg tttttggagg tgtcaacgga gatggtgaag                              40

<210> SEQ ID NO 51
<211> LENGTH: 40
<212> TYPE: DNA
<213> ORGANISM: Artificial sequence
<220> FEATURE:
<223> OTHER INFORMATION: Synthetic DNA primer 3' hu1B7 661-700

<400> SEQUENCE: 51
aaacagcggt gtcttcagcg cgcagggagt tcatctgcag                              40

<210> SEQ ID NO 52
<211> LENGTH: 40
<212> TYPE: DNA
<213> ORGANISM: Artificial sequence
<220> FEATURE:
<223> OTHER INFORMATION: Synthetic DNA primer 3' hu1B7 701-740

<400> SEQUENCE: 52
tagtcgaagt aagcaccgga cagccagcgg gtgcagtagt                              40
```

<210> SEQ ID NO 53
<211> LENGTH: 40
<212> TYPE: DNA
<213> ORGANISM: Artificial sequence
<220> FEATURE:
<223> OTHER INFORMATION: Synthetic DNA primer 3' hu1B7 741-780

<400> SEQUENCE: 53
cgaggccgag gaaacggtaa ccagggtacc ctgaccccag                40

<210> SEQ ID NO 54
<211> LENGTH: 24
<212> TYPE: DNA
<213> ORGANISM: Artificial sequence
<220> FEATURE:
<223> OTHER INFORMATION: Synthetic DNA primer 3' scFc VH SfiI

<400> SEQUENCE: 54
cctcggcctc gggggccgaa ttcc                                 24

<210> SEQ ID NO 55
<211> LENGTH: 747
<212> TYPE: DNA
<213> ORGANISM: Mus musculus

<400> SEQUENCE: 55
gatattcaga tgacccagtc tccagcactc atgtctgctt ctccagggga gaaggtcacc      60
atgaccttca gtgccagctc gagtgtaagt ttcatgtatt ggtaccagca gaagccaaga    120
tcgtccccca aaccctggat ttatctcaca tccaacctgc cttctggagt ccctgctcgc    180
ttcagtggca gtgggtctgg gacctcttac tctctcacaa tcagcagcat ggaggctgaa    240
gatgctgcca cttattactg ccaacagtgg agtagtcacc cacccacgtt cggctcgggg    300
acaaagttgg aaataaaacg tggtggtggt ggttctggtg gtggtggttc tggcggcggc    360
ggctccggtg gtggtggatc cgaggtccag ctgcaacagt ctgggtctga gctggtgagg    420
cctggagctt cagtgaagct gtcctgcaag gcttctggca caaaattcac cagctactgg    480
atgcactggg tgaagcagag gcctggacaa ggccttgagt ggattggaaa tattttctct    540
ggtagtggta gtactaacta cgatgagaag ttcaacagca aggccacact gactgtagac    600
acatcctcca acacagccta catgcagctc agcagcctga catctgagga ctctgcggtc    660
tattactgta caagatggct aagtggggcc tactttgact actggggcca gggcaccact    720
ctcacagtct cctcggcctc gggggcc                                       747

<210> SEQ ID NO 56
<211> LENGTH: 249
<212> TYPE: PRT
<213> ORGANISM: Mus musculus

<400> SEQUENCE: 56

Asp Ile Gln Met Thr Gln Ser Pro Ala Leu Met Ser Ala Ser Pro Gly
1               5                   10                  15

Glu Lys Val Thr Met Thr Cys Ser Ala Ser Ser Ser Val Ser Phe Met
            20                  25                  30

Tyr Trp Tyr Gln Gln Lys Pro Arg Ser Ser Pro Lys Pro Trp Ile Tyr
        35                  40                  45

Leu Thr Ser Asn Leu Pro Ser Gly Val Pro Ala Arg Phe Ser Gly Ser
    50                  55                  60

Gly Ser Gly Thr Ser Tyr Ser Leu Thr Ile Ser Ser Met Glu Ala Glu

```
            65                  70                  75                  80
Asp Ala Ala Thr Tyr Tyr Cys Gln Gln Trp Ser Ser His Pro Pro Thr
                85                  90                  95
Phe Gly Ser Gly Thr Lys Leu Glu Ile Lys Arg Gly Gly Gly Gly Ser
                100                 105                 110
Gly Gly Gly Gly Ser Gly Gly Gly Ser Gly Gly Gly Ser Glu
                115                 120                 125
Val Gln Leu Gln Gln Ser Gly Ser Glu Leu Val Arg Pro Gly Ala Ser
130                 135                 140
Val Lys Leu Ser Cys Lys Ala Ser Gly Tyr Lys Phe Thr Ser Tyr Trp
145                 150                 155                 160
Met His Trp Val Lys Gln Arg Pro Gln Gly Leu Glu Trp Ile Gly
                165                 170                 175
Asn Ile Phe Pro Gly Ser Gly Ser Thr Asn Tyr Asp Glu Lys Phe Asn
                180                 185                 190
Ser Lys Ala Thr Leu Thr Val Asp Thr Ser Ser Asn Thr Ala Tyr Met
                195                 200                 205
Gln Leu Ser Ser Leu Thr Ser Glu Asp Ser Ala Val Tyr Tyr Cys Thr
            210                 215                 220
Arg Trp Leu Ser Gly Ala Tyr Phe Asp Tyr Trp Gly Gln Gly Thr Thr
225                 230                 235                 240
Leu Thr Val Ser Ser Ala Ser Gly Ala
                245

<210> SEQ ID NO 57
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 57

Met Ala Asp Tyr Lys Asp Ile Gln Met Thr Gln Ser Pro Ser Ser Leu
1               5                   10                  15
Ser Ala Ser Val Gly Asp Arg Val Thr Ile Thr Cys Ser Ala Ser Ser
                20                  25                  30
Ser Val Ser Phe Met Tyr Trp Tyr Gln Gln Lys Pro Gly Lys Ala Pro
            35                  40                  45
Lys Leu Leu Ile Tyr Leu Thr Ser Asn Leu Pro Ser Gly Val Pro Ser
        50                  55                  60
Arg Phe Ser Gly Phe Gly Ser Gly Thr Asp Tyr Thr Leu Thr Ile Ser
65                  70                  75                  80
Ser Leu Gln Pro Glu Asp Phe Ala Thr Tyr Tyr Cys Gln Gln Trp Ser
                85                  90                  95
Ser His Pro Pro Thr Phe Gly Gln Gly Thr Lys Val Glu Ile Lys Arg
                100                 105                 110
Thr

<210> SEQ ID NO 58
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 58

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Tyr Lys Phe Thr Ser Tyr
            20                  25                  30

Trp Met His Trp Val Arg Gln Ala Pro Gly Lys Gly Leu Glu Trp Val
            35                  40                  45

Gly Asn Ile Phe Pro Gly Ser Gly Ser Thr Asn Tyr Asp Glu Lys Phe
 50                  55                  60

Asn Ser Arg Phe Thr Ile Ser Val Asp Thr Ser Lys Asn Thr Ala Tyr
 65                  70                  75                  80

Leu Gln Met Asn Ser Leu Arg Ala Glu Asp Thr Ala Val Tyr Tyr Cys
            85                  90                  95

Thr Arg Trp Leu Ser Gly Ala Tyr Phe Asp Tyr Trp Gly Gln Gly Thr
            100                 105                 110

Leu Val Thr Val Ser Ser Ala Ser
            115                 120

<210> SEQ ID NO 59
<211> LENGTH: 225
<212> TYPE: PRT
<213> ORGANISM: Artificial sequence
<220> FEATURE:
<223> OTHER INFORMATION: Synthetic polypeptide

<400> SEQUENCE: 59

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Ser Leu Val Ser Ile
            20                  25                  30

Ser Asn Tyr Leu Ala Trp Tyr Gln Gln Lys Pro Gly Lys Ala Pro Lys
            35                  40                  45

Leu Leu Ile Tyr Ala Ala Ser Ser Leu Glu Ser Gly Val Pro Ser Arg
 50                  55                  60

Phe Ser Gly Ser Gly Ser Gly Thr Asp Phe Thr Leu Thr Ile Ser Ser
 65                  70                  75                  80

Leu Gln Pro Glu Asp Phe Ala Thr Tyr Tyr Cys Gln Gln Tyr Asn Ser
            85                  90                  95

Leu Pro Trp Thr Phe Gly Gln Gly Thr Lys Val Glu Ile Lys Arg Thr
            100                 105                 110

Glu Val Gln Leu Val Glu Ser Gly Gly Leu Val Gln Pro Gly Gly
            115                 120                 125

Ser Leu Arg Leu Ser Cys Ala Ala Ser Gly Phe Thr Phe Ser Ser Tyr
            130                 135                 140

Ala Met Ser Trp Val Arg Gln Ala Pro Gly Lys Gly Leu Glu Trp Val
145                 150                 155                 160

Ser Val Ile Ser Gly Lys Gly Gly Ser Thr Tyr Tyr Ala Asp Ser Val
            165                 170                 175

Lys Gly Arg Phe Thr Ile Ser Arg Asp Asn Ser Lys Asn Thr Leu Tyr
            180                 185                 190

Leu Gln Met Asn Ser Leu Arg Ala Glu Asp Thr Ala Val Tyr Tyr Cys
            195                 200                 205

Ala Arg Gly Phe Asp Tyr Trp Gly Gln Gly Thr Leu Val Thr Val Ser
    210                 215                 220

Ser
225

<210> SEQ ID NO 60
<211> LENGTH: 253

```
<212> TYPE: PRT
<213> ORGANISM: Artificial Sequence
<220> FEATURE:
<223> OTHER INFORMATION: Synthetic polypeptide

<400> SEQUENCE: 60

Met Ala Asp Tyr Lys Asp Ile Gln Met Thr Gln Ser Pro Ser Ser Leu
1               5                   10                  15

Ser Ala Ser Val Gly Asp Arg Val Thr Ile Thr Cys Ser Ala Ser Ser
            20                  25                  30

Ser Val Ser Phe Met Tyr Trp Tyr Gln Gln Lys Pro Gly Lys Ala Pro
        35                  40                  45

Lys Leu Leu Ile Tyr Leu Thr Ser Asn Leu Pro Ser Gly Val Pro Ser
    50                  55                  60

Arg Phe Ser Gly Phe Gly Ser Gly Thr Asp Tyr Thr Leu Thr Ile Ser
65                  70                  75                  80

Ser Leu Gln Pro Glu Asp Phe Ala Thr Tyr Tyr Cys Gln Gln Trp Ser
                85                  90                  95

Ser His Pro Pro Thr Phe Gly Gln Gly Thr Lys Val Glu Ile Lys Arg
            100                 105                 110

Thr Gly Gly Gly Gly Ser Gly Gly Gly Ser Gly Gly Gly Gly Gly Ser
            115                 120                 125

Gly Gly Gly Gly Ser Glu Val Gln Leu Val Glu Ser Gly Gly Gly Leu
        130                 135                 140

Val Gln Pro Gly Gly Ser Leu Arg Leu Ser Cys Ala Ala Ser Gly Tyr
145                 150                 155                 160

Lys Phe Thr Ser Tyr Trp Met His Trp Val Arg Gln Ala Pro Gly Lys
                165                 170                 175

Gly Leu Glu Trp Val Gly Asn Ile Phe Pro Gly Ser Gly Ser Thr Asn
            180                 185                 190

Tyr Asp Glu Lys Phe Asn Ser Arg Phe Thr Ile Ser Val Asp Thr Ser
        195                 200                 205

Lys Asn Thr Ala Tyr Leu Gln Met Asn Ser Leu Arg Ala Glu Asp Thr
    210                 215                 220

Ala Val Tyr Tyr Cys Thr Arg Trp Leu Ser Gly Ala Tyr Phe Asp Tyr
225                 230                 235                 240

Trp Gly Gln Gly Thr Leu Val Thr Val Ser Ser Ala Ser
                245                 250

<210> SEQ ID NO 61
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 61

Met Ala Asp Tyr Lys Asp Ile Gln Met Thr Gln Ser Pro Ser Ser Leu
1               5                   10                  15

Ser Ala Ser Val Gly Asp Arg Val Thr Ile Thr Cys Arg Ala Ser Gln
            20                  25                  30

Ser Leu Val Ser Ile Ser Asn Tyr Leu Ala Trp Tyr Gln Gln Lys Pro
        35                  40                  45

Gly Lys Ala Pro Lys Leu Leu Ile Tyr Ala Ala Ser Ser Leu Glu Ser
    50                  55                  60

Gly Val Pro Ser Arg Phe Ser Gly Ser Gly Ser Gly Thr Asp Phe Thr
65                  70                  75                  80
```

-continued

```
Leu Thr Ile Ser Ser Leu Gln Pro Glu Asp Phe Ala Thr Tyr Tyr Cys
                85                  90                  95

Gln Gln Tyr Asn Ser Leu Pro Trp Thr Phe Gly Gln Gly Thr Lys Val
            100                 105                 110

Glu Ile Lys Arg Thr Glu Val Gln Leu Val Glu Ser Gly Gly Gly Leu
        115                 120                 125

Val Gln Pro Gly Gly Ser Leu Arg Leu Ser Cys Ala Ala Ser Gly Phe
    130                 135                 140

Thr Phe Ser Ser Tyr Ala Met Ser Trp Val Arg Gln Ala Pro Gly Lys
145                 150                 155                 160

Gly Leu Glu Trp Val Ser Val Ile Ser Gly Lys Gly Gly Ser Thr Tyr
                165                 170                 175

Tyr Ala Asp Ser Val Lys Gly Arg Phe Thr Ile Ser Arg Asp Asn Ser
            180                 185                 190

Lys Asn Thr Leu Tyr Leu Gln Met Asn Ser Leu Arg Ala Glu Asp Thr
        195                 200                 205

Ala Val Tyr Tyr Cys Ala Arg Gly Phe Asp Tyr Trp Gly Gln Gly Thr
    210                 215                 220

Leu Val Thr Val Ser Ser Ala Ser
225                 230
```